(12) United States Patent
Perrin

(10) Patent No.: US 9,744,220 B2
(45) Date of Patent: Aug. 29, 2017

(54) COMPOSITIONS AND METHODS FOR TREATING INFLAMMATORY DISEASES

(71) Applicant: TUFTS UNIVERSITY, Medford, MA (US)

(72) Inventor: Mercio A. Perrin, Chestnut Hill, MA (US)

(73) Assignee: Tufts University, Medford, MA (US)

(*) Notice: Subject to any disclaimer, the term of this patent is extended or adjusted under 35 U.S.C. 154(b) by 0 days.

(21) Appl. No.: 14/768,157

(22) PCT Filed: Mar. 14, 2014

(86) PCT No.: PCT/US2014/029323
§ 371 (c)(1),
(2) Date: Aug. 14, 2015

(87) PCT Pub. No.: WO2014/153153
PCT Pub. Date: Sep. 25, 2014

(65) Prior Publication Data
US 2015/0374802 A1     Dec. 31, 2015

Related U.S. Application Data

(60) Provisional application No. 61/918,260, filed on Dec. 19, 2013, provisional application No. 61/784,814, filed on Mar. 14, 2013.

(51) Int. Cl.
*A61K 38/16* (2006.01)
*A61K 38/47* (2006.01)
*C07K 14/475* (2006.01)

(52) U.S. Cl.
CPC .............. *A61K 38/47* (2013.01); *A61K 38/16* (2013.01); *C12Y 302/01018* (2013.01)

(58) Field of Classification Search
None
See application file for complete search history.

(56) References Cited

U.S. PATENT DOCUMENTS

| 2009/0117593 A1 | 5/2009 | Chuenkova et al. |
| 2011/0038887 A1 | 2/2011 | Contreras et al. |
| 2012/0245221 A1 | 9/2012 | Chuenkova et al. |
| 2012/0276131 A1 | 11/2012 | Coustou Linares et al. |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Cheunkova et al; 2005, Biochemistry, vol. 44, No. 48, pp. 15685-15694.*

* cited by examiner

*Primary Examiner* — Bridget E Bunner
*Assistant Examiner* — Fozia Hamud
(74) *Attorney, Agent, or Firm* — Melissa Hunter-Ensor; Leslie Serunian; Greenberg Traurig, LLP

(57) ABSTRACT

The invention provides compositions and methods for treating inflammatory diseases, such as cardiac or hepatic inflammatory diseases, involving the use of parasite-derived neurotrophic factor (PDNF), or fragment of PDNF. The invention also provides compositions featuring PDNF, or a fragment thereof, and methods for using such compositions for the proliferation and/or mobilization of a stem cell (e.g., cardiac stem cell) or progenitor cell (e.g., hepatic progenitor cell). In one aspect, the invention provides a method of decreasing inflammation in a nonneuronal tissue of a subject. In another aspect, the invention provides a method of decreasing inflammation in a cardiac, liver, pancreas, or gastrointestinal tissue of a subject. In still another aspect, the invention provides a method of increasing expression of an anti-inflammatory factor in a non-neuronal cell or tissue.

7 Claims, 20 Drawing Sheets

SEQ ID NO:1

```
   1 tgttcccctt ttctcttccc aactttctcc ggcggcaatc ccctgcaaa gagacgatct
  61 tgacaccatt gtcttaggca taatagaagt tctacaaaca acgcccgaag gacacacagg
 121 caggcaccga ctaccatggg gaaaacagtc gttgtggcca gtaggatctt ctggctaatg
 181 tttttcgtgc cgcttcttct tgcgatctgc cccagcgagc ccgcgtacgc cttggcaccc
 241 ggatcgagcc gagttgagct gtttaagcgt aagaattcga cggtgccctt tgaagacaag
 301 gccggcaaag tcaccgagcg ggttgtccac tcgttccgcc tcccgcct tgttaatgtg
 361 gacggggtga tggttgccat cgcggacgct cgctacgaca catccaatga caactccctc
 421 attgatacgg tggcgaagta cagcgtggac gatggggaga cgtgggacac ccaaattgcc
 481 atcaagaaca gccgtgtatc gtctgtttct cgtgtggtgg atcccaccgt gattgtgaag
 541 ggcaacaagc ttcgtcct ggttggaagc tactatagtt cgagaagcta ctggtcgtcg
 601 catggtgatg cgagagactg ggatattctg cttgccgttg gtgaggtcac gaagtccact
 661 gcgggcggca agataactgc gagtatcaaa tgggggagcc ccgtgtcact gaagaagttt
 721 tttccggcag aaatggaagg catgcacaca aatcaatttc ttggcggcgc gggtgttgcc
 781 attgtagcgt ccaacgggaa tcttgtgtac cctgtgcagg ttacgaacaa aaagaagcaa
 841 gttttctcca agatcttcta ctcggaagat gatggcaaga cgtggaactt tgggaagggt
 901 aggagcgatt ttggctgctc tgaacctgtg gcccttgagt gggagggcaa gctcatcata
 961 aacacccgag ttgactggaa acgccgtctg gtgtacgagt ccagtgacat ggagaaaccg
1021 tgggtggagg ctgtcggaac cgtctcgcgt gtgtggggcc cctcaccaaa atcgaaccag
1081 cccggcagtc agagcagctt cactgccgtg accatcgaag gaatgcgtgt gatgctcttc
1141 acacacccgc tgaattttaa gggaaggtgg ctgcgcgacc gactgaacct ctggctgacg
1201 gataaccagc gcatttataa cgttgggcaa gtatccattg gtgatgaaaa ttccgcctac
1261 agctccgtcc tgcacaagga tgataagctg tactgtttgc atgagatcaa cacggacgag
1321 gtgtacagcc ttgttttgc acgcctggtt ggcgagctac ggatcatcaa atcagtgctg
1381 cggtcctgga agaattggga cagccacctg tccagcattt gcaccccgc tgatccagcc
1441 gcttcgtcgt cagagagtgg ttgtggtccc gctgtcacca cggttggcct tgttggcttt
1501 ttgtccggca acgcctccca aaacgtatgg gaggatgcgt accgctgcgt caacgcaagc
1561 acggcaaatg cggagagggt tcggaacggt ttgaagttg cggggtcgg cggaggagcg
1621 ctttggccgg tgagccagca ggggcagaat cagcggtatc gttttgcaaa ccacgcgttc
1681 acgctggtgg cgtcggtgac gattcacgag gctccgaggg ccgcgagtcc cttgctgggt
1741 gcgagcctgg actcttctgg cggcaaaaaa ctcctggggc tctcgtacga cgagaagcac
1801 cagtggcagc caatatacgg atcaacgccg gtgacgccga cgggatcctg ggagacgggt
1861 aaaaggtacc acttggttct tacgatggcg aataaaattg gctccgtcta cattgatgga
1921 gaacttctgg agggttcagg acagaccgtt gtgccagacg ggaggaccgc tgacatctcc
1981 cacttctacg ttggcgggta taaaggagt gatatgccaa ccataagcca cgtgacggtg
2041 aataatgttc ttctttacaa ccgacagctg aataccgagg agatcagcac cttgttcttg
2101 agccaggacc ttattggcac ggaagcacac atg
```

FIG. 1A

SEQ ID NO:2

```
  1 MGKTVVVASR MFWLMFFVPL LLAICPSEPA YALAPGSSRV ELFKRKNSTV PFEDKAGKVT
 61 ERVVHSFRLP ALVNVDGVMV AIADARYDTS NDNSLIDTVA KYSVDDGETW ETQIAIKNSR
121 VSSVSRVVDP TVIVKGNKLY VLVGSYYSSR SYWSSHGDAR DWDILLAVGE VTKSTAGGKI
181 TASIKWGSPV SLKKFFPAEM EGMHTNQFLG GAGVAIVASN GNLVYPVQVT NKKKQVFSKI
241 FYSEDDGKTW KFGKGRSDFG CSEPVALEWE GKLIINTRVD WKRRLVYESS DMEKPWVEAV
301 GTVSRVWGPS PKSNQPGSQS SFTAVTIEGM RVMLFTHPLN FKGRWLRDRL NLWLTDNQRI
361 YNVGQVSIGD ENSAYSSVLY KDDKLYCLHE INTDEVYSLV FARLVGELRI IKSVLRSWKN
421 WDSHLSSICT PADPAASSSE SGCGPAVTTV GLVGFLSGNA SQNWEDAYR CVNASTANAE
481 RVRNGLKFAG VGGGALWPVS QQGQNQRYRF ANHAFTLVAS VTIHEAPRAA SPLLGASLDS
541 SGGKKLLGLS YDEKHQWQPI YGSTPVTPTG SWETGKRYHL VLTMANKIGS VYIDGELLEG
601 SGQTVVPDGR TPDISHFYVG GYKRSDMPTI SHVTVNNVLL YNRQLNTEEI RTLFLSQDLI
661 GTEAHM
```

FIG. 1B

SEQ ID NO:3

```
   1 aaagaccgtt ggaagaagaa agaaggttcc ggagcgtggc caccaccaac gatgaactgc
  61 cacaattgcg tgctgtccgc ggcggtacc cggcgctttg agcccacggc gacttgtgtg
 121 ttccccttc tcttcccact ttctccgcgg caatccccct gcaaagagac gatcttgaca
 181 ccattgtttt aggcataata gaagttctac aaacaacgcc gaaggacac acaggcaggc
 241 accgactacg atggggaaaa cactcgttgt ggccagtagg atgttctggc taatgtttt
 301 cgtgccgctt cttcttgcga tctgcccag cgagcccgcg tacgccctgg cacccggatc
 361 gagccgagtt gagggtttaa gcctaagaat tcgacggtgc cgtttgaaga caaggccggc
 421 aaagtcaccg agcgggttgt ccactcgttc cgcttccccg ccttgttaa tgtggacggg
 481 gtgatgttg ccatcgcgga cgctcgctac gaaacatcca gtgaaaactc cctcattgat
 541 acggtggcga agtacagcgt ggacgatggg gagacgtggg agacccaaat tgccatcaag
 601 aacagccgtg tatcgtctgt ttctcgtgtg gtggatccca ccgtgattgt gaagggcaac
 661 aagctttacg tcctggttgg aacctactat agttcgagaa gctactggtc gtcgcatggt
 721 gatgcgagag actgggatat tctgcttgcc gttggtgagg tcacgaagtc cactgcgggc
 781 ggcaagataa ctgcgagtat caaatggggg agccccgtgt cactgaagaa gttttttccg
 841 gcagaaatgg aaggcatgca cacaaatcaa tttcttggcg gcgcgggtgt tgccattgta
 901 gcgtccaacg ggaatcttgt gtaccctgtg caggttacga caaaaggaa gcaagttttc
 961 tccaagatct tctactcgga agatgatggc aagacgtgga gtttgggaa gggtaggagc
1021 gattttggct gctctgaacc tgtggccctt gagtgggagg ggaagctcat cataaacacc
1081 cgagttgact ggaaacgccg tctggtgtac gagtccagtg acatggagaa accgtgggtg
1141 gaggctgtcg gaaccgtctc gcctgtgtgg ggcccctcac caaaatcgaa ccagcccggc
1201 agtcagacga gcttcactgc cgtgaccatc gaaggaatgc gtgtgatgct cttcacacac
1261 ccgctgaatt taagggaag gtccgtgcgc gaccgactga acctctggct gacggataac
1321 cagcgcattt ataacgttgg gcaagtatcc attggtgatg aaaattccgc ctacagctcc
1381 gtcctgtaca aggatgataa gctgtactgt ttgcatgaga tcaacacgga cgaggtgtac
1441 agccttgttt ttgcacgcct ggttggcgag ctacggatca ttaaatcagt gctgcggtcc
1501 tggaagaatt ggacagccac ctgtccagca tttgcacccc tgctgatcca gccgcttcgt
1561 cgtcagagag tggttgtggt cccgctgtca ccacggttgg tcttgttggc ttttgtcgg
1621 caacgcctcc caaaacgtat ggcaggatcg taccgctgcg tcaacgcaag cacggcaaat
1681 gcggagaggg ttcggaacgg tttgaagttt gcggggttg gcggaggagc gctttggccg
1741 gtgagccagc aggggcagaa tcagcggtat cgttttgcaa ccacgcgtt cacgctggtg
1801 gcgtcggtga cgattcacga ggctccgagg gccgcgagtc ccttgctggg tgcgagcctg
1861 gactcttctg gcggcaaaaa actcctgggg ctctcgtacg acgagaagca ccagtggcag
1921 ccaatatacg gatcaacgcc ggtgacgccg acgggatcgt gggagacggg taaaaggtac
1981 cacttggttc ttacgatggc gaataaaatt ggctccgtgt acattgatgg agaacttctg
2041 gagggttcag gacagaccgt tgtgccagac gggaggacgc ctgacatctc ccacttctac
2101 gttggcgggt ataaaaggag tgatatgcca accataagcc acgtgacggt gaataatgtt
2161 cttctttaca accgacgaca gctgaatacc gaggagatca ggaccttgtt cttgagccag
2221 gaccttattg gcacggaagc acacatggac agcagcagcg acagcagtgc ccacagtacg
2281 ccctcaactc ccgctgacag cactgcccac agtacgccct caactcccgt tgacagcagt
2341 gcccacagta cgccctcgac tccgctgac agcagtgccc acggtacgcc ctcaactccc
2401 gttgacagca gtgcccacgg tacgccctca actccgctg acagcagtgc ccacggtacg
2461 ccctcaactc ccgttgacag cactgcccac agtacgccct caactcccgt tgacagcagt
```

FIG. 1C-1

```
2521 gcccacagta cgccctcaac tcccgttgac agcagtgccc acggtgcgcc ctcaactccc
2581 gctgacagca gtgcccacgg tacgccctcg actcccgttg acagcagtgc ccacggtacg
2641 ccctcgactc ccgctgacag cagtgcccac agtacgccct cgactcccgc tgacagcagt
2701 gcccacagta cgccctcgac tcccgctgac agcagtgccc acagtacgcc ctcgactccc
2761 gttgacagca gtgcccacgg tacgccctcg actcccgctg acagcagtgc ccacagtacg
2821 ccctcgactc ccgctgacag cagtgcccac ggtacgccct caactcccgt tgacagcagt
2881 gcccacagta cgccctcgac tcccgttgac agcagtgccc acggtacgcc ctcaactccc
2941 gttgacagca gtgcccacag tacgccctcg actcccgttg acagcagtgc ccacggtacg
3001 ccctcaactc ccgttgacag cagtgcccac agtacgccct cgactcccgc tgacagcagt
3061 gcccacagta cgccctcaac tcccgctgac agcagtgccc acggtacgcc ctcaactccc
3121 gttgacagca gtgcccacag tacgccctcg actcccgctg acagcagtgc ccacagtacg
3181 ccctcaactc ccgttgacag cagtgcccac agtacgccct caactcccgc tgacagcagt
3241 gcccacggta cgccctcaac tcccgttgac agcagtgccc acggtacgcc ctcgactccc
3301 gctgacagca gtgcccacag tacgccctcg actcccgctg acagcagtgc ccacagtacg
3361 ccctcgactc ccgctgacag cagtgcccac agtacgccct caactcccgt tgacagcagt
3421 gcccacagta cgccctcaac tcccgctgac agcagtgccc acagtacgcc ctcaactccc
3481 gctgacagca gtgcccacag tacgccctcg actcccgctg acagcagtgc ccacagtacg
3541 ccctcaactc ccgttgacag cagtgcccac agtacgccct caactcccgc tgacagcagt
3601 gcccacggta cgccctcgac tcccgctgac agcagtgccc acagtacgcc ctcgactccc
3661 gttgacagca gtgcccacag tacgccctcg actcccgctg acagcagtgc ccacggtacg
3721 ccctcgactc ccgctgacag cagtgcccac agtacgccct cgactcccgc tgacagcagt
3781 gcccacggta cgccctcgac tcccgctgac agcagtgccc acagtacgcc ctcaactccc
3841 gctggcagca gcgccaatgg tacggttctg attttgcccg atggcgctgc actttcgacc
3901 ttttcgggcg gagggcttct tctgtgtgcg tgtgctttgc tgctgcacgt gttttttatg
3961 gcagttttct gatgtagtga gagagtctcc taacaaatgt agataaattc ataattgtgg
4021 tgtgaaccgt ttgggtaaat gtgtgtgtgc gctctcataa ggaaatgatt tccagtaatg
4081 ttttttttt gttctcgaac attttgaata aatctgcaga cagatgggga cgcgtaattt
4141 gaatttgttt ttcagcgttc ttttgtcact ggccccttgt ttaagtggaa ccgcgttgca
4201 atgcggcgag ggcatttctc tgttttgatt tccttctttt tctcctttgt gtttcttcaa
4261 tttgacggtt tgcacgctgt gcggtggagc gttttccctt gtgaaataag ggccaactgc
4321 ttcacagtgg cacgagggcg ctcaagagat ccgcgggtcg ccagtgactc actttgtgtg
4381 gcgcagctcg aggaggtgtc tggctgctgt ggggcctcg atggttgcca cttcgcgagt
4441 ttgcaacgag cgtgcttctc gcggagggag caggcgaaat attttgtttt ttttttttgt
4501 tttttttgtt ttttgttttt tgtgtgtgtg tgtaagtttt ggttcagtct cccttgaact
4561 gggggacgtt gggcttaatg gaccaaaact ctgattcccct aaaacttctt ttgttggttt
4621 tcttttgttt ttgttttttgt gctgctgatt tgcacgcttt ctcactgtca ccgaagcgcg
4681 gcggcggtgt ttgagtgccc cctcacgctg ctgctgtgga atttgcgttg cttgcggaca
4741 tttctgttgg gtcgcattgc tttctacttc gtttttatt tttgtggttt ggtggagggg
4801 agtgtgcagc aggggggcggg ccgagatgcc tgtggagaca gcgacgttgc ggggactctc
4861 tctcggcctc gtcattcaac aatccattgc gcagcaggtt gccacgaaca ccagcaccaa
4921 tatttgttcg ttttcccact attaccggcg cgtctagccg cacgatgcca tctgggtgcc
4981 gaggaggcgg ttgagcagcg gaaaaggctt cctgctatga agcgactgcc attgagagaa
5041 cttttagctg cgtggatctt cctcaatgcc cagccgttgg cgcgcagcgg aggtgcctgg
```

FIG. 1C-2

```
5101 gcattctagg agcagatggc gaaaggtttc ctgcgcgtca actggcgtgt ctgtggaggt
5161 tggctatcct cagtcgcgag accgcctcct ggcaccacag aacgggtagc ggtagtgtct
5221 tggcgaatag tacaaccgca cttgttgctg actgggcagt aaagcatgtc agcgggtccg
5281 tgtgccatac gggcgcattc catgttccgt gtgttgtccg gttgccatgg tctgcgtcgc
5341 atgctgagcc gcaggctcgt caacatgcac tccacaatgt ccgtaagaaa actcccggtg
5401 cac
```

FIG. 1C-3

SEQ ID NO.4

```
   1  MVAIADARYE TSSENSLIDT VAKYSVDDGE TWETQIAIKN SRVSSVSRVV DPTVIVKGNK
  61  LYVLVGSYYS SRSYWSSHGD ARDWDILLAV GEVTKSTAGG KITASIKWGS PVSLKKFFPA
 121  EMEGMHTNQF LGGAGVAIVA SNGNLVYPVQ VTNKRKQVFS KIFYSEDDGK TWKFGKGRSD
 181  FGCSEPVALE WEGKLIINTR VDWKRRLVYE SSDMEKPWVE AVGTVSRVWG PSPKSNQPGS
 241  QTSFTAVTIE GMRVMLFTHP LNFKGRCVRD RLNLWLTDNQ RIYNVGQVSI GDENSAYSSV
 301  LYKDDKLYCL HEINTDEVYS LVFARLVGEL RIIKSVLRSW KNWTATCPAF APLLIQPLRR
 361  QRVVVPLSP RLVLLAFCRQ RLPKRMGGSY RCVNASTANA ERVRNGLKFA GVGGGALWPV
 421  SQQGQNQRYR FANHAFTLVA SVTIHEAPRA ASPLLGASLD SSGGKKLLGL SYDEKHQWQP
 481  IYGSTPVTPT GSWETGKRYH LVLTMANKIG SVYIDGELLE GSGQTVVPDG RTPDISHFYV
 541  GGYKRSDMPT ISHVTVNNVL LYNRRQLNTE EIRTLFLSQD LIGTEAHMDS SSDSSAHSTP
 601  STPADSSAHS TPSTPVDSSA HSTPSTPADS SAHGTPSTPV DSSAHGTPST PADSSAHGTP
 663  STPVDSSAHS TPSTPVDSSA HSTPSTPVDS SAHGAPSTPA DSSAHGTPST PVDSSAHGTP
 721  STPADSSAHS TPSTPADSSA HSTPSTPVDS SAHGTPSTPV DSSAHGTPST PADSSAHSTP
 781  STPVDSSAHS TPSTPVDSSA HSTPSTPVDS SAHGTPSTPV DSSAHSTPST PVDSSAHGTP
 841  STPVDSSAHS TPSTPADSSA HSTPSTPVDS SAHGTPSTPA DSSAHSTPST PADSSAHSTP
 901  STPADSSAHS TPSTPVDSSA HSTPSTPADS SAHSTPSTPA DSSAHSTPST PADSSAHSTP
 961  STPVDSSAHS TPSTPVDSSA HSTPSTPVDS SAHSTPSTPV DSSAHSTPST PADSSAHSTP
1021  STPVDSSAHS TPSTPADSSA HGTPSTPADS SAHSTPSTPV DSSAHSTPST PADSSAHGTP
1081  STPADSSAHS TPSTPADSSA HGTPSTPADS SAHSTPSTPA GSSANGTVLI LPDGAALSTF
1141  SGGGLLLCAC ALLLHVFFMA VF
```

FIG. 1D

SEQUENCE LISTING

<160> NUMBER OF SEQ ID NOS: 16

<210> SEQ ID NO 1
<211> LENGTH: 2133
<212> TYPE: DNA
<213> ORGANISM: Trypanosoma cruzi

<400> SEQUENCE: 1

```
tgttcccctt ttctcttccc aactttctcc ggcggcaatc ccctgcaaa gagacgatct      60 tgacaccatt gttttaggca taatagaagt tctacaaaca acgcccgaag gacacacagg    120
caggcaccga ctaccatggg gaaaacagtc gttgtggcca gtaggatgtt ctggctaatg    180
tttttcgtgc cgcttcttct tgcgatctgc cccagcgagc ccgcgtacgc cttggcaccc    240
ggatcgagcc gagttgagct gtttaagcgt aagaattcga cggtgccgtt tgaagacaag    300
gccggcaaag tcaccgagcg ggttgtccac tcgttccgcc tccccgccct tgttaatgtg    360
gacggggtga tggttgccat cgcggacgct cgctacgaca catccaatga caactccctc    420
attgatacgg tggcgaagta cagcgtggac gatggggaga cgtgggagac ccaaattgcc    480
atcaagaaca gccgtgtatc gtctgtttct cgtgtggtgg atcccaccgt gattgtgaag    540
ggcaacaagc tttacgtcct ggttggaagc tactatagtt cgagaagcta ctggtcgtcg    600
catggtgatg cgagagactg ggatattctg cttgccgttg gtgaggtcac gaagtccact    660
gcgggcggca agataactgc gagtatcaaa tgggggagcc ccgtgtcact gaagaagttt    720
tttccggcag aaatggaagg catgcacaca aatcaatttc ttggcggcgc gggtgttgcc    780
attgtagcgt ccaacgggaa tcttgtgtac cctgtgcagg ttacgaacaa aaagaagcaa    840
gttttctcca agatcttcta ctcggaagat gatggcaaga cgtggaagtt tgggaagggt    900
aggagcgatt ttggctgctc tgaacctgtg gcccttgagt gggaggggaa gctcatcata    960
aacacccgag ttgactggaa acgccgtctg gtgtacgagt ccagtgacat ggagaaaccg   1020
tgggtggagg ctgtcggaac cgtctcgcgt gtgtggggcc cctcaccaaa atcgaaccag   1080
cccggcagtc agagcagctt cactgccgtg accatcgaag gaatgcgtgt gatgctcttc   1140
acacacccgc tgaattttaa gggaaggtgg ctgcgcgacc gactgaacct ctggctgacg   1200
gataaccagc gcatttataa cgttgggcaa gtatccattg gtgatgaaaa ttccgcctac   1260
agctccgtcc tgtacaagga tgataagctg tactgtttgc atgagatcaa cacggacgag   1320
gtgtacagcc ttgttttttgc acgcctggtt ggcgagctac ggatcattaa atcagtgctg   1380
cggtcctgga agaattggga cagccacctg tccagcattt gcacccctgc tgatccagcc   1440
gcttcgtcgt cagagagtgg ttgtggtccc gctgtcacca cggttggtct tgttggcttt   1500
ttgtccggca acgcctccca aaacgtatgg gaggatgcgt accgctgcgt caacgcaagc   1560
acggcaaatg cggagagggt tcggaacggt ttgaagtttg cggggggttgg cggaggagcg   1620 cttttggccgg tgagccagca ggggcagaat cagcggtatc gttttgcaaa ccacgcgttc   1680
acgctggtgg cgtcggtgac gattcacgag gctccgaggg ccgcgagtcc cttgctgggt   1740
gcgagcctgg actcttctgg cggcaaaaaa ctcctggggc tctcgtacga cgagaagcac   1800
cagtggcagc caatatacgg atcaacgccg gtgacgccga cgggatcgtg ggagacgggt   1860
aaaaggtacc acttggttct tacgatggcg aataaaattg gctccgtgta cattgatgga   1920
gaacttctgg agggttcagg acagaccgtt gtgccagacg ggaggacgcc tgacatctcc   1980
cacttctacg ttggcgggta taaaggagt gatatgccaa ccataagcca cgtgacggtg   2040
aataatgttc ttctttacaa ccgacagctg aataccgagg agatcaggac cttgttcttg   2100
```
agccaggacc ttattggcac ggaagcacac atg         2133

<210> SEQ ID NO 2
<211> LENGTH: 666
<212> TYPE: PRT
<213> ORGANISM: Trypanosoma cruzi

<400> SEQUENCE: 2

```
Met Gly Lys Thr Val Val Ala Ser Arg Met Phe Trp Leu Met Phe
1               5                   10                  15

Phe Val Pro Leu Leu Ala Ile Cys Pro Ser Glu Pro Ala Tyr Ala
                20                  25                  30

Leu Ala Pro Gly Ser Ser Arg Val Glu Leu Phe Lys Arg Lys Asn Ser
                35                  40                  45

Thr Val Pro Phe Glu Asp Lys Ala Gly Lys Val Thr Glu Arg Val Val
        50                  55                  60

His Ser Phe Arg Leu Pro Ala Leu Val Asn Val Asp Gly Val Met Val
65                  70                  75                  80

Ala Ile Ala Asp Ala Arg Tyr Asp Thr Ser Asn Asp Asn Ser Leu Ile
                85                  90                  95

Asp Thr Val Ala Lys Tyr Ser Val Asp Asp Gly Glu Thr Trp Glu Thr
                100                 105                 110

Gln Ile Ala Ile Lys Asn Ser Arg Val Ser Ser Val Ser Arg Val Val
                115                 120                 125

Asp Pro Thr Val Ile Val Lys Gly Asn Lys Leu Tyr Val Leu Val Gly
        130                 135                 140

Ser Tyr Tyr Ser Ser Arg Ser Tyr Trp Ser Ser His Gly Asp Ala Arg
145                 150                 155                 160

Asp Trp Asp Ile Leu Leu Ala Val Gly Glu Val Thr Lys Ser Thr Ala
                165                 170                 175

Gly Gly Lys Ile Thr Ala Ser Ile Lys Trp Gly Ser Pro Val Ser Leu
                180                 185                 190

Lys Lys Phe Phe Pro Ala Glu Met Glu Gly Met His Thr Asn Gln Phe
        195                 200                 205

Leu Gly Gly Ala Gly Val Ala Ile Val Ala Ser Asn Gly Asn Leu Val
    210                 215                 220

Tyr Pro Val Gln Val Thr Asn Lys Lys Gln Val Phe Ser Lys Ile
225                 230                 235                 240

Phe Tyr Ser Glu Asp Asp Gly Lys Thr Trp Lys Phe Gly Lys Gly Arg
                245                 250                 255

Ser Asp Phe Gly Cys Ser Glu Pro Val Ala Leu Glu Trp Glu Gly Lys
                260                 265                 270

Leu Ile Ile Asn Thr Arg Val Asp Trp Lys Arg Arg Leu Val Tyr Glu
            275                 280                 285

Ser Ser Asp Met Glu Lys Pro Trp Val Glu Ala Val Gly Thr Val Ser
        290                 295                 300

Arg Val Trp Gly Pro Ser Pro Lys Ser Asn Gln Pro Gly Ser Gln Ser
305                 310                 315                 320

Ser Phe Thr Ala Val Thr Ile Glu Gly Met Arg Val Met Leu Phe Thr
                325                 330                 335

His Pro Leu Asn Phe Lys Gly Arg Trp Leu Arg Asp Arg Leu Asn Leu
                340                 345                 350

Trp Leu Thr Asp Asn Gln Arg Ile Tyr Asn Val Gly Gln Val Ser Ile
            355                 360                 365
```

Gly Asp Glu Asn Ser Ala Tyr Ser Ser Val Leu Tyr Lys Asp Asp Lys
    370                 375                 380

Leu Tyr Cys Leu His Glu Ile Asn Thr Asp Glu Val Tyr Ser Leu Val
385                 390                 395                 400

Phe Ala Arg Leu Val Gly Glu Leu Arg Ile Ile Lys Ser Val Leu Arg
                405                 410                 415

Ser Trp Lys Asn Trp Asp Ser His Leu Ser Ser Ile Cys Thr Pro Ala
                420                 425                 430

Asp Pro Ala Ala Ser Ser Glu Ser Gly Cys Gly Pro Ala Val Thr
                435                 440                 445

Thr Val Gly Leu Val Gly Phe Leu Ser Gly Asn Ala Ser Gln Asn Val
    450                 455                 460

Trp Glu Asp Ala Tyr Arg Cys Val Asn Ala Ser Thr Ala Asn Ala Glu
465                 470                 475                 480

Arg Val Arg Asn Gly Leu Lys Phe Ala Gly Val Gly Gly Ala Leu
                485                 490                 495

Trp Pro Val Ser Gln Gly Gln Asn Gln Arg Tyr Arg Phe Ala Asn
                500                 505                 510

His Ala Phe Thr Leu Val Ala Ser Val Thr Ile His Glu Ala Pro Arg
                515                 520                 525

Ala Ala Ser Pro Leu Leu Gly Ala Ser Leu Asp Ser Ser Gly Gly Lys
    530                 535                 540

Lys Leu Leu Gly Leu Ser Tyr Asp Glu Lys His Gln Trp Gln Pro Ile
545                 550                 555                 560

Tyr Gly Ser Thr Pro Val Thr Pro Thr Gly Ser Trp Glu Thr Gly Lys
                565                 570                 575

Arg Tyr His Leu Val Leu Thr Met Ala Asn Lys Ile Gly Ser Val Tyr
                580                 585                 590

Ile Asp Gly Glu Leu Leu Glu Gly Ser Gly Gln Thr Val Pro Asp
                595                 600                 605

Gly Arg Thr Pro Asp Ile Ser His Phe Tyr Val Gly Gly Tyr Lys Arg
    610                 615                 620

Ser Asp Met Pro Thr Ile Ser His Val Thr Val Asn Asn Val Leu Leu
625                 630                 635                 640

Tyr Asn Arg Gln Leu Asn Thr Glu Glu Ile Arg Thr Leu Phe Leu Ser
                645                 650                 655

Gln Asp Leu Ile Gly Thr Glu Ala His Met
                660                 665

<210> SEQ ID NO 3
<211> LENGTH: 5403
<212> TYPE: DNA
<213> ORGANISM: Trypanosoma cruzi

<400> SEQUENCE: 3
aaagaccgtt ggaagaagaa agaaggttcc ggagcgtggc caccaccaac gatgaactgc      60
cacaattgcg tgctgtccgc gggcggtacc cggcgctttg agcccacggc gacttgtgtg     120 ttccccttc tcttcccact ttctccgcgg caatccccct gcaaagagac gatcttgaca     180
ccattgtttt aggcataata gaagttctac aaacaacgcc cgaaggacac acaggcaggc     240
accgactacg atggggaaaa cagtcgttgt ggccagtagg atgttctggc taatgttttt     300
cgtgccgctt cttcttgcga tctgccccag cgagcccgcg tacgcctgg cacccggatc     360 gagccgagtt gagggtttaa gcgtaagaat tcgacggtgc cgtttgaaga caaggccggc     420

| | |
|---|---|
| aaagtcaccg agcgggttgt ccactcgttc cgcttcccg cccttgttaa tgtggacggg | 480 |
| gtgatggttg ccatcgcgga cgctcgctac gaaacatcca gtgaaaactc cctcattgat | 540 |
| acggtggcga agtacagcgt ggacgatggg gagacgtggg agacccaaat tgccatcaag | 600 |
| aacagccgtg tatcgtctgt ttctcgtgtg gtggatccca ccgtgattgt gaagggcaac | 660 |
| aagctttacg tcctggttgg aagctactat agttcgagaa gctactggtc gtcgcatggt | 720 |
| gatgcgagag actgggatat tctgcttgcc gttggtgagg tcacgaagtc cactgcgggc | 780 |
| ggcaagataa ctgcgagtat caaatggggg agcccgtgt cactgaagaa gttttttccg | 840 |
| gcagaaatgg aaggcatgca cacaaatcaa tttcttggcg cgcgggtgt tgccattgta | 900 |
| gcgtccaacg ggaatcttgt gtaccctgtg caggttacga caaaaggaa gcaagttttc | 960 |
| tccaagatct tctactcgga agatgatggc aagacgtgga agtttgggaa gggtaggagc | 1020 |
| gattttggct gctctgaacc tgtggccctt gagtgggagg ggaagctcat cataaacacc | 1080 |
| cgagttgact ggaaacgccg tctggtgtac gagtccagtg acatggagaa accgtgggtg | 1140 |
| gaggctgtcg gaaccgtctc gcgtgtgtgg ggcccctcac caaaatcgaa ccagcccggc | 1200 |
| agtcagacga gcttcactgc cgtgaccatc gaaggaatgc gtgtgatgct cttcacacac | 1260 |
| ccgctgaatt ttaagggaag gtgcgtgcgc gaccgactga acctctggct gacggataac | 1320 |
| cagcgcattt ataacgttgg gcaagtatcc attggtgatg aaaattccgc ctacagctcc | 1380 |
| gtcctgtaca aggatgataa gctgtactgt ttgcatgaga tcaacacgga cgaggtgtac | 1440 |
| agccttgttt ttgcacgcct ggttggcgag ctacggatca ttaaatcagt gctgcggtcc | 1500 |
| tggaagaatt ggacagccac ctgtccagca tttgcacccc tgctgatcca gccgcttcgt | 1560 |
| cgtcagagag tggttgtggt cccgctgtca ccacggttgg tcttgttggc tttttgtcgg | 1620 |
| caacgcctcc caaacgtat gggaggatcg taccgctgcg tcaacgcaag cacggcaaat | 1680 |
| gcggagaggg ttcggaacgg tttgaagttt gcggggttg gcggaggagc gctttggccg | 1740 |
| gtgagccagc aggggcagaa tcagcggtat cgttttgcaa accacgcgtt cacgctggtg | 1800 |
| gcgtcggtga cgattcacga ggctccgagg gccgcgagtc ccttgctggg tgcgagcctg | 1860 |
| gactcttctg gcggcaaaaa actcctgggg ctctcgtacg acgagaagca ccagtggcag | 1920 |
| ccaatatacg gatcaacgcc ggtgacgccg acgggatcgt gggagacggg taaaaggtac | 1980 |
| cacttggttc ttacgatggc gaataaaatt ggctccgtgt acattgatgg agaacttctg | 2040 |
| gagggttcag gacagaccgt tgtgccagac gggaggacgc ctgacatctc ccacttctac | 2100 |
| gttggcgggt ataaaggag tgatatgcca accataagcc acgtgacggt gaataatgtt | 2160 |
| cttctttaca accgacgaca gctgaatacc gaggagatca ggaccttgtt cttgagccag | 2220 |
| gaccttattg gcacggaagc acacatggac agcagcagcg acagcagtgc ccacagtacg | 2280 |
| ccctcaactc ccgctgacag cagtgcccac agtacgccct caactcccgt tgacagcagt | 2340 |
| gcccacagta cgccctcgac tcccgctgac agcagtgccc acggtacgcc ctcaactccc | 2400 |
| gttgacagca gtgcccacgg tacgccctca actcccgctg acagcagtgc ccacggtacg | 2460 |
| ccctcaactc ccgttgacag cagtgcccac agtacgccct caactcccgt tgacagcagt | 2520 |
| gcccacagta cgccctcaac tcccgttgac agcagtgccc acgtgcgcc tcaactccc | 2580 |
| gctgacagca gtgcccacgg tacgccctcg actcccgttg acagcagtgc ccacggtacg | 2640 |
| ccctcgactc ccgctgacag cagtgcccac agtacgccct cgactcccgc tgacagcagt | 2700 |
| gcccacagta cgccctcgac tcccgctgac agcagtgccc acagtacgcc ctcgactccc | 2760 |

```
gttgacagca gtgcccacgg tacgccctcg actcccgctg acagcagtgc ccacagtacg      2820
ccctcgactc ccgctgacag cagtgcccac ggtacgccct caactcccgt tgacagcagt      2880
gcccacagta cgccctcgac tcccgttgac agcagtgccc acggtacgcc ctcaactccc      2940
gttgacagca gtgcccacag tacgccctcg actcccgttg acagcagtgc ccacggtacg      3000
ccctcaactc ccgttgacag cagtgcccac agtacgccct cgactcccgc tgacagcagt      3060
gcccacagta cgccctcaac tcccgctgac agcagtgccc acggtacgcc ctcaactccc      3120
gttgacagca gtgcccacag tacgccctcg actcccgctg acagcagtgc ccacagtacg      3180
ccctcaactc ccgttgacag cagtgcccac agtacgccct caactcccgc tgacagcagt      3240
gcccacggta cgccctcaac tcccgttgac agcagtgccc acggtacgcc ctcgactccc      3300
gctgacagca gtgcccacag tacgccctcg actcccgctg acagcagtgc ccacagtacg      3360
ccctcgactc ccgctgacag cagtgcccac agtacgccct caactcccgt tgacagcagt      3420
gcccacagta cgccctcaac tcccgctgac agcagtgccc acagtacgcc ctcaactccc      3480
gctgacagca gtgcccacag tacgccctcg actcccgctg acagcagtgc ccacagtacg      3540
ccctcaactc ccgttgacag cagtgcccac agtacgccct caactcccgc tgacagcagt      3600
gcccacggta cgccctcgac tcccgctgac agcagtgccc acagtacgcc ctcgactccc      3660
gttgacagca gtgcccacag tacgccctcg actcccgctg acagcagtgc ccacggtacg      3720
ccctcgactc ccgctgacag cagtgcccac agtacgccct cgactcccgc tgacagcagt      3780
gcccacggta cgccctcgac tcccgctgac agcagtgccc acagtacgcc ctcaactccc      3840
gctggcagca gcgccaatgg tacggttctg attttgcccg atggcgctgc actttcgacc      3900
ttttcgggcg gagggcttct tctgtgtgcg tgtgctttgc tgctgcacgt gttttttatg      3960
gcagttttct gatgtagtga gagtctccc   taacaaatgt agataaattc ataattgtgg      4020
tgtgaaccgt ttgggtaaat gtgtgtgtgc gctctcataa ggaaatgatt ccagtaatg       4080 tttttttttt gttctcgaac attttgaata aatctgcaga cagatgggga cgcgtaattt       4140
gaatttgttt ttcagcgttc ttttgtcact ggccccttgt ttaagtggaa ccgcgttgca      4200
atgcggcgag ggcatttctc tgttttgatt tccttctttt tctcctttgt gtttcttcaa      4260
tttgacggtt tgcacgctgt gcggtggagc gttttcccct gtgaaataag ggccaactgc      4320
ttcacagtgg cacagggcg  ctcaagagat ccgcgggtcg ccagtgactc actttgtgtg      4380
gcgcagctcg aggaggtgtc tggctgctgt gggggcctcg atggttgcca cttcgcgagt      4440
ttgcaacgag cgtgcttctc gcggagggag caggcgaaat attttgtttt ttttttttgt      4500
tttttttgtt ttttgttttt tgtgtgtgtg tgtaagtttt ggttcagtct cccttgaact      4560
gggggacgtt gggcttaatg gaccaaactc tgattcccct aaaacttctt tgttggttt       4620 tcttttgttt ttgttttgt gctgctgatt tgcacgcttt ctcactgtca ccgaagcgcg       4680
gcggcggtgt ttgagtgccc cctcacgctg ctgctgtgga atttgcgttg cttgcggaca      4740
tttctgttgg gtcgcattgc tttctacttc gttttttatt tttgtggttt ggtggagggg      4800
agtgtgcagc agggggcggg ccgagatgcc tgtggagaca gcgacgttgc ggggactctc      4860
tctcggcctc gtcattcaac aatccattgc gcagcaggtt gccacgaaca ccagcaccaa      4920
tatttgttcg ttttcccact attaccggcg cgtctagccg cacgatgcca tctgggtgcc      4980
gaggaggcgg ttgagcagcg gaaaaggctt cctgctatga agcgactgcc attgagagaa      5040
cttttagctg cgtggatctt cctcaatgcc cagccgttgg cgcgcagcgg aggtgcctgg      5100
gcattctagg agcagatggc gaaaggtttc ctgcgcgtca actggcgtgt ctgtggaggt      5160
```

```
tggctatcct cagtcgggag accgcctcct ggcaccacag aacgggtagc ggtagtgtct    5220
tggcgaatag tacaacgcca cttgttgctg actgggcagt aaagcatgtc agcgggtccg    5280
tgtgccatac gggcgcattc catgttccgt gtgttgtccg gttgccatgg tctgcgtcgc    5340
atgctgagcc gcaggctcgt caacatgcac tccacaatgt ccgtaagaaa actcccggtg    5400
cac                                                                  5403
```

<210> SEQ ID NO 4
<211> LENGTH: 1162
<212> TYPE: PRT
<213> ORGANISM: Trypanosoma cruzi

<400> SEQUENCE: 4

```
Met Val Ala Ile Ala Asp Ala Arg Tyr Glu Thr Ser Ser Glu Asn Ser
1               5                   10                  15

Leu Ile Asp Thr Val Ala Lys Tyr Ser Val Asp Asp Gly Glu Thr Trp
            20                  25                  30

Glu Thr Gln Ile Ala Ile Lys Asn Ser Arg Val Ser Ser Val Ser Arg
        35                  40                  45

Val Val Asp Pro Thr Val Ile Val Lys Gly Asn Lys Leu Tyr Val Leu
    50                  55                  60

Val Gly Ser Tyr Tyr Ser Ser Arg Ser Tyr Trp Ser Ser His Gly Asp
65                  70                  75                  80

Ala Arg Asp Trp Asp Ile Leu Leu Ala Val Gly Val Thr Lys Ser
            85                  90                  95

Thr Ala Gly Gly Lys Ile Thr Ala Ser Ile Lys Trp Gly Ser Pro Val
            100                 105                 110

Ser Leu Lys Lys Phe Phe Pro Ala Glu Met Glu Gly Met His Thr Asn
        115                 120                 125

Gln Phe Leu Gly Gly Ala Gly Val Ala Ile Val Ala Ser Asn Gly Asn
    130                 135                 140

Leu Val Tyr Pro Val Gln Val Thr Asn Lys Arg Lys Gln Val Phe Ser
145                 150                 155                 160

Lys Ile Phe Tyr Ser Glu Asp Asp Gly Lys Thr Trp Lys Phe Gly Lys
                165                 170                 175

Gly Arg Ser Asp Phe Gly Cys Ser Glu Pro Val Ala Leu Glu Trp Glu
            180                 185                 190

Gly Lys Leu Ile Ile Asn Thr Arg Val Asp Trp Lys Arg Arg Leu Val
        195                 200                 205

Tyr Glu Ser Ser Asp Met Glu Lys Pro Trp Val Glu Ala Val Gly Thr
    210                 215                 220

Val Ser Arg Val Trp Gly Pro Ser Pro Lys Ser Asn Gln Pro Gly Ser
225                 230                 235                 240

Gln Thr Ser Phe Thr Ala Val Thr Ile Glu Gly Met Arg Val Met Leu
                245                 250                 255

Phe Thr His Pro Leu Asn Phe Lys Gly Arg Cys Val Arg Asp Arg Leu
            260                 265                 270

Asn Leu Trp Leu Thr Asp Asn Gln Arg Ile Tyr Asn Val Gly Gln Val
        275                 280                 285

Ser Ile Gly Asp Glu Asn Ser Ala Tyr Ser Ser Val Leu Tyr Lys Asp
    290                 295                 300

Asp Lys Leu Tyr Cys Leu His Glu Ile Asn Thr Asp Glu Val Tyr Ser
305                 310                 315                 320
```

```
Leu Val Phe Ala Arg Leu Val Gly Glu Leu Arg Ile Ile Lys Ser Val
                325                 330                 335

Leu Arg Ser Trp Lys Asn Trp Thr Ala Thr Cys Pro Ala Phe Ala Pro
            340                 345                 350

Leu Leu Ile Gln Pro Leu Arg Arg Gln Arg Val Val Val Pro Leu
        355                 360                 365

Ser Pro Arg Leu Val Leu Leu Ala Phe Cys Arg Gln Arg Leu Pro Lys
    370                 375                 380

Arg Met Gly Gly Ser Tyr Arg Cys Val Asn Ala Ser Thr Ala Asn Ala
385                 390                 395                 400

Glu Arg Val Arg Asn Gly Leu Lys Phe Ala Gly Val Gly Gly Gly Ala
                405                 410                 415

Leu Trp Pro Val Ser Gln Gln Gly Gln Asn Gln Arg Tyr Arg Phe Ala
            420                 425                 430

Asn His Ala Phe Thr Leu Val Ala Ser Val Thr Ile His Glu Ala Pro
        435                 440                 445

Arg Ala Ala Ser Pro Leu Leu Gly Ala Ser Leu Asp Ser Ser Gly Gly
    450                 455                 460

Lys Lys Leu Leu Gly Leu Ser Tyr Asp Glu Lys His Gln Trp Gln Pro
465                 470                 475                 480

Ile Tyr Gly Ser Thr Pro Val Thr Pro Thr Gly Ser Trp Glu Thr Gly
                485                 490                 495

Lys Arg Tyr His Leu Val Leu Thr Met Ala Asn Lys Ile Gly Ser Val
            500                 505                 510

Tyr Ile Asp Gly Glu Leu Leu Glu Gly Ser Gly Gln Thr Val Val Pro
        515                 520                 525

Asp Gly Arg Thr Pro Asp Ile Ser His Phe Tyr Val Gly Gly Tyr Lys
    530                 535                 540

Arg Ser Asp Met Pro Thr Ile Ser His Val Thr Val Asn Asn Val Leu
545                 550                 555                 560

Leu Tyr Asn Arg Arg Gln Leu Asn Thr Glu Glu Ile Arg Thr Leu Phe
                565                 570                 575

Leu Ser Gln Asp Leu Ile Gly Thr Glu Ala His Met Asp Ser Ser Ser
            580                 585                 590

Asp Ser Ser Ala His Ser Thr Pro Ser Thr Pro Ala Asp Ser Ser Ala
        595                 600                 605

His Ser Thr Pro Ser Thr Pro Val Asp Ser Ser Ala His Ser Thr Pro
    610                 615                 620

Ser Thr Pro Ala Asp Ser Ser Ala His Gly Thr Pro Ser Thr Pro Val
625                 630                 635                 640

Asp Ser Ser Ala His Gly Thr Pro Ser Thr Pro Ala Asp Ser Ser Ala
                645                 650                 655

His Gly Thr Pro Ser Thr Pro Val Asp Ser Ser Ala His Ser Thr Pro
            660                 665                 670

Ser Thr Pro Val Asp Ser Ser Ala His Ser Thr Pro Ser Thr Pro Val
        675                 680                 685

Asp Ser Ser Ala His Gly Ala Pro Ser Thr Pro Ala Asp Ser Ser Ala
    690                 695                 700

His Gly Thr Pro Ser Thr Pro Val Asp Ser Ser Ala His Gly Thr Pro
705                 710                 715                 720

Ser Thr Pro Ala Asp Ser Ser Ala His Ser Thr Pro Ser Thr Pro Ala
                725                 730                 735

Asp Ser Ser Ala His Ser Thr Pro Ser Thr Pro Ala Asp Ser Ser Ala
```

```
              740                 745                 750
His Ser Thr Pro Ser Thr Pro Val Asp Ser Ser Ala His Gly Thr Pro
              755                 760                 765
Ser Thr Pro Ala Asp Ser Ser Ala His Ser Thr Pro Ser Thr Pro Ala
              770                 775                 780
Asp Ser Ser Ala His Gly Thr Pro Ser Thr Pro Val Asp Ser Ser Ala
785                 790                 795                 800
His Ser Thr Pro Ser Thr Pro Val Asp Ser Ser Ala His Gly Thr Pro
              805                 810                 815
Ser Thr Pro Val Asp Ser Ser Ala His Ser Thr Pro Ser Thr Pro Val
              820                 825                 830
Asp Ser Ser Ala His Gly Thr Pro Ser Thr Pro Val Asp Ser Ser Ala
              835                 840                 845
His Ser Thr Pro Ser Thr Pro Ala Asp Ser Ser Ala His Ser Thr Pro
              850                 855                 860
Ser Thr Pro Ala Asp Ser Ser Ala His Gly Thr Pro Ser Thr Pro Val
865                 870                 875                 880
Asp Ser Ser Ala His Ser Thr Pro Ser Thr Pro Ala Asp Ser Ser Ala
              885                 890                 895
His Ser Thr Pro Ser Thr Pro Val Asp Ser Ser Ala His Ser Thr Pro
              900                 905                 910
Ser Thr Pro Ala Asp Ser Ser Ala His Gly Thr Pro Ser Thr Pro Val
              915                 920                 925
Asp Ser Ser Ala His Gly Thr Pro Ser Thr Pro Ala Asp Ser Ser Ala
              930                 935                 940
His Ser Thr Pro Ser Thr Pro Ala Asp Ser Ser Ala His Ser Thr Pro
945                 950                 955                 960
Ser Thr Pro Ala Asp Ser Ser Ala His Ser Thr Pro Ser Thr Pro Val
              965                 970                 975
Asp Ser Ser Ala His Ser Thr Pro Ser Thr Pro Ala Asp Ser Ser Ala
              980                 985                 990
His Ser Thr Pro Ser Thr Pro Ala  Asp Ser Ser Ala His  Ser Thr Pro
              995                 1000                1005
Ser Thr  Pro Ala Asp Ser Ser  Ala His Ser Thr Pro  Ser Thr Pro
              1010                1015                1020
Val Asp  Ser Ser Ala His Ser  Thr Pro Ser Thr Pro  Ala Asp Ser
              1025                1030                1035
Ser Ala  His Gly Thr Pro Ser  Thr Pro Ala Asp Ser  Ser Ala His
              1040                1045                1050
Ser Thr  Pro Ser Thr Pro Val  Asp Ser Ser Ala His  Ser Thr Pro
              1055                1060                1065
Ser Thr  Pro Ala Asp Ser Ser  Ala His Gly Thr Pro  Ser Thr Pro
              1070                1075                1080
Ala Asp  Ser Ser Ala His Ser  Thr Pro Ser Thr Pro  Ala Asp Ser
              1085                1090                1095
Ser Ala  His Gly Thr Pro Ser  Thr Pro Ala Asp Ser  Ser Ala His
              1100                1105                1110
Ser Thr  Pro Ser Thr Pro Ala  Gly Ser Ser Ala Asn  Gly Thr Val
              1115                1120                1125
Leu Ile  Leu Pro Asp Gly Ala  Ala Leu Ser Thr Phe  Ser Gly Gly
              1130                1135                1140
Gly Leu  Leu Leu Cys Ala Cys  Ala Leu Leu Leu His  Val Phe Phe
              1145                1150                1155
```

Met Ala Val Phe
            1160

<210> SEQ ID NO 5
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Lys Thr Val Val Ala Ser Arg Met Phe Trp Leu Met Phe
1               5                   10                  15

Phe Val Pro Leu Leu Ala Ile Cys Pro Ser Glu Pro Ala Tyr Ala
                20                  25                  30

Leu Ala Pro Gly Ser Ser Arg Val Glu Leu Phe Lys Arg Lys Asn Ser
            35                  40                  45

Thr Val Pro Phe Glu Asp Lys Ala Gly Lys Val Thr Glu Arg Val Val
    50                  55                  60

His Ser Phe Arg Leu Pro Ala Leu Val Asn Val Asp Gly Val Met Val
65                  70                  75                  80

Ala Ile Ala Asp Ala Arg Tyr Asp Thr Ser Asn Asp Asn Ser Leu Ile
                85                  90                  95

Asp Thr Val Ala Lys Tyr Ser Val Asp Gly Glu Thr Trp Glu Thr
            100                 105                 110

Gln Ile Ala Ile Lys Asn Ser Arg Val Ser Ser Val Ser Arg Val Val
        115                 120                 125

Asp Pro Thr Val Ile Val Lys Gly Asn Lys Leu Tyr Val Leu Val Gly
    130                 135                 140

Ser Tyr Tyr Ser Ser Arg Ser Tyr Trp Ser Ser His Gly Asp Ala Arg
145                 150                 155                 160

Asp Trp Asp Ile Leu Leu Ala Val Gly Glu Val Thr Lys Ser Thr Ala
                165                 170                 175

Gly Gly Lys Ile Thr Ala Ser Ile Lys Trp Gly Ser Pro Val Ser Leu
            180                 185                 190

Lys Lys Phe Phe Pro Ala Glu Met Glu Gly Met His Thr Asn Gln Phe
        195                 200                 205

Leu Gly Gly Ala Gly Val Ala Ile Val Ala Ser Asn Gly Asn Leu Val
    210                 215                 220

Tyr Pro Val Gln Val Thr Asn Lys Lys Gln Val Phe Ser Lys Ile
225                 230                 235                 240

Phe Tyr Ser Glu Asp Asp Gly Lys Thr Trp Lys Phe Gly Lys Gly Arg
                245                 250                 255

Ser Asp Phe Gly Cys Ser Glu Pro Val Ala Leu Glu Trp Glu Gly Lys
            260                 265                 270

Leu Ile Ile Asn Thr Arg Val Asp Trp Lys Arg Leu Val Tyr Glu
        275                 280                 285

Ser Ser Asp Met Glu Lys Pro Trp Val Glu Ala Val Gly Thr Val Ser
    290                 295                 300

Arg Val Trp Gly Pro Ser Pro Lys Ser Asn Gln Pro Gly Ser Gln Ser
305                 310                 315                 320

Ser Phe Thr Ala Val Thr Ile Glu Gly Met Arg Val Met Leu Phe Thr
                325                 330                 335

His Pro Leu Asn Phe Lys Gly Arg Trp Leu Arg Asp Arg Leu Asn Leu

```
              340             345             350
Trp Leu Thr Asp Asn Gln Arg Ile Tyr Asn Val Gly Gln Val Ser Ile
        355                 360                 365
Gly Asp Glu Asn Ser Ala Tyr Ser Ser Val Leu Tyr Lys Asp Asp Lys
        370                 375                 380
Leu Tyr Cys Leu His Glu Ile Asn Thr Asp Glu Val Tyr Ser Leu Val
385                 390                 395                 400
Phe Ala Arg Leu Val Gly Glu Leu Arg Ile Ile Lys Ser Val Leu Arg
                405                 410                 415
Ser Trp Lys Asn Trp Asp Ser His Leu Ser Ser Ile Cys Thr Pro Ala
                420                 425                 430
Asp Pro Ala Ala Ser Ser Glu Ser Gly Cys Gly Pro Ala Val Thr
                435                 440                 445
Thr Val Gly Leu Val Gly Phe Leu Ser Gly Asn Ala Ser Gln Asn Val
        450                 455                 460
Trp Glu Asp Ala Tyr Arg Cys Val Asn Ala Ser Thr Ala Asn Ala Glu
465                 470                 475                 480
Arg Val Arg Asn Gly Leu Lys Phe Ala Gly Val Gly Gly Ala Leu
                485                 490                 495
Trp Pro Val Ser Gln Gln Gly Gln Asn Gln Arg Tyr Arg Phe Ala Asn
                500                 505                 510
His Ala Phe Thr Leu Val Ala Ser Val Thr Ile His Glu Ala Pro Arg
        515                 520                 525
Ala Ala Ser Pro Leu Leu Gly Ala Ser Leu Asp Ser Ser Gly Gly Lys
        530                 535                 540
Lys Leu Leu Gly Leu Ser Tyr Asp Glu Lys His Gln Trp Gln Pro Ile
545                 550                 555                 560
Tyr Gly Ser Thr Pro Val Thr Pro Thr Gly Ser Trp Glu Thr Gly Lys
                565                 570                 575
Arg Tyr His Leu Val Leu Thr Met Ala Asn Lys Ile
                580                 585

<210> SEQ ID NO 6
<211> LENGTH: 1764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggggaaaa cagtcgttgt ggccagtagg atgttctggc taatgttttt cgtgccgctt      60
cttcttgcga tctgccccag cgagcccgcg tacgccttgg cacccggatc gagccgagtt     120 gagctgtttta agcgtaagaa ttcgacggtg ccgtttgaag acaaggccgg caaagtcacc     180
gagcgggttg tccactcgtt ccgcctcccc gcccttgtta atgtgacggg ggtgatggtt     240
gccatcgcgg acgtcgcta cgacacatcc aatgacaact ccctcattga tacggtggcg     300
aagtacagcg tggacgatgg ggagacgtgg gagacccaaa ttgccatcaa gaacagccgt     360
gtatcgtctg tttctcgtgt ggtggatccc accgtgattg tgaagggcaa caagctttac     420
gtcctggttg gaagctacta tagttcgaga agctactggt cgtcgcatgg tgatgcgaga     480
gactgggata ttctgcttgc cgttggtgag gtcacgaagt ccactgcggg cggcaagata     540
actgcgagta tcaaatgggg gagccccgtg tcactgaaga agtttttttcc ggcagaaatg     600 gaaggcatgc acacaaaatca atttcttggc ggcgcgggtg ttgccattgt agcgtccaac     660
```

```
gggaatcttg tgtaccctgt gcaggttacg aacaaaaaga agcaagtttt ctccaagatc    720
ttctactcgg aagatgatgg caagacgtgg aagtttggga agggtaggag cgattttggc    780
tgctctgaac ctgtggccct tgagtgggag gggaagctca tcataaacac ccgagttgac    840
tggaaacgcc gtctggtgta cgagtccagt gacatggaga aaccgtgggt ggaggctgtc    900
ggaaccgtct cgcgtgtgtg gggcccctca ccaaaatcga accagcccgg cagtcagagc    960
agcttcactg ccgtgaccat cgaaggaatg cgtgtgatgc tcttcacaca cccgctgaat   1020
tttaagggaa ggtggctgcg cgaccgactg aacctctggc tgacggataa ccagcgcatt   1080
tataacgttg ggcaagtatc cattggtgat gaaaattccg cctacagctc cgtcctgtac   1140
aaggatgata agctgtactg tttgcatgag atcaacacgg acgaggtgta cagccttgtt   1200
tttgcacgcc tggttggcga gctacggatc attaaatcag tgctgcggtc ctggaagaat   1260
tgggacagcc acctgtccag catttgcacc cctgctgatc cagccgcttc gtcgtcagag   1320
agtggttgtg gtcccgctgt caccacggtt ggtcttgttg cttttttgtc cggcaacgcc   1380
tcccaaaacg tatgggagga tgcgtaccgc tgcgtcaacg caagcacggc aaatgcggag   1440
agggttcgga acggtttgaa gtttgcgggg gttggcggag gagcgctttg gccggtgagc   1500
cagcaggggc agaatcagcg gtatcgtttt gcaaaccacg cgttcacgct ggtggcgtcg   1560
gtgacgattc acgaggctcc gagggccgcg agtcccttgc tgggtgcgag cctggactct   1620
tctggcggca aaaaactcct ggggctctcg tacgacgaga agcaccagtg gcagccaata   1680
tacggatcaa cgccggtgac gccgacggga tcgtgggaga cgggtaaaag gtaccacttg   1740
gttcttacga tggcgaataa aatt                                         1764

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctcttcctc caccactatg ca                                             22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctgagaca gcacgtggat                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcccgccgaa ttcctgcact                                                20
```

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caatggcacg cttgccgcag                                               20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatgagaaga agaggcacag ggct                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggcctggt ctaagtgctt gtca                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgacattgtg gcctttggaa ccat                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agatgtcagt gatgctcttg ggct                                          24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagcgtcgtg attagcgatg atg                                           23

<210> SEQ ID NO 16
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgagcaagtc tttcagtcct gtc                                              23
```

COMPOSITIONS AND METHODS FOR TREATING INFLAMMATORY DISEASES

CROSS REFERENCE TO RELATED APPLICATIONS

This application is the U.S. national phase application, pursuant to 35 U.S.C. §371, of PCT international application Ser. No. PCT/US2014/029323, filed Mar. 14, 2014, designating the United States and published in English, which claims priority to and the benefit of U.S. Provisional Application Nos. 61/784,814, filed Mar. 14, 2013 and 61/918,260, filed Dec. 19, 2013, respectively, which are incorporated herein by reference in their entireties.

STATEMENT OF RIGHTS TO INVENTIONS MADE UNDER FEDERALLY SPONSORED RESEARCH

This invention was made with government support under Grant Nos. NS040574, NS42960, and AI09738 awarded by the National Institutes of Health (NIH). The U.S. government has certain rights in the invention.

BACKGROUND OF THE INVENTION

Inflammation is a mechanism that protects mammals from invading pathogens and other insults, whether from the environment or from inside the body. However, while transient inflammation is necessary to protect a mammal from infection, uncontrolled inflammation causes tissue damage and is the underlying cause of many illnesses.

Several types of cardiomyopathies are characterized by excessive tissue-destroying inflammation and fibrosis that leads to cardiac failure and sudden death. Heart failure is a major economic burden worldwide, estimated to cost per year about $34.4 billion. Orthotopic heart transplant is the only available cure but it is not practical because of the relative absence of donor hearts. Hence, identifying regenerative strategies for heart failure is a most urgent clinical need.

Because current methods for treating or preventing inflammation are inadequate, compositions and methods for treating or preventing inflammation are urgently required. Such compositions and methods are useful for the prevention and/or treatment of inflammatory diseases and disorders (e.g., in heart, liver, and gastrointestinal tract).

SUMMARY OF THE INVENTION

As described below, the present invention features compositions comprising PDNF, or a fragment thereof, that provide for the prevention and/or treatment of inflammatory conditions in non-neuronal tissues (e.g., heart, liver, and gastrointestinal tract). The invention also provides compositions featuring PDNF, or a fragment thereof, and methods for using such compositions for the proliferation and/or mobilization of a stem cell (e.g., cardiac stem cell) or progenitor cell (e.g., hepatic progenitor cell).

In one aspect, the invention provides a method of decreasing inflammation in a non-neuronal tissue of a subject, involving administering to the subject soluble parasite-derived neurotrophic factor (sPDNF), or fragment thereof, in an amount effective to decrease inflammation in the non-neuronal tissue.

In another aspect, the invention provides a method of decreasing inflammation in a cardiac, liver, pancreas, or gastrointestinal tissue of a subject, involving administering to the subject soluble parasite-derived neurotrophic factor (sPDNF), or a fragment thereof, in an amount effective to decrease inflammation in the cardiac, liver, pancreatic, or gastrointestinal tissue.

In still another aspect, the invention provides a method of increasing expression of an anti-inflammatory factor in a non-neuronal cell or tissue, involving contacting the non-neuronal cell or tissue with soluble parasite-derived neurotrophic factor (sPDNF), or a fragment thereof, in an amount effective to increase expression of an anti-inflammatory factor in the non-neuronal cell or tissue.

In one aspect, the invention provides a method of increasing stem cell number, involving contacting a non-neuronal cell or tissue with soluble parasite-derived neurotrophic factor (sPDNF), or fragment thereof.

In another aspect, the invention provides a method of increasing stem cell mobilization, involving contacting a non-neuronal cell or tissue with soluble parasite-derived neurotrophic factor (sPDNF), or fragment thereof.

In yet another aspect, the invention provides a method of increasing stem cell proliferation, involving contacting a non-neuronal cell or tissue with soluble parasite-derived neurotrophic factor (sPDNF), or fragment thereof.

In one aspect, the invention provides a method of treating or preventing a cardiac inflammatory disease in a subject in need thereof, involving administering to the subject a therapeutically effective amount of soluble parasite-derived neurotrophic factor (sPDNF), or fragment thereof.

In another aspect, the invention provides a method of treating or preventing a hepatic inflammatory disease in a subject in need thereof, involving administering to the subject a therapeutically effective amount of soluble parasite-derived neurotrophic factor (sPDNF), or fragment thereof.

In still another aspect, the invention provides a method of treating or preventing a pancreatic inflammatory disease in a subject in need thereof, involving administering to the subject a therapeutically effective amount of soluble parasite-derived neurotrophic factor (sPDNF), or fragment thereof.

In yet another aspect, the invention provides a method of treating or preventing an inflammatory disease of the gastrointestinal (GI) tract in a subject in need thereof, involving administering to the subject a therapeutically effective amount of soluble parasite-derived neurotrophic factor (sPDNF), or fragment thereof.

In various embodiments of any aspect delineated herein, sPDNF, or fragment of sPDNF, has at least 85%, 90%, 95%, or 99% identity to the amino acid sequence set forth in residues 1-588 of SEQ ID NO: 2. In various embodiments of any aspect delineated herein, sPDNF, or fragment of sPDNF, comprises an amino acid sequence that is selected from the group consisting of: (a) the amino acid sequence set forth in residues 33-666 of SEQ ID NO: 2; (b) the amino acid sequence set forth in residues 1 to 596 of SEQ ID NO: 4; and (c) an amino acid sequence that is at least 85% identical to any one of (a) or (b).

In various embodiments of any aspect delineated herein, where the non-neuronal cell or tissue is in vivo or ex vivo. In various embodiments of any aspect delineated herein, the non-neuronal cell or is a cardiac, hepatic, pancreatic, and/or gastrointestinal cell or tissue. In various embodiments, the anti-inflammatory factor is one or more of IL1-Ra, TSG-6 and COX-2. In various embodiments of any aspect delineated herein, the stem cell is in vivo or ex vivo. In various embodiments, the stem cell expresses Sca-1 and/or c-Kit. In particular embodiments, the stem cell is a cardiac, hepatic, pancreatic, and/or gastrointestinal stem cell.

In various embodiments of any aspect delineated herein, the non-neuronal cell or tissue is in a subject. In various embodiments of any aspect delineated herein, the subject (e.g., human subject) has or is at risk of having an inflammatory disease. In various embodiments, the inflammatory disease is a cardiac inflammatory disease, hepatic inflammatory disease, pancreatic inflammatory disease, and/or inflammatory disease of the gastrointestinal (GI) tract. In particular embodiments, the cardiac inflammatory disease is myocarditis, cardiomyopathy, endocarditis, and/or pericarditis. In particular embodiments, the hepatic inflammatory disease is hepatitis and/or cirrhosis. In particular embodiments, the pancreatic inflammatory disease of is type 1 or type 2 diabetes. In particular embodiments, the inflammatory disease of the GI tract is inflammatory bowel disease (IBD), irritable bowel syndrome, ileitis, chronic inflammatory intestinal disease, celiac disease, Crohn's disease, and/or ulcerative colitis. In various embodiments of any aspect delineated herein, the subject does not have Chagas disease.

In various embodiments of any aspect delineated herein, sPDNF, or fragment thereof, is administered parenterally, intraperitoneally, sub-cutaneously, or intravenously. In various embodiments of any aspect delineated herein, the method further involves administering an anti-inflammatory agent.

Compositions and articles defined by the invention were isolated or otherwise manufactured in connection with the examples provided below. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "anti-inflammatory" is meant an agent that reduces the severity or symptoms of an inflammatory reaction in a tissue. An inflammatory reaction within tissue is generally characterized by leukocyte infiltration, edema, redness, pain, and/or neovascularization. Inflammation can also be measured by analyzing levels of cytokines or any other inflammatory marker.

The term "anti-inflammatory amount" as used herein means the amount which reduces, alleviates, or inhibits inflammation in the tissue or body.

By "decreases" is meant a negative alteration of at least 10%, 25%, 50%, 75%, 100%, or more.

"Detect" refers to identifying the presence, absence or amount of the analyte to be detected.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "increases" is meant a positive alteration of at least 10%, 25%, 50%, 75%, 100%, or more.

As used herein, the phrase "inflammatory disease" or "inflammatory disorder" disorder" includes any disease, disorder, or condition that is caused by or related to an inflammatory process within one or more tissue or serum of the body of a mammal. In certain embodiments, the inflammatory disease is mediated by the interleukin-1 (IL-1) receptor. In particular embodiments, the inflammatory disease or disorder is in a non-neuronal tissue, including but not limited to atherosclerosis, diabetes (e.g., diabetes Type 1 and 2), arthritis, cardiovascular disease, and organ damage, such as liver damage for example.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "hybridize" is meant pair to form a double-stranded molecule between complementary polynucleotide sequences (e.g., genes listed in Tables 1 and 2), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "marker" is meant any protein or polynucleotide having an alteration in expression level or activity that is associated with a disease or disorder.

By "neuronal" is meant any cell or tissue that includes neurons and neural cells related to the nervous system, including glial cells and schwann cells By "non-neuronal" is meant any cell or tissue excluding neuronal cells or tissues (e.g., neurons and cells related to the nervous system). related to the nervous system. In particular embodiments a non-neuronal cell or tissue includes, for example, cardiac, hepatic, pancreatic, and gastrointestinal cells and tissues.

By "parasite-derived neurotrophic factor (PDNF) polypeptide" is meant a polypeptide or fragment thereof having at least about 85%, 90%, 95%, 96%, 97%, 98%, or 99% amino acid identity to NCBI Accession No. NP_001387 and that specifically binds a Trk receptor (e.g., TrkA, TrkC). Exemplary PDNF polypeptide sequences are provided at FIG. 1.

By "soluble parasite-derived neurotrophic factor (sPDNF) polypeptide" is meant a polypeptide or fragment thereof having at least about 85%, 90%, 95%, 96%, 97%, 98%, or 99% amino acid identity to the sequence provided below and that specifically binds a Trk receptor (e.g., TrkA, TrkC). JR-100 is the commercial name for sPDNF.

```
                                          (amino acids 1-588 of SEQ ID NO: 2)
  1 MGKTVVVASRMFWLMFFVPLLLLAICPSEPAYALAPGSSRVELFKRKNSTVPFEDKAGKVT

61 ERVVHSFRLPALVNVDGVMVAIADARYDTSNDNSLIDTVAKYSVDDGETWETQIAIKNSR

121 VSSVSRVVDPTVIVKGNKLYVLVGSYYSSRSYWSSHGDARDWDILLAVGEVTKSTAGGKI

181 TASIKWGSPVSLKKFFPAEMEGMHTNQFLGGAGVAIVASNGNLVYPVQVTNKKKQVFSKI

241 FYSEDDGKTWKFGKGRSDFGCSEPVALEWEGKLIINTRVDWKRRLVYESSDMEKPWVEAV

301 GTVSRVWGPSPKSNQPGSQSSFTAVTIEGMRVMLFTHPLNFKGRWLRDRLNLWLTDNQRI

361 YNVGQVSIGDENSAYSSVLYKDDKLYCLHEINTDEVYSLVFARLVGELRIIKSVLRSWKN

421 WDSHLSSICTPADPAASSSESGCGPAVTTVGLVGFLSGNASQNVWEDAYRCVNASTANAE

481 RVRNGLKFAGVGGGALWPVSQQGQNQRYRFANHAFTLVASVTIHEAPRAASPLLGASLDS

541 SGGKKLLGLSYDEKHQWQPIYGSTPVTPTGSWETGKRYHLVLTMANKI
```

By "parasite-derived neurotrophic factor (PDNF) nucleic acid molecule" is meant a polynucleotide encoding a parasite-derived neurotrophic factor polypeptide or fragment thereof. Exemplary PDNF nucleic acid sequences are provided at FIG. 1.

By "soluble parasite-derived neurotrophic factor (sPDNF) nucleic acid molecule" is meant a polynucleotide encoding a soluble parasite-derived neurotrophic factor polypeptide or fragment thereof.

```
                    (nucleotides 136-1899 of SEQ ID NO: 1)
   1 atggggaaaacagtcgttgtggccagtaggatgttctggctaatgttttcgtgccgctt 61 cttcttgcgatctgcccagcgagcccgcgtacgccttggcacccggatcgagccgagtt 121 gagctgtttaagcgtaagaattcgacggtgccgtttgaagacaaggccggcaaagtcacc 181 gagcgggttgtccactcgttccgcctccccgcccttgttaatgtggacggggtgatggtt 241 gccatcgcggacgctcgctacgacacatccaatgacaactccctcattgatacggtggcg 301 aagtacagcgtggacgatggggagacgtgggagacccaaattgccatcaagaacagccgt 361 gtatcgtctgtttctcgtgtggtggatcccaccgtgattgtgaagggcaacaagctttac 421 gtcctggttggaagctactatagttcgagaagctactggtcgtcgcatggtgatgcgaga 481 gactgggatattctgcttgccgttggtgaggtcacgaagtccactgcgggcggcaagata 541 actgcgagtatcaaatgggggagccccgtgtcactgaagaagttttttccggcagaaatg 601 gaaggcatgcacacaaatcaatttcttggcggcgcgggtgttgccattgtagcgtccaac 661 gggaatcttgtgtaccctgtgcaggttacgaacaaaaagaagcaagttttctccaagatc 721 ttctactcggaagatgatggcaagacgtggaagtttgggaagggtaggagcgattttggc 781 tgctctgaacctgtggcccttgagtgggaggggaagctcatcataaacacccgagttgac 841 tggaaacgccgtctggtgtacgagtccagtgacatggagaaaccgtgggtggaggctgtc 901 ggaaccgtctcgcgtgtgtggggcccctcaccaaaatcgaaccagcccggcagtcagagc 961 agcttcactgccgtgaccatcgaaggaatgcgtgtgatgctcttcacacacccgctgaat 1021 tttaagggaaggtggctgcgcgaccgactgaacctctggctgacggataaccagcgcatt 1081 tataacgtgggcaagtatccattggtgatgaaaattccgcctacagctccgtcctgtac 1141 aaggatgataagctgtactgtttgcatgagatcaacacggacgaggtgtacagccttgtt 1201 tttgcacgcctggttggcgagctacggatcattaaatcagtgctgcggtcctggaagaat 1261 tgggacagccacctgtccagcatttgcacccctgctgatccagccgcttcgtcgtcagag 1321 agtggttgtggtcccgctgtcaccacggttggtcttgttggcttttttgtccggcaacgcc 1381 tcccaaaacgtatgggaggatgcgtaccgctgcgtcaacgcaagcacggcaaatgcggag 1441 agggttcggaacggtttgaagtttgcggggggttggcggaggagcgctttggccggtgagc 1501 cagcaggggcagaatcagcggtatcgttttgcaaaccacgcgttcacgctggtggcgtcg 1561 gtgacgattcacgaggctccgagggccgcgagtcccttgctgggtgcgagcctggactct 1621 tctggcggcaaaaaactcctggggctctcgtacgacgagaagcaccagtggcagccaata 1681 tacggatcaacgccggtgacgccgacgggatcgtgggagacgggtaaaaggtaccacttg 1741 gttcttacgatggcgaataaaatt
```

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

A "reference sequence" is a defined sequence used as a basis for sequence comparison.

By "small molecule" is meant any chemical compound.

By "specifically binds" is meant a compound or agent (e.g., PDNF) that recognizes and binds a polypeptide of the invention (e.g., TrkA, TrkC), but which does not substantially recognize and bind other molecules in a sample.

By "subject" is meant a mammal, including, but not limited to, a human or non-human mammal, such as a bovine, equine, canine, ovine, or feline.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

Unless specifically stated or obvious from context, as used herein, the term "or" is understood to be inclusive. Unless specifically stated or obvious from context, as used herein, the terms "a", "an", and "the" are understood to be singular or plural. Thus, for example, reference to "an amino acid substitution" includes reference to more than one amino acid substitution.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other features and advantages of the invention will be apparent from the following description of the desirable embodiments thereof, and from the claims.

BRIEF DESCRIPTION OF THE DRAWINGS

FIG. 1 provides the nucleotide and amino acid sequences of exemplary PDNFs.

FIG. 1A illustrates the nucleotide sequence of the PDNF gene, clone 19Y (SEQ ID NO:1) deposited in GenBank under accession number AJ002174, having an open-reading frame beginning at position 370. FIG. 1B illustrates the amino acid sequence of the PDNF (SEQ ID NO:2) encoded by clone 19Y deposited in GenBank under accession number AJ002174. FIG. 1C illustrates the nucleotide sequence of the PDNF gene, clone 7F (SEQ ID NO:3) deposited in GenBank under accession number M61732, having an open-reading frame beginning at position 484. FIG. 1D illustrates the amino acid sequence of the PDNF (SEQ ID NO:4) encoded by clone 7F deposited in GenBank under accession number M61732. The PDNF comprises a catalytic domain (amino acid residues 33-666 of SEQ ID NO:4), and a tandem repeat domain (amino acid residues 667-1162 or SEQ ID NO:4).

FIG. 2A is a graph showing stem cell marker expression in mice administered sPDNF. One set of three wild type C57BL/6 mice received intravenous (IV) PBS without (PBS) or with sPDNF (2 mg/kg) at 0, 3 and 24 hours (sPDNF 1d), and a second set IV sPDNF (2 mg/kg) for 6 days (sPDNF 6d). Mice were sacrificed 3 hr post injection and the indicated stem cells markers were quantified in the ventricles by real time PCR, and normalized to HPRT; *, $p<0.05$, , $p<0.001$, *, $p<0.0001$; SCF, stem cell factor, ns, not significant. FIG. 2B is a graph showing stem cell marker expression in MyD88$^{-/-}$ mice administered sPDNF. TLR-deficient MyD88$^{-/-}$ mice (C57BL/6 background) (2/group) were injected IV with a single dose of sPDNF (2 mg/kg), sacrificed at 3 hours post-injection, and the indicated cardiac stem cell markers assessed by qPCR. Data were normalized to HPRT and made relative to vehicle-treated controls (set at 1.0 and represented by the dashed line); , $P<0.01$; and *, $P<0.005$. FIG. 2C is a graph showing stem cell marker expression in mice administered sPDNF at various time points after injection. C57BL/6 mice (5 per group) were injected IV with PBS or sPDNF (3 mg/kg body weight), and sacrificed at 0, 1, 3 and 7 hours later. Cardiac Sca-1 and SCF transcripts were quantified by qPCR; , $P<0.001$; *, $P<0.0005$. FIG. 2D is a graph showing quantitation of Sca-1 expression in various organs of mice administered sPDNF. C57BL/6 mice (3 per group), average of two experiments) were injected IV with sPDNF at 4 mg/kg body weight or PBS, sacrificed 3 hours later, and Sca-1 mRNA quantified by qPCR in the liver, heart, colon and bone marrow (*, $P<0.05$, , $P<0.001$; ns, not significant; dotted line represents Sca-1 mRNA of vehicle-treated mice set at 1.0, data are representative of 2 experiments. FIG. 2E are images of heart tissue samples with staining for Sca-1 from mice injected with vehicle (left image) or PDNF (right image). C57BL/6 mice (2 per group) were injected IV three times (0, 3, and 24 h) with PBS (IV Vehicle) or 2 mg/kg sPDNF (IV sPDNF), and sacrificed 48 hours after the first injection. Heart (ventricle) was fixed in paraformaldehyde, and tissue sections stained with a rabbit antibody against Sca-1 and DAPI. Normal rabbit IgG did not stain cardiac cells. Graph insert shows the percentage of Sca-1$^+$ cells per field determined by dividing the number of Sca-1+ cells by the total number of cells (i.e., DAPI+ nuclei) per field, in 12-14 random fields from 3 tissue sections per condition; *, $P<0.001$; two experiments, similar results. FIG. 2F is a graph showing quantitation of expression of inflammatory markers in mice administered sPDNF. Wild type and naïve mice (5 per group) were injected IV with a single dose of sPDNF (4 mg/kg), sacrificed 3 hr post-injection, and the L-1Ra, TSG-6, COX-2, and IDO transcripts quantified in the heart and liver. Data are combined from two separate experiments; ***, $P<0.001$.

FIG. 3A depicts in vivo experimental design, groups, treatment and timeline for the infective and anti-inflammatory effects of sPDNF. C57BL/6 mice (7 per group) were injected intraperitoneally with T cruzi Colombian strain ($8\times10^2$ per mouse) and, four months later, intravenously with PBS (vehicle) or sPDNF (1 mg/kg body weight) at 0, 3, and 24 hours, weekly for 3 weeks. Mice were sacrificed 50 days after the first set of IV sPDNF treatment. FIG. 3B are images of heart (ventricle) paraffin-embedded, sectioned, and stained with H&E. Arrows indicate foci of inflammatory infiltrates, which were abundant in sham-treated (IV PBS) CCC mice and rare in IV sPDNF-treated CCC mice. Similar histology was found in other tissue sections and in a distinct set of sPDNF-treated and PBS-sham mice.

FIGS. 4A and 4B display sections of atria of mice with CCC administered IV PBS or IV sPDNF, respectively. FIG. 4C is a graph showing the amount of cardiac fibrosis, as determined using ImageJ software (NIH) in four distinct sections of atria and ventricles. Relative cardiac fibrosis is defined as the ratio of blue pixels to total pixels (blue+red) normalized to corresponding areas of the heart of uninfected mice set at 1.0 (dotted line); **, $P<0.01$, ns, not significant relative uninfected hearts.

FIG. 5A is a graph showing transcript expression for inflammatory cytokines in hearts of the infected mice, as assessed by qPCR for the indicated transcripts, which were normalized to HPRT and made relative to uninfected vehicle-treated mice. Values for IFN-λ were reduced by 3-fold; , $p<0.01$. FIG. 5B is a graph showing transcript expression for inflammatory cell markers in hearts of the infected mice, as assessed by qPCR for the indicated transcripts, which were normalized to HPRT and made relative to uninfected vehicle-treated mice. Values for CD8, and CD4 were reduced by 15-, and 1.5-fold, respectively; , $p<0.01$, ***, $p<0.001$. FIG. 5C is a graph showing transcript expression for inflammatory cytokines in hearts of the infected mice, as assessed by qPCR for the indicated transcripts, which were normalized to HPRT and made relative to uninfected vehicle-treated mice. FIG. 5D is a graph showing percent reduction of cardiac inflammatory markers of mice chronically infected with *T cruzi*, using data from FIGS. 5A-5C. Baseline represents mean transcripts of uninfected mice. FIG. 5E is a graph showing expression of TSG-6 transcripts in heart and liver of *T cruzi* infected mice. Heart (ventricles+atria) and liver of mice (5 per group) infected acutely (25-day post injection) (Acute) or chronically (6-months PI, CCC, same as in FIG. 3) with *T cruzi* Colombian were assessed for TSG-6 transcript by qPCR and plotted relative to uninfected mice set at 1.0; , $P<0.001$. Note that TSG-6 mRNA is increased in the heart and liver of acute, but no chronic, infected, and that IV sPDNF in chronically infected mice restored TSG-6 transcript to levels seen in acutely infected mice.

FIG. 7A is a graph depicting MCP-1 and FKN expression in cardiomyocytes of mice infected with *T cruzi*. FIG. 7B is a graph depicting MCP-1 and FKN expression in cardiac fibroblasts of mice infected with *T cruzi*. *T cruzi* infection: Primary cultures of mouse cardiomyocytes (FIG. 7A) and cardiac fibroblasts (FIG. 7B) were plated in 6-well plates, infected with *T cruzi* Tulahuen strain (MOI=10) for 3, 24, and 72 hr, and MCP-1 and FKN transcripts were quantified by qPCR. Chemokine gene expression was normalized to HPRT and fold change calculated relative to uninfected cells. Points represent mean±SD fold change expression of triplicate samples. The experiment was repeated, and similar results were obtained. FIG. 7C is a graph depicting MCP-1 and FKN expression in cardiomyocytes of mice injected with sPDNF. FIG. 7D is a graph depicting MCP-1 and FKN expression in cardiac fibroblasts of mice injected with sPDNF. sPDNF stimulation: Primary cardiomyocytes (FIG. 7C) and cardiac fibroblasts (FIG. 7D) were plated in 6-well plates, serum starved overnight, then stimulated with the indicated concentration of sPDNF (3 hr), and MCP-1 and FKN transcripts were quantified by qPCR. Chemokine gene expression was normalized to HPRT and fold change calculated relative to vehicle-treated cells; *$P<0.05$, $P<0.01$, and *$P<0.005$.

FIG. 8A is a graph showing dose-response of MCP-1 secretion to sPDNF stimulation. H9c2 cardiomyocytes were plated in 6-well plates, grown in low serum (0.1% FCS) overnight, and stimulated with the indicated doses of sPDNF for 3 hr. Secretion of MCP-1, MIP-2α and IL-6 was determined by ELISA. FIG. 8B is a graph showing dose-response of MCP-transcript expression. H9c2 cardiomyocytes were plated in 6-well plates, grown in low serum (0.1%) overnight, and stimulated with the indicated doses of sPDNF for 3 hr, and MCP-transcript quantified by qPCR. Chemokine gene expression was normalized to HPRT and fold change calculated relative to vehicle-treated cells. Points represent mean±SD fold change expression of triplicate samples; *$P<0.05$, $P<0.01$, and *$P<0.005$. FIG. 8C is a graph showing time course of MCP-1 and FKN transcripts expression. H9c2 cardiomyocytes were plated in 6-well plates (triplicate), grown in low serum (0.1%) overnight, stimulated with sPDNF (1 µg/ml) for the indicated times, and MCP-1 and FKN (data not shown) transcripts quantified by qPCR. Three experiments gave similar results.

FIG. 9A is a graph showing the effect of the Trk antagonist, K252a, on MCP-1 transcript expression in cardiomyocytes treated with sPDNF. FIG. 9B is a graph showing the effect of the Trk antagonist, K252a, on FKN transcript expression in cardiomyocytes treated with sPDNF. Pharmacological inhibition: H9c2 cardiomyocytes were stimulated with sPDNF (1 µg/ml, 3 hr) without pretreatment (sPDNF) or after pretreatment with K252a (200 nM, 1 hr) (K252a+sPDNF), and transcripts of MCP-1 (FIG. 9A) and FKN (FIG. 9B) quantified by qPCR. Chemokine gene expression was normalized to HPRT and fold change calculated relative to vehicle-treated cells. Bars represent mean±SD fold change expression of duplicate samples, *$P<0.05$ and **$P<0.01$; experiment performed three times, each giving similar results. FIG. 9C is a graph showing the effect of Trk neutralizing antibodies on MCP-1 transcript expression in cardiomyocytes treated with sPDNF. FIG. 9D is a graph showing the effect of Trk neutralizing antibodies on FKN transcript expression in cardiomyocytes treated with sPDNF. Neutralizing antibodies: H9c2 cardiomyocytes were stimulated with sPDNF (1 µg/ml, 3 hr) without pretreatment (+sPDNF) or after pretreatment with neutralizing antibodies (1 µg/ml, 30 min) against TrkA (α-TrkA+sPDNF), TrkB (α-TrkB+sPDNF), and TrkC (α-TrkC+sPDNF) followed by sPDNF), and transcripts of MCP-1 (FIG. 9C) and FKN (FIG. 9D) quantified by qPCR. Chemokine gene expression was normalized to HPRT and fold change calculated relative to vehicle-treated cells. Bars represent mean±SD fold change expression of duplicate samples, *P<0.05 and **P<0.01, ns=not significant. FIG. 9E is a graph showing the effect of TrkA and TrkC RNA silencing on MCP-1 secretion in cardiomyocytes treated with sPDNF. RNA silencing: H9c2 cardiomyocytes were transfected with lentiviral particles containing shRNAs targeting GFP (control), TrkA (clones 1-4) and TrkC (clones 1-5). After 7-8 d, cells were serum starved (2 hr) and stimulated with vehicle or sPDNF (4 µg/ml, 3 hr), and the concentration of MCP-1 secreted in the supernatants was determined by ELISA; ns=not significant, *P<0.05, P<0.01, and *P<0.005 (relative to shGFP transfected cells).

FIG. 10A is a graph showing the kinetics of cardiac MCP-1 mRNA in response to acute $T.$ $cruzi$ infection in relation to heart parasite burden. FIG. 10B is a graph showing the kinetics of cardiac MCP-1 and FKN mRNA in response to acute $T.$ $cruzi$ infection in relation to heart parasite burden. Groups of C57BL/6 mice (3 per group) were subcutaneously infected with $T$ $cruzi$, and, at the indicated timepoints, mice were sacrificed and MCP-1, FKN and parasite burden quantified in their heart (ventricles+ atria) by qPCR.

FIG. 11A is a graph depicting that a single dose of intravenous (IV) sPDNF increased MCP-1 and FKN transcripts in the heart in a pulse-like response. Groups of mice (2 per group) were injected with vehicle (Veh) or sPDNF (150 µg/mouse) and sacrificed at 3, 6, 9 and 12 hr post-injection, and cardiac MCP-1 and FKN transcripts were quantified by qPCR. Points represent fold change of the mean±SD relative to Veh injected mice; *P<0.05 and P<0.01. Experiment repeated three times with similar results; liver also responded with similar pulselike kinetics. FIG. 11B is a graph depicting that organ distribution of MCP-1 increased following a single IV dose of sPDNF. Experimental design analogous to that summarized above. FIG. 11C is a graph showing that a single IV dose of sPDNF augments MCP-1 and FKN transcripts dose-dependently in the heart. FIG. 11D is a graph showing that a single IV dose of sPDNF augments MCP-1 and FKN transcripts dose-dependently in the liver. For the results depicted in FIGS. 11C and 11D, groups of three mice were injected with various doses of sPDNF, and heart and liver harvested 3 hr post-injection to quantify MCP-1 and FKN by qPCR. The results are plotted as a composite of three distinct experiments. The increase in hepatic FKN mRNA was not statistically significant; * P<0.005. For the results depicted in FIGS. 11E-11H, TLR-deficient MyD88$^{-/-}$ mice (two per group) were injected IV with vehicle (PBS) or sPDNF (100 µg per mouse), sacrificed 3 hr post-injection. FIG. 11E is a graph showing MCP-1 expression in the heart of MyD88$^{-/-}$ mice injected with sPDNF. FIG. 11F is a graph showing FKN expression in the heart of MyD88$^{-/-}$ mice injected with sPDNF. FIG. 11G is a graph showing MCP-1 expression in the liver of MyD88$^{-/-}$ mice injected with sPDNF. FIG. 11H is a graph showing FKN expression in the liver of MyD88$^{-/-}$ mice injected with sPDNF.

FIG. 12A is a graph showing the mRNA expression of MCP-1 receptor CCR2, as quantified by qPCR in the heart and liver. FIG. 12B is a graph showing the mRNA expression of FKN receptor CX3CR1, as quantified by qPCR in the heart and liver. Note that receptor transcripts did not increase following a single dose of IV sPDNF at 3 hr post-injection and 24 hr post-injection. For the results depicted in FIGS. 12C and 12D, mice (3/group) were injected with vehicle (Veh) or multiple doses of IV sPDNF (25 µg per injection) at 0, 3 and 24 hr, and sacrificed 24 hr after the last injection. FIG. 12C is a graph showing mRNA expression of CCR2, as quantified by qPCR in the liver, colon and heart (ventricles and atria). FIG. 12D is a graph showing mRNA expression of CX3CR1, as quantified by qPCR in the liver, colon and heart (ventricles and atria). Notice a statistically significant upregulation of MCP-1 and FKN receptors in the heart and liver 48-h after the start of three doses of IV sPDNF spaced within a 24 h span; *P<0.05, and ** P<0.01

DETAILED DESCRIPTION OF THE INVENTION

Figure 2A:
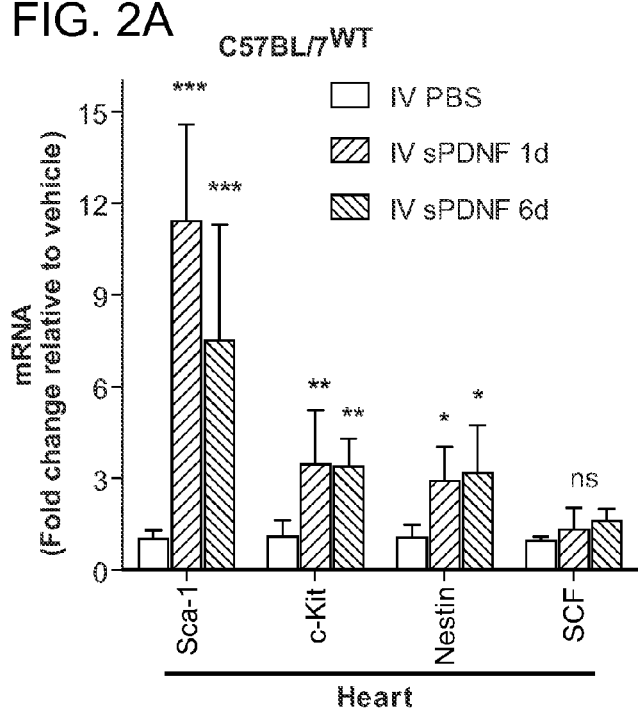
FIGS. 2A-2F show that intravenous administration of soluble PDNF (sPDNF) into naïve mice increased expression of cardiac and hepatic stem cell markers independent of TLR signaling, expanded cardiac Sca-1$^+$ cells, and increased expression of IL1-Ra, TSG-6 and COX-2.
Figure 2B:
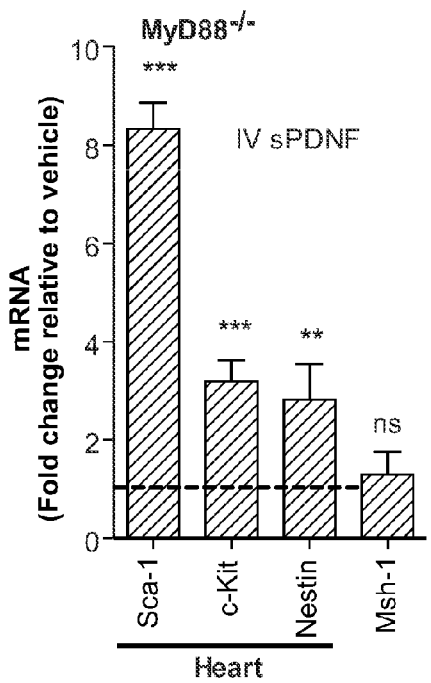
Figure 2C:
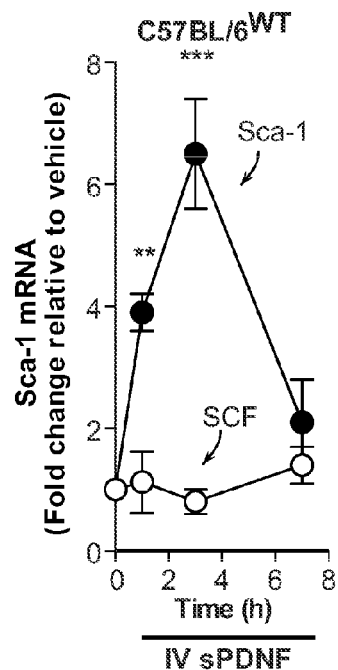
Figure 2D:
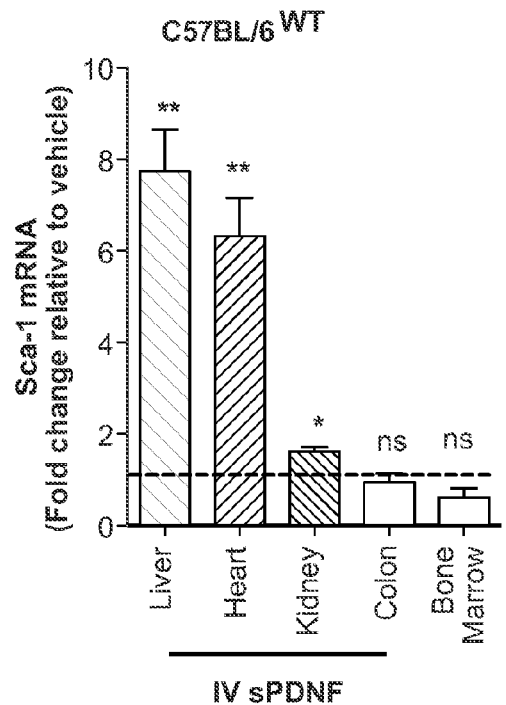
Figure 2E:
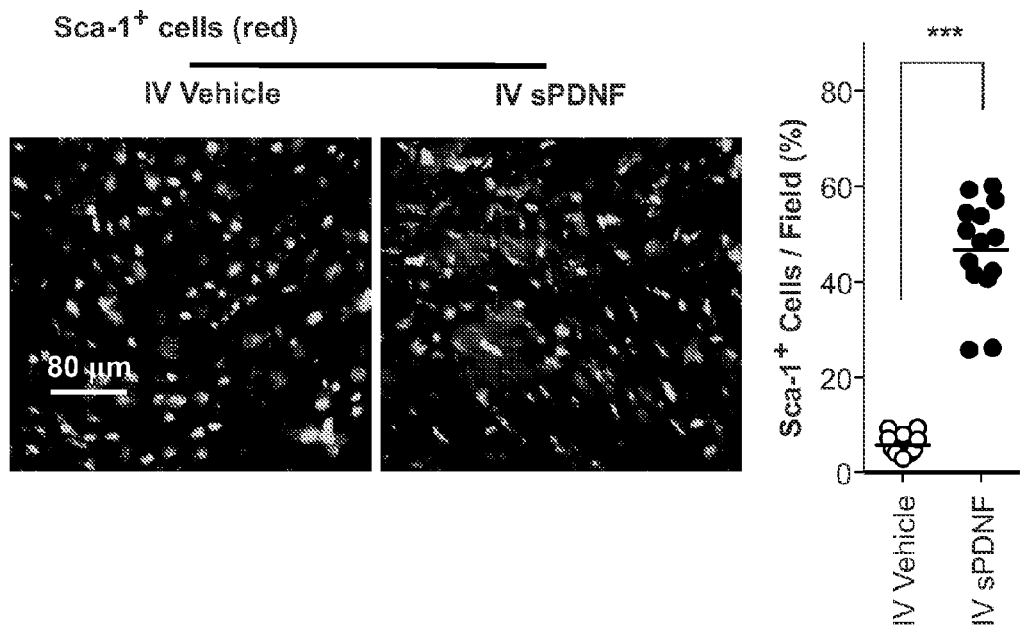
Figure 2F:
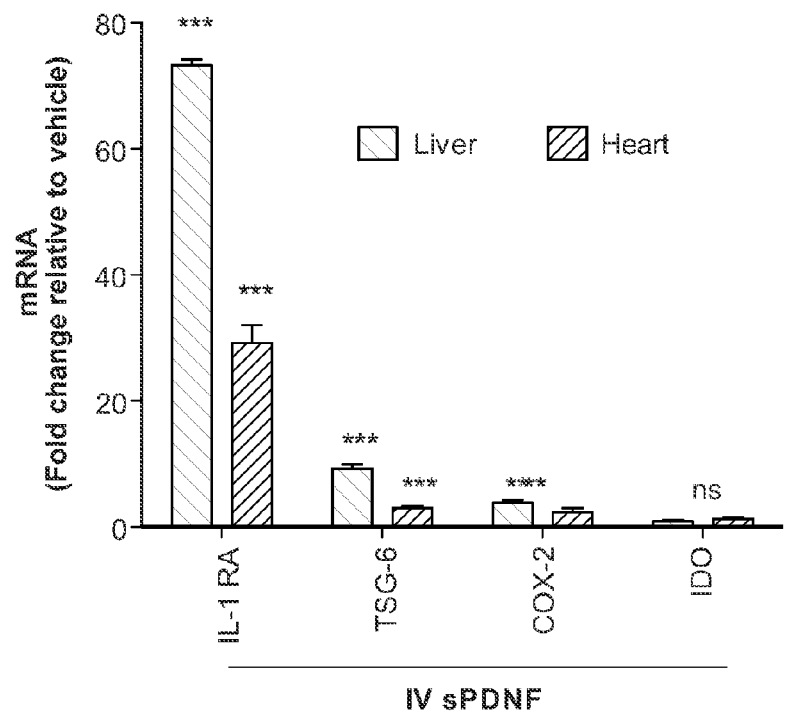

The invention features compositions and methods for treating inflammatory diseases or disorders, such as cardiac or hepatic inflammatory diseases, using parasite-derived neurotrophic factor (PDNF), or a fragment of PDNF that binds to the TrkA and/or TrkC Receptor. The compositions and methods are used to treat, for example, myocarditis, cardiomyopathy, endocarditis, pericarditis, Chagas disease, or hepatitis. The methods may also be used to treat an inflammatory disease of the gastrointestinal (GI) tract, pancreas, or a liver disease.

As reported in detail below, the invention is based in part on the discovery that PDNF can promote the regeneration of cardiac tissue, as well as reduce the inflammation of cardiac tissue. In particular, as disclosed and exemplified herein, the inventor discovered that administration of a PDNF polypeptide promoted both the proliferation and the mobilization of stem cells to non-neuronal tissues (e.g., heart, liver, pancreas, gastrointestinal tract, etc.).

Parasite-Derived Neurotrophic Factor (PDNF)

The human parasite $Trypanosoma$ $cruzi$, the agent of Chagas disease, expresses a membrane-bound neuraminidase, also known as trans-sialidase (TS), or parasite-derived neurotrophic factor (PDNF) because it binds and activates nerve growth factor (NGF) receptor TrkA in neuronal cells.

PDNF is an enzyme expressed on the $T.$ $cruzi$'s surface and catalyzes the transfer of sialic acid from host glycoconjugates to glycoprotein molecules on the surface of the parasite. See, Schenkman et al., Exp. Parasitol., 72:76 86 (1991). The enzyme is present both in the epimastigote form (i.e., in the invertebrate vector) and in the trypomastigote form (i.e., infectious form that circulates in the blood of the vertebrate host). See, Agusti et al., Glycobiology, 7(6):731 5, (1997).

FIG. 1 shows the nucleotide sequences and amino acid sequences of two naturally-occurring PDNFs. FIG. 1A illustrates the nucleotide sequence of the $T.$ $cruzi$ PDNF gene, clone 19Y (SEQ ID NO: 1), deposited in GenBank under accession number AJ002174, having an open-reading frame beginning at position 370. FIG. 1B illustrates the amino acid sequence of the *T. cruzi* PDNF (SEQ ID NO: 2) encoded by clone 19Y deposited in GenBank under accession number AJ002174. FIG. 1C illustrates the nucleotide sequence of the *T. cruzi* PDNF gene, clone 7F (SEQ ID NO: 3) deposited in GenBank under accession number M61732, having an open-reading frame beginning at position 484. FIG. 1D illustrates the amino acid sequence of the *T. cruzi* PDNF (SEQ ID NO: 4) encoded by clone 7F deposited in GenBank under accession number M61732. The entire teachings of the information deposited in GenBank under accession numbers AJ002174 and M61732 are incorporated herein by reference.

The naturally-occurring, full-length PDNF from *T. cruzi* trypomastigotes has 4 distinct amino acid regions: (1) a N-terminal region with approximately 380 amino acids, which shares about 30% sequence identity to bacterial sialidases; (2) a region with approximately 150 residues that does not show any similarity with any known sequence; (3) a region with homology to type III fibronectin (FnIII); and (4) a C-terminal region containing 12 repeated amino acids, which is the immuno-dominant portion and which is required for enzyme oligomerization. The N-terminal and the FnIII regions are important for trans-sialidase activity.

The catalytic portion of a native trans-sialidase has two kinds of enzymatic activities: (1) neuraminidase activity, which releases sialic acid from the complex carbohydrates; and (2) sialil-transferase activity, which catalyzes the transfer of sialic acid from glyconjugate donors to terminal β-D galactose containing acceptors. See, Scudder et al., J. Biol. Chem., 268(13):9886 91 (1993). Residues 33-666 of SEQ ID NO: 2 correspond to the catalytic domain of clone 19Y. Amino acid residues 1 to 596 of SEQ ID NO:4 encompass the catalytic domain of clone 7F.

The full-length native trans-sialidase also has a long 12-amino acid tandem repeat domain in the C-terminus, previously identified as SAPA (i.e., Shed-Acute-Phase-Antigens). Although the tandem repeat is not directly involved in the catalytic activity, it stabilizes the trans-sialidase activity in the blood to increase the half-life of the enzyme from about 7 to about 35 hours. See, Pollevick et al., Mol. Biochem. Parasitol. 47:247 250 (1991) and Buscaglia et al., J. Infect. Dis., 177(2):431 6 (1998). Amino acid residues 667-1162 of SEQ ID NO:4 correspond to the C-terminal tandem repeat of clone 7F. The C-terminal tandem repeat domain is not required for the neurotrophic activity of the PDNF. See, e.g., Chuenkova et al., U.S. Application Publication Nos. 2009/0117593 and 2006/0229247.

PDNF binds and activates the NGF receptor TrkA to trigger PI3K/Akt and MAPK/Erk signaling (Chuenkova and PereiraPerrin J. Neurochem., 91:385-394 (2004); Woronowicz et al., Glycobiology 14:987-98 (2004)). However, neurotrophic receptor activation is independent of sialic acid binding because the neuraminidase/trans-sialidase 1) does not lose Trk receptor recognition after point mutations that sharply reduce neuraminidase/trans-sialidase activities (11), 2) Trk-binding activity is mimicked by a 24-mer synthetic peptide (13), and 3) binds and activates Trk receptors in sialic acid-deficient cells (60). Furthermore, the enzyme, after phosporylation by Akt kinase, promotes cell survival in the cytosol where sialyl-conjugate substrates are absent, (14). Neuraminidase/trans-sialidase is called PDNF to underscore paracrine growth factor function independent of sialic acid binding. Binding to TrkC leads to *T cruzi* entry into cardiomyocytes and cardiac fibroblasts, whereas binding to TrkA triggers cardioprotection by autocrine and paracrine mechanisms (4, 5). A peptide mapping approach has revealed that a bacterially-expressed truncated PDNF corresponding to amino acids 1-445 of SEQ ID NO:2 promoted survival and differentiation of TrkA-positive PC12 cells while truncated PDNF equivalent to amino acids 1-425 of SEQ ID NO:2 did not (Chuenkova and Pereira, Mol. Biol. Cell 11:1487-1498 (2000)). This finding indicates that the amino acid sequence corresponding to 425-445 of SEQ ID NO:2 is involved in the TrkA-mediated signaling. A predicted three-dimensional structure of the catalytic domain of PDNF is provided in FIG. 34 of U.S. Application Publication No. 2009/0117593.

The invention also encompasses the use of a PDNF fragment that comprises a portion, but not the full-length sequence of PDNF, while retaining the TrkA-binding activity or the ability to activate TrkA signaling pathway. The PDNF fragments of the invention may or may not have neuraminadase or trans-sialidase catalytic activity as desired. Residues 33-666 of SEQ ID NO: 2 is an example of a fragment of PDNF that retains the TrkA-binding activity. Residues 425-455 of SEQ ID NO: 2 is another example of a fragment of PDNF that retains the TrkA-binding activity. In another exemplary embodiment, the PDNF fragment is residues 1 to 588 of SEQ ID NO: 4. In another exemplary embodiment, the PDNF fragment is residues 1 to 596 of SEQ ID NO: 4.

The PDNF polypeptide or PDNF fragment of the invention can be a naturally occurring protein that has TrkA-binding activity (e.g., binds to TrkA receptor or activates TrkA signaling pathway), or an active variant of a naturally occurring protein.

As used herein, "active variants" refers to variant peptides which retain TrkA-binding activity (e.g., binds to TrkA receptor or activates TrkA signaling pathway). An "active variant" may or may not have to have neuraminadase or trans-sialidase catalytic activity as desired. An active variant differs in amino acid sequence from a reference PDNF (such as the PDNF encoded by clone 19Y deposited in GenBank under accession number AJ002174 (SEQ ID NO:2), or the PDNF encoded by clone 7F deposited in GenBank under accession number M61732 (SEQ ID NO:4)), or a reference PDNF fragment, but retains TrkA-binding activity (e.g., retains the ability to bind to TrkA receptor or activates TrkA signaling pathway).

Generally, differences are limited so that the sequences of the reference polypeptide and the active variant are closely similar overall and, in many regions, identical. An active variant of PDNF or PDNF fragment and a reference PDNF or PDNF fragment can differ in amino acid sequence by one or more amino acid substitutions, additions, deletions, truncations, fusions or any combination thereof. Preferably, amino acid substitutions are conservative substitutions. A conservative amino acid substitution refers to the replacement of a first amino acid by a second amino acid that has chemical and/or physical properties (e.g., charge, structure, polarity, hydrophobicity/hydrophilicity) which are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Preferred size of PDNF fragments (including active variants of a PDNF fragment) is at least 10 a.a., at least 12 a.a., at least 15 a.a., or at least 20 a.a. As described herein, such fragments (and active variants of the PDNF fragment) bind to TrkA receptor.

Active variants of PDNF or PDNF fragments include naturally occurring variants (e.g., allelic forms) and variants which are not known to occur naturally.

In one embodiment, an active variant of PDNF shares at least about 85% amino acid sequence similarity or identity with a naturally occurring PDNF (e.g., SEQ ID NO:2, SEQ ID NO:4), preferably at least about 90% amino acid sequence similarity or identity, and more preferably at least about 95%, at least about 96%, at least about 97%, at least about 98%, or at least about 99% amino acid sequence similarity or identity with said PDNF. Preferably, the percentage of identity is calculated over the full length of the active variant.

In certain embodiments, the active variant comprises fewer amino acid residues than a naturally occurring PDNF. In this situation, the variant can share at least about 85% amino acid sequence similarity or identity with a corresponding portion of a naturally occurring PDNF (e.g., amino acid residues 33-666 of SEQ ID NO:2), preferably at least about 90% amino acid sequence similarity or identity, and more preferably at least about 95%, at least about 96%, at least about 97%, at least about 98%, or at least about 99% amino acid sequence similarity or identity with a corresponding portion of said PDNF.

Portions of the amino acid sequence of PDNF which correspond to a variant and amino acid sequence similarity or identity can be identified using a suitable sequence alignment algorithm, such as ClustalW2 (http://www.ebi.ac.uk/Tools/clustalw2/index.html) or "BLAST 2 Sequences" using default parameters (Tatusova, T. et al., FEMS Microbiol. Lett., 174:187-188 (1999)).

Active variants of PDNF or PDNF fragments can be prepared using suitable methods, for example, by direct synthesis, mutagenesis (e.g., site directed mutagenesis, scanning mutagenesis) and other methods of recombinant DNA technology. Active variants can be identified and/or selected using a suitable assay, such as the co-immunoprecitiation and kinase assays. For example, TrkA binding activities can be shown by co-immunoprecitiation (or crosslinking) of TrkA receptor and the PDNF fragment or variant. Activation of TrkA pathway can be shown by kinase assay, such as Ras/MAPK kinase assay or Akt kinase assay. See e.g., US 2009/0117593 A1.

Fusion proteins comprising PDNF or a fragment of PDNF are also contemplated. A fusion protein may encompass a polypeptide comprising PDNF (e.g., SEQ ID NO:2, SEQ ID NO:4), a PDNF fragment (e.g., amino acid residues 33-666 of SEQ ID NO:2) or an active variant thereof as a first moiety, linked via a covalent bond (e.g., a peptide bond) to a second moiety (a fusion partner) not occurring in PDNF as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) and a linker sequence as the second moiety, and PDNF or a PDNF fragment as the first moiety. Additional (e.g., third, fourth) moieties can be present as appropriate. The second (and additional moieties) can be any amino acid, oligopeptide or polypeptide that does not interfere with the TrkA binding activity (e.g., the ability to bind to TrkA receptor or activates TrkA signaling pathway) of PDNF. Fusion proteins can be prepared using suitable methods, for example, by direct synthesis, recombinant DNA technology, etc.

In certain embodiment, the fusion protein comprises a first moiety which shares at least about 85% sequence similarity or identity with PDNF (e.g., SEQ ID NO:2, SEQ ID NO:4) or a fragment of PDNF (e.g., amino acid residues 33-666 of SEQ ID NO:2), preferably at least about 90% sequence similarity or identity, and more preferably at least about 95%, at least about 96%, at least about 97%, at least about 98%, or at least about 99% sequence similarity or identity with the PDNF or PDNF fragment. Preferably, the percentage of identity is calculated over the full length of the first moiety.

Chagas Disease and Immune Response

Chagas disease, a major cause of morbidity and mortality in Latin America (25, 27, 41), is commonly transmitted by blood-sucking reduviid bugs, which, during a blood meal, release *Trypanosoma cruzi* that, as metacyclic trypomastigotes, gain access into the body through mucosal surfaces or discontinuity in the skin, where they elicit a pronounced inflammatory response. In the conjunctiva, inflammation and edema may last many weeks and, in endemic areas, the unilateral eye inflammation serves as a diagnostic tool (Romana' sign). After a few days in the transmission site, *T cruzi* spreads throughout the body and, in the heart, triggers severe inflammation and tissue damage that often gives rise to ventricular repolarization, ejection defects, pleural effusion, and cardiomegaly (6, 35, 39). This response wanes in most (>95%) infected patients, who progress to symptomless and pathology-free indeterminate phase that can last years or a lifetime. However, <5% acute chagasic patients progress to widespread and fulminating myocarditis.

Host survival and *T cruzi* growth are controlled by innate and acquired immunity (25, 27, 41). During the initial stage of infection, Toll-like receptor (TLR) family of pattern recognition proteins play an important role in *T cruzi* recognition, as they are activated by parasite molecules such as DNA, RNA or glycosylphosphatidyl-inositol (GPI) anchors, initiating a signaling cascade dependent on the adaptor molecule myeloid differentiation factor 88 (MyD88) that mediates upregulation of proinflammatory genes pivotal to the resistance to *T cruzi* infection. In addition, *T cruzi* activates Nodi and inflammasome (NLRP3) pro-inflammatory pathways, and the end-result is an increase in interleukin-1p (IL-1 p) (20), IL-6 (20, 55), IL-12 (1-3, 8, 29), TNFa (3, 7, 8, 29), interferon-p and interferon-Y (3, 9, 20, 24, 29, 43), and monocyte chemoattractant protein-1 (MCP-1)/CCL2 and other chemokines essential to the recruitment of inflammatory cells to infection sites (16, 54).

A most-studied mechanism underlying innate immunity in *T cruzi* infection is Toll-like receptor (TLR) activation by lipids and other parasite molecules. However, yet-to-be identified pathways should exist. It was reported that connective tissue growth factor (CTGF), also known as CCN2, a matricellular protein implicated in fibrosis and inflammation in several disorders such as diabetic neuropathy (19), augments expression of various pro-inflammatory cytokines, including the chemokine MCP-1, following binding and activation of neurotrophic receptor TrkA on cardiomyocytes (57, 58). Given that CTGF/CCN2 receptor is TrkA, the same that sPDNF interacts with to promote downstream signaling and cell survival in host cells, including cardiac cells (4, 5), the connection between *T cruzi* PDNF activation of TrkA and/or TrkC on cardiomyocytes and cardiac fibroblasts and increased expression of mediators of innate immunity was investigated.

As described herein, *T cruzi* strongly increased expression of monocyte chemoattractant protein-1 (MCP-1)/CCL2 and fractalkine (FKN)/CX3CL1 in cellular and mouse models of heart infection. Mechanistically, increased expression of MCP-1 and FKN stemmed from the interaction of parasite-derived neurotrophic factor (PDNF)/trans-sialidase with neurotrophic receptors TrkA and TrkC, as assessed by pharmacological inhibition, neutralizing antibodies and gene silencing studies. A single dose of intravenous PDNF into naive mice resulted in a dose-dependent increase in MCP-1 and FKN in the heart and liver, and pulse-like kinetics that peaked 3 hr post-injection. Intravenous PDNF also augmented MCP-1 and FKN in TLR-deficient MyD88 knockout mice. Without being bound to a particular theory, this shows that PDNF has a TLR-independent action. Although single PDNF injections did not increase MCP-1 and FKN receptors, multiple PDNF injections at short intervals increased expression of receptor transcripts in the heart and liver. Without being bound to a particular theory, this indicates that sustained PDNF expression triggered cell recruitment at infection sites. Thus, given that MCP-1 and FKN are chemokines important to the recruitment of immune cells to combat inflammation triggers and to enhance tissue repair, these results describe a new mechanism in innate immunity of *T cruzi* infection mediated by Trk signaling. This pathway has similarities with an endogenous inflammatory and fibrotic pathway that results from cardiomyocyte-TrkA recognition by matricellular connective tissue growth factor (CTGF/CCN2).

Use of PDNF for Treating Inflammatory Diseases

In one aspect, the invention provides a method of decreasing inflammation in a non-neuronal tissue of a subject, involving administering to the subject soluble parasite-derived neurotrophic factor (sPDNF), or fragment thereof, in an amount effective to decrease inflammation in the non-neuronal tissue.

In another aspect, the invention provides a method of decreasing inflammation in a cardiac, liver, pancreas, or gastrointestinal tissue of a subject, involving administering to the subject soluble parasite-derived neurotrophic factor (sPDNF), or a fragment thereof, in an amount effective to decrease inflammation in the cardiac, liver, pancreatic, or gastrointestinal tissue.

In still another aspect, the invention provides a method of increasing expression of an anti-inflammatory factor in a non-neuronal cell or tissue, involving contacting the non-neuronal cell or tissue with soluble parasite-derived neurotrophic factor (sPDNF), or a fragment thereof, in an amount effective to increase expression of an anti-inflammatory factor in the non-neuronal cell or tissue.

In another aspect, the invention provides a method of treating a cardiac inflammatory disease in a subject in need thereof, involving: administering to the subject an anti-inflammatory or therapeutically effective amount of parasite-derived neurotrophic factor (PDNF), or a fragment of PDNF. In certain embodiments, the fragment of PDNF binds to TrkA Receptor. In certain embodiments, the subject does not have Chagas disease. In certain embodiments, the subject does not have a *mycoplasma* infection. In certain embodiments, the subject does not have a loss of hematopoietic regeneration capacity. In certain embodiments, the cardiac inflammatory disease is myocarditis, cardiomyopathy, endocarditis, or pericarditis.

In one aspect, the invention provides a method of increasing stem cell number, involving contacting a non-neuronal cell or tissue with soluble parasite-derived neurotrophic factor (sPDNF), or fragment thereof.

In another aspect, the invention provides a method of increasing stem cell mobilization, involving contacting a non-neuronal cell or tissue with soluble parasite-derived neurotrophic factor (sPDNF), or fragment thereof.

In yet another aspect, the invention provides a method of increasing stem cell proliferation, involving contacting a non-neuronal cell or tissue with soluble parasite-derived neurotrophic factor (sPDNF), or fragment thereof.

In another aspect, the invention provides a method of promoting the proliferation or mobilization of cardiac stem cells in a subject in need thereof, involving: administering to the subject a therapeutically effective amount of parasite-derived neurotrophic factor (PDNF), or a fragment of PDNF. In certain embodiments, the fragment of PDNF binds to TrkA Receptor. In certain embodiments, the subject does not have Chagas disease. In certain embodiments, the subject does not have a *mycoplasma* infection. In certain embodiments, the subject does not have a loss of hematopoietic regeneration capacity. In certain embodiments, the subject is suffering from, or susceptible to myocarditis, cardiomyopathy, endocarditis, or pericarditis.

The PDNF or a TrkA binding fragment thereof described herein may also be used to treat fibrosis, in particular cardiac fibrosis. Cardiac fibrosis refers to an abnormal thickening of the cardiac muscle or heart valves due to inappropriate proliferation of cardiac fibroblasts, with common characteristics such as excessive collagen accumulation and defective function caused by the replacement of normal tissues by fibrous tissues. Acute cardiac fibrosis includes responses to acute hypertension, trauma, infection, surgery, burn, radiation and chemotherapeutic agents. Chronic fibrosis is caused by other chronic diseases inducing chronic hypertension, virus infection, diabetes, obesity, fatty liver and dermatosclerosis.

In one aspect, the invention provides a method of treating a hepatic inflammatory disease in a subject in need thereof, involving: administering to the subject an anti-inflammatory or therapeutically effective amount of parasite-derived neurotrophic factor (PDNF), or a fragment of PDNF. In certain embodiments, the fragment of PDNF binds to TrkA Receptor. In certain embodiments, the subject does not have Chagas disease. In certain embodiments, the subject does not have a *mycoplasma* infection. In certain embodiments, the subject does not have a loss of hematopoietic regeneration capacity. In certain embodiments, the hepatic inflammatory disease is hepatitis or hepatic fibrosis.

In another aspect, the invention provides a method of promoting the proliferation or mobilization of hepatic progenitor cells in a subject in need thereof, involving: administering to the subject a therapeutically effective amount of parasite-derived neurotrophic factor (PDNF), or a fragment of PDNF. In certain embodiments, the fragment of PDNF binds to TrkA Receptor. In certain embodiments, the subject does not have Chagas disease. In certain embodiments, the subject does not have a *mycoplasma* infection. In certain embodiments, the subject does not have a loss of hematopoietic regeneration capacity. In certain embodiments, the subject is suffering from, or susceptible to hepatitis or hepatic fibrosis.

In another aspect, the invention provides a method of treating an inflammatory disease of the gastrointestinal (GI) tract in a subject in need thereof, involving: administering to the subject an anti-inflammatory or therapeutically effective amount of parasite-derived neurotrophic factor (PDNF), or a fragment of PDNF, where the fragment of PDNF binds to TrkA Receptor. In certain embodiments, the subject does not have Chagas disease. Examples of inflammatory diseases of the gastrointestinal (GI) tract include, for example, inflammatory bowel diseases (IBD, with ulcerative colitis and Crohn's disease being the two major types of IBD), irritable bowel syndrome, ileitis, chronic inflammatory intestinal disease, celiac disease, etc.

In one aspect, the invention provides a method of treating a pancreatic inflammatory disease in a subject in need thereof, involving: administering to the subject an anti-inflammatory or therapeutically effective amount of parasite-derived neurotrophic factor (PDNF), or a fragment of PDNF. In certain embodiments, the fragment of PDNF binds to TrkA Receptor. In certain embodiments, the subject does not have Chagas disease. In certain embodiments, the subject does not have a *mycoplasma* infection. In certain embodiments, the subject does not have a loss of hematopoietic regeneration capacity. In certain embodiments, the hepatic inflammatory disease is type 1 or type 2 diabetes. In another aspect, the invention provides a method of treating a liver disease in a subject in need thereof, involving: administering to the subject an anti-inflammatory or therapeutically effective amount of parasite-derived neurotrophic factor (PDNF), or a fragment of PDNF, where the fragment of PDNF binds to TrkA Receptor. In certain embodiments, the subject does not have Chagas disease. Examples of liver diseases include, e.g., liver failure, hepatitis (acute or chronic), liver cirrhosis, toxic liver damage (for example alcohol), hepatic encephalopathy, hepatic coma, hepatic necrosis, etc. Other types of disease that can be treated by PDNF or PDNF fragments include, for example, amyotrophic lateral sclerosis.

As disclosed and exemplified herein, PDNF, or a TrkA-binding fragment thereof, is a stem cell renewal factor that promotes the proliferation and mobilization of stem cells such as cardiac stem cells and hepatic progenitor cells, and can be used to treat cardiac or hepatic inflammatory diseases, in particular diseases characterized by inflammation and damage of cardiac or hepatic tissues.

As disclosed and exemplified herein, the inventor discovered that PDNF is a paracrine factor that promote both the proliferation and mobilization of stem cells. Although not wishing to be bound by a particular theory, it is believed that PDNF can increase the number of endogenous resident cardiac stem cells by at least two mechanisms. First, it is believed that PDNF promotes the proliferation of cardiac stem cells (as shown by the increased expression of cardiac stem cell markers Sca-1 and c-Kit) by binding to TrkA receptor and activating the TrkA-mediated kinas pathway. Second, it is also believed that PDNF can promote the mobilization of cardiac stem cells by increasing the synthesis of chemotatic factors (e.g., an increased expression of chemokine CCL2 and its receptor CCR2).

Although not wishing to be bound by a particular theory, it is believed that PDNF triggers the proliferation and mobilization of cardiac stem cells directly by activating TrkA receptor, as well as indirectly by increasing the expression of nerve growth factor (NGF) (~80-fold increase in cardiac fibroblasts in some of the experiments). NGF can protect against myocardial infarction partly by upregulating cardiac c-Kit$^+$ stem cells. Hence, it is believed that PDNF promotes the proliferation and mobilization of cardiac progenitor cells both directly (via TrkA receptor) and indirectly (via increased expression of NGF).

The increase of cardiac stem cells, triggered by PDNF, results in an increased regenerative activity (repair of damaged tissue), as stem cells can differentiate into mature cardiomyocytes. The increased stem cells also provide strong anti-inflammatory effect. In a model of chronic Chagas disease, an intravenously-administered PDNF fragment reduced cardiac inflammation (as reflected by CD8 lymphocyte infiltrates, and pro-inflammatory cytokines such as tumor necrosis factor-$\alpha$), and nearly eliminated fibrosis. Such PDNF-triggered global anti-inflammatory activity is attributed to the increased proliferation and mobilization stem cells, which can reduce or suppress inflammation.

The methods described herein use PDNF, or a TrkA-binding fragment thereof, to trigger the expansion of endogenous cardiac stem cells, which provides certain advantages over stem cell therapy using non-cardiac progenitor cells. Prior stem cell clinical trials using non-cardiac progenitor cells has failed, with problems such as differentiation of the stem cells into non-cardiac cells instead of cardiomyocytes, inefficient delivery (~10% cardiac retention), cell fusion, or adoption of a mature blood or skeletal muscle cell phenotype.

As described and exemplified herein, the administration of PDNF or PDNF fragments can lead to an increased or decreased production of certain cytokines and paracrine factors that modulate immune response and reduce inflammation. It is generally believed that TH1 lymphocytes, although do not attack the myocardium themselves, could trigger cytotoxic T cells to become auto-reactive. These TH1-lymphocytes also produce high levels of pro-inflammatory cytokines (such as IFN-$\gamma$, TNF-$\alpha$, IL-1, IL-2, IL-12, IL-18, or IL-23), thereby suppressing the formation of regulatory T-cells (Treg) and TH2. Inhibition of Treg formation allows a stronger auto-reactive cardiac response, thereby creating more cardiac damage. Contrary to TH1, TH2 do not enhance cytotoxic or phagocytic activity. Accordingly, their cytokine production is more immunosuppressive, including IL-10 and IL-4. Other immune-tolerant cytokines or factors produced by TH2 or Treg cells include, for example, TGF-$\beta$1, IL-5, IL-6, prostaglandin-E2 (PGE2).

It is believed that the endogenous stem cells described herein can modulate T-cell response by altering the TH1/TH2 ratio. This leads to a larger percentage of Treg cells, which create an immuno-tolerant environment and more TH2 cells, suppressing the formation of TH1 lymphocytes. Meanwhile, cell-mediated immune response via TH1 cells, recruiting more cytotoxic T cells and neutrophils, is also suppressed.

In another aspect, the invention provides a method of treating a subject suffering from, or susceptible to an inflammatory disease, such as a cardiac or hepatic inflammatory disease, comprising: administering to said subject an amount of parasite-derived neurotrophic factor (PDNF), or a fragment of PDNF, where said fragment of PDNF binds to TrkA Receptor, and where the administration provides a serum concentration of: at least about 1 ng/mL of IL-1ra, or at least about 0.5 ng/mL of TSG-6 in said subject within 4 hours, 6 hours, 8 hours, 12 hours, 24 hours, 48 hours, or 72 hours of administration. Another example of the inflammatory disease is an inflammatory disease of the GI-tract.

IL-1ra (interleukin-1 receptor antagonist) is a member of the interleukin 1 cytokine family. IL1ra is secreted by various types of cells including immune cells, epithelial cells, and adipocytes, and is a natural inhibitor of the pro-inflammatory effect of IL1$\beta$. This protein inhibits the activities of interleukin 1, alpha (IL1A) and interleukin 1, beta (IL1B), and modulates a variety of interleukin 1 related immune and inflammatory responses. In humans, IL1-ra is encoded by the IL1RN gene. It has been reported that the serum concentration of IL1-ra in a normal human is about 0.24-0.34 ng/ml) (see, e.g., Am. J. Respir. Crit. Care Med. 1997 April; 155(4):1469-73).

TSG-6 (Tumor necrosis factor-inducible gene 6 protein) is also known as TNF-stimulated gene 6 protein). In human, TSG-6 is encoded by the TNFAIP6 (tumor necrosis factor, alpha-induced protein 6) gene. The expression of this gene can be induced by a number of signaling molecules, principally tumor necrosis factor α (TNF-α) and interleukin-1 (IL-1). The expression can also be induced by mechanical stimuli in vascular smooth muscle cells, and is found to be correlated with proteoglycan synthesis and aggregation. In addition, TSG-6 forms both covalent and non-covalent complexes with inter-α-inhibitor (a serine protease inhibitor present at high levels in serum) and potentiates its antiplasmin activity. It has been reported that TSG-6 cannot be detected in sera of normal individuals (see, e.g., Am J Pathol. 2001 November; 159(5): 1711-1721).

In another aspect, the invention provides a method of treating a subject suffering from, or susceptible to an inflammatory disease, such as a cardiac or hepatic inflammatory disease, comprising: administering to said subject an amount of parasite-derived neurotrophic factor (PDNF), or a fragment of PDNF, where said fragment of PDNF binds to TrkA Receptor, and where the administration provides a serum concentration of at least about 0.25 ng/mL of Cox-2 in said subject within 4 hours, 6 hours, 8 hours, 12 hours, 24 hours, 48 hours, or 72 hours of administration. Another example of the inflammatory disease is an inflammatory disease of the GI-tract.

COX-2 (cyclooxygenase-2 or prostaglandin-endoperoxide synthase 2) is an enzyme existing as a homodimer, each monomer with a molecular mass of about 70 kDa. In humans, COX-2 is encoded by the PTGS2 gene. COX-2 is unexpressed under normal conditions in most cells, but elevated levels are found during inflammation. It has been reported that COX-2 is undetectable in most tissues in the absence of stimulation (see, e.g., Proc. Natl. Acad. Sci. USA, Vol. 96, pp. 272-277, January 1999).

In another aspect, the invention provides a method of treating a subject suffering from, or susceptible to an inflammatory disease, comprising: administering to said subject an amount of parasite-derived neurotrophic factor (PDNF), or a fragment of PDNF, where said fragment of PDNF binds to TrkA Receptor, and where the administration provides a serum concentration of: at least about 0.5 ng/mL, at least about 1 ng/mL, at least about 1.5 ng/mL, at least about 2 ng/mL, at least about 2.5 ng/mL, at least about 3 ng/mL, at least about 3.5 ng/mL, at least about 4 ng/mL, at least about 4.5 ng/mL, at least about 5 ng/mL, at least about 5.5 ng/mL, or at least about 6 ng/mL, of IL1-ra within 4 hours, 6 hours, 8 hours, 12 hours, 24 hours, 48 hours, or 72 hours of administration. In certain embodiments, the inflammatory disease is mediated by the interleukin-1 (IL-1) receptor. A non-exclusive list of acute and chronic interleukin-1 (IL-1)-mediated inflammatory diseases includes but is not limited to the following: acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; degenerative disk disease; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

In another aspect, the invention provides a method of treating a subject suffering from, or susceptible to an inflammatory disease, such as a cardiac or hepatic inflammatory disease, comprising: administering to said subject an amount of parasite-derived neurotrophic factor (PDNF), or a fragment of PDNF, where said fragment of PDNF binds to TrkA Receptor, and where the administration provides: at least about 5 fold, at least about 6 fold, at least about 7 fold, at least about 8 fold, at least about 9 fold, or at least about 10 fold increase of the serum concentration of IL-1ra, as compared to serum concentration of IL-1ra prior to administration, in said subject within 4 hours, 6 hours, 8 hours, 12 hours, 24 hours, 48 hours, or 72 hours of administration. Another example of the inflammatory disease is an inflammatory disease of the GI-tract.

In another aspect, the invention provides a method of treating a subject suffering from, or susceptible to an inflammatory disease, comprising: administering to said subject an amount of parasite-derived neurotrophic factor (PDNF), or a fragment of PDNF, where said fragment of PDNF binds to TrkA Receptor, and where the administration provides a serum concentration of: at least about 0.5 ng/mL, at least about 1 ng/mL, at least about 1.5 ng/mL, at least about 2 ng/mL, at least about 2.5 ng/mL, at least about 3 ng/mL, at least about 3.5 ng/mL, at least about 4 ng/mL, at least about 4.5 ng/mL, at least about 5 ng/mL, at least about 5.5 ng/mL, or at least about 6 ng/mL, of TSG-6 within 4 hours, 6 hours, 8 hours, 12 hours, 24 hours, 48 hours, or 72 hours of administration. A link between TSG-6 and inflammation has been established by studies that high concentrations of TSG-6 are present in the synovial fluid of patients with rheumatoid arthritis and some other forms of arthritis, whereas no TSG-6 was detectable in control synovial fluids. Synovial cells from a rheumatoid arthritis patient showed high levels of constitutive TSG-6 production, and both synovial cells and chondrocytes in culture showed increased TSG-6 production in response to IL-1 or TNF-β (Wisniewski et al., supra, 1993). As such, the PDNF of PDNF fragments described herein can be used to treat inflammatory diseases linked to IL-1 or TNF-β, such as, rheumatoid arthritis, other inflammatory connective tissue disorders, and cancer.

In another aspect, the invention provides a method of treating a subject suffering from, or susceptible to an inflammatory disease, comprising: administering to said subject an amount of parasite-derived neurotrophic factor (PDNF), or a fragment of PDNF, where said fragment of PDNF binds to TrkA Receptor, and where the administration provides a serum concentration of: at least about 0.1 ng/mL, at least about 0.2 ng/mL, at least about 0.25 ng/mL, at least about 0.3 ng/mL, at least about 0.4 ng/mL, at least about 0.5 ng/mL, at least about 1 ng/mL, at least about 1.5 ng/mL, at least about 2 ng/mL, at least about 2.5 ng/mL, at least about 3 ng/mL, at least about 3.5 ng/mL, at least about 4 ng/mL, at least about 4.5 ng/mL, at least about 5 ng/mL, at least about 5.5 ng/mL, or at least about 6 ng/mL, of Cox-2 within 4 hours, 6 hours, 8 hours, 12 hours, 24 hours, 48 hours, or 72 hours of administration.

The serum concentration of the inflammatory or anti-inflammatory markers described herein, such as IL-1ra, TSG-6, and COX-2, can be determined by any method which quantitatively determines the amount of a molecule(s). One example is flow cytometry of a sample to quantitatively identify the presence of the specific molecule in the sample. Another example is the use an analytical system that utilizes multianalyte fluorometric beads, such as the Bead Lite Milipore luminex platform. Other assay methods include, for example, quantitative immunology based assays such as ELISA analysis, mass spectroscopy or mass spectrometry. The serum concentrations of multiple cytokines or factors can be determined simultaneously, or separately.

The PDNF or a TrkA binding fragment thereof described herein may also be used to treat rheumatoid arthritis. Rheumatoid arthritis (RA) is an autoimmune disease characterized by chronic inflammation of synovial tissue, leading to destruction of the joint architecture. Efficacy of the administration can be measured by RA-associated biomarkers. Examples of RA-associated biomarkers include, but are not limited to, e.g., high-sensitivity C-reactive protein (hsCRP), serum amyloid A (SAA), erythrocyte sedimentation rate (ESR), serum hepcidin, interleukin-6 (IL-6), and hemoglobin (Hb). As will be appreciated by a person of ordinary skill in the art, an increase or decrease in an RA-associated biomarker can be determined by comparing the level of the biomarker measured in the patient at a defined time point after administration of PDNF (or fragments) to the level of the biomarker measured in the patient prior to the administration (i.e., the "baseline measurement"). The defined time point at which the biomarker can be measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days or more after administration of PDNF (or PDNF fragments).

In another aspect, the invention provides a method of promoting the proliferation or mobilization of hepatic progenitor cells in a subject in need thereof, comprising: administering to said subject a therapeutically effective amount of parasite-derived neurotrophic factor (PDNF), or a fragment of PDNF, where said PDNF fragment binds to TrkA Receptor.

In certain embodiments, the subject does not have Chagas disease. In certain embodiments, the subject does not have a *mycoplasma* infection. In certain embodiments, the subject does not have a loss of hematopoietic regeneration capacity.

Myocarditis and Cardiomyopathy

Myocarditis and cardiomyopathy are a group of diseases primarily of the myocardium that are not the result of hypertensive, congenital, ischemic, or valvular heart disease. Myocarditis generally refers to an acute myocardial disease characterized by inflammation, and cardiomyopathy generally refers to more chronic myocardial diseases in which the inflammatory features are not conspicuous (Concise Pathology, 1st ed., Appleton & Lange, 367 (1991)). Cardiomyopathies can be classified according to pathophysiologic type as dilated congestive, hypertrophic obstructive, hypertrophic non obstructive, apical obliterative, diffuse nonobliterative restrictive, and obliterative restrictive. Myocarditis and cardiomyopathy can lead to fever, chest pain, leukocytosis, increased erythrocyte sedimentation rate, left ventricular failure, arrythmias, heart block, ECG changes, and eventually cardiac failure.

Myocarditis and cardiomyopathy result from an immune response against the myocardium, including lymphocytic infiltration and inflammation. The immune response can occur secondary to infectious diseases such as Chagas disease (American trypanosomiasis), toxoplasmosis, trichinosis, ricksettal infection (typhus, Rocky Mountain spotted fever), fungal infections, and metazoan parasites; or secondary to autoimmune diseases such as rheumatic fever, rheumatoid arthritis, systemic lupus erythematosus, progressive systemic sclerosis, and polyarthrits *nodosa*. The immune response leading to myocarditis can be idiopathic in nature as seen in Fiedler's myocarditis. Additionally, myocarditis can be caused by drug reaction to penicillin or sulfonamide, for example.

Acute endocarditis generally refers to an inflammatory disease of the visceral or parietal pericardium (Pathology, J.B. Lippencott Co, 538 (1988)), and can occur secondary to bacterial, viral (especially echovirus, and Coxsackie Group B), or fungal infection, and can accompany systemic diseases such as rheumatoid arthritis, systemic lupus erythematosus, scleroderma, and uremia. Pericarditis can also occur after cardiac trauma or cardiac surgery that is suggested as being caused by immunologic hypersensitivity. Acute pericarditis can lead to chronic constrictive pericarditis, effusion, and hemorrhage, all of which can result in cardiac failure.

Myocardial Infarction (MI)

Myocardial infarction (MI) is the most common cause of mortality in developed countries. It is a multifactorial disease that involves atherogenesis, thrombus formation and propagation. Thrombosis can result in complete or partial occlusion of coronary arteries. The luminal narrowing or blockage of coronary arteries reduces oxygen and nutrient supply to the cardiac muscle (cardiac ischemia), leading to myocardial necrosis and/or stunning. MI, unstable angina, and sudden ischemic death are clinical manifestations of cardiac muscle damage. All three endpoints are part of the Acute Coronary Syndrome. Recurrent myocardial infarction can generally be viewed as a severe form of MI progression caused by multiple vulnerable plaques that are able to undergo pre-rupture or a preerosive state, coupled with extreme blood coagulability.

Acute myocardial infarction is typically treated through a therapy in which blood flow is restored by recanalization of the occluded coronary artery, together with treatment of arrhythmia, such as ventricular fibrillation. Myocardial ischemia-reperfusion therapies include a thrombolytic therapy using, for example, t-PA, and PTCA using a balloon catheter. However, it has been known that myocardial ischemia-reperfusion causes inflammatory response due to, for example, free radicals (e.g., active oxygen), vascular endothelial cell injury, or neutrophil activation, resulting in additional damage to the myocardium. Thus, there is a need for development of a drug that reduces the incidence of myocardial ischemia-reperfusion injury.

For example, after myocardial infarction, a local inflammatory reaction clears the damaged myocardium from dead cells and matrix debris at the onset of scar formation. The intensity and duration of this inflammatory reaction are intimately linked to post-infarct remodeling and cardiac dysfunction. Strikingly, treatment with standard anti-inflammatory drugs worsens clinical outcome, suggesting a dual role of inflammation in the cardiac response to injury.

Stem Cell Therapies

Development of regenerative therapeutic strategies to reverse the progression of advanced heart failure is one of the most urgent clinical needs. Cell replacement therapies using stem cells have attracted significant interest. For example, stem cell therapy using mesenchymal stem cells (MSCs) has been found to have beneficial effects, mostly related to paracrine actions. F. van den Akker, et al., Cardiac stem cell therapy to modulate inflammation upon myocardial infarction, Biochimica et Biophysica Acta (2012), http://dx.doi.org/10.1016/j.bbagen.2012.08.026. One of the suggested paracrine effects of stem cell therapy is modulation of the immune system. MSCs are reported to interact with several cells of the immune system and could therefore be a means to reduce detrimental inflammatory reactions and promote the switch to the healing phase upon cardiac injury.

Early studies in animals suggested that bone marrow cells might have potential as cardiac regenerative therapeutics. Ptaszek, et al., *Lancet* 379, 933-942 (2012). Many clinical trials followed these reports. Although injection with bone marrow cells was subsequently reported to be safe, the associated benefit was variable. In some trials, benefit was present, but short-lived. In other trials, no benefit was noted. Problems associated with the use of non-cardiac stem cells include, for example, differentiation of the stem cells into non-cardiac cells instead of cardiomyocytes, inefficient delivery (~10% cardiac retention), cell fusion, or adoption of a mature blood or skeletal muscle cell phenotype.

For several decades, the paradigm of the heart being a terminally differentiated organ was accepted. Now there is a growing body of evidence that challenges this dogma. It has been demonstrated that the heart contains a pool of stem cells that are not mobilized bone marrow cells, but actual stem cells residing in the heart (Beltrami et al., Adult cardiac stem cells are multipotent and support myocardial regeneration, Cell, 2003; 114:763-76). Several reports describe that cardiac stem cells can be isolated based on the expression of membrane antigens like c-kit, Sca-1 or Islet-1. See, e.g., Bearzi et al., Human cardiac stem cells, Proc Natl Acad Sci USA. 2007, 104:14068-73; Goumans et al., TGF-beta1 induces efficient differentiation of human cardiomyocyte progenitor cells into functional cardiomyocytes in vitro, Stem Cell Res. 2007, 1:138-49; Laugwitz et al., Postnatal isl1+ cardioblasts enter fully differentiated cardiomyocyte lineages, Nature. 2005, 433:647-53.

The identification of resident cardiac stem cells in the human heart, together with the isolation of a complex pool of cardiac cells (called "cardiospheres") indicates a potential use of these autologous cells for cardiac repair, through the enhancement of endogenous regenerative activity. Increasing endogenous cardiac stem cells or cardiomyocytes can be achieved with two approaches. One approach is to stimulate expansion of cardiomyocytes or cardiac stem cells with a drug or paracrine factor. The second approach involves propagation of cardiac cells with regenerative potential ex vivo followed by implantation of these cells directly into an injured area. However, cell implantation after infarction can be limited by two factors: number of cells engrafted into the recipient myocardium, and modest differentiation of the cardiomyocyte progeny. Further, the search for cardiac cells and paracrine factors that are capable of triggering cardiac repair has been considered "challenging." Ptaszek, et al., *Lancet* 379, 933-942 (2012).

The existence of resident cardiac stem cells provides a compelling strategy for cardiac tissue repair. First, cardiac stem cells can differentiate into cardiomyocytes, thereby promoting the regeneration of the damaged heart tissue. Second, cardiac stem cells can also reduce the inflammation of cardiac tissue. Often, when tissue damage occurs, an inflammatory response is stimulated to remove cell remnants and debris. For example, cardiac ischemic responses trigger a strong immune reaction in the heart. This reaction includes the activation of local macrophages and the attraction of other immune cells from the blood, such as neutrophils, monocytes and lymphocytes. These immune cells produce a large number of pro-inflammatory cytokines. This leads to a cascade in which more immune cells are attracted, causing further damage and stress on the surviving cardiomyocytes and leading to even more cell death. Cardiac stem cells can secrete paracrine factors, which can reduce cell death, fibrosis and inflammation. Cardiac stem cells can also produce growth factors and cytokines, and reduce or suppress the inflammatory response that leads to tissue damage. As such, cardiac stem cells can reduce the detrimental inflammatory reactions upon cardiac injury, and promote the switch to the healing phase. This anti-inflammatory effect of cardiac stem cells is surprising.

As disclosed and exemplified herein, the inventor discovered that PDNF is a paracrine factor that promote both the proliferation and mobilization of stem cells. Although not wishing to be bound by a particular theory, it is believed that PDNF increases the number of endogenous resident cardiac stem cells by at least two mechanisms. First, it is believed that PDNF promotes the proliferation of cardiac stem cells (as shown by the increased expression of cardiac stem cell markers Sca-1 and c-Kit) by binding to TrkA receptor and activating the TrkA-mediated kinase pathway. Second, it is also believed that PDNF can promote the mobilization of cardiac stem cells by increasing the synthesis of chemotatic factors (e.g., an increased expression of chemokine CCL2 and its receptor CCR2).

Accordingly, the invention is based in part on the surprising discovery that PDNF can promote the proliferation and mobilization of cardiac stem cells. The increase in the resident cardiac stem cells, triggered by PDNF, in turn promotes the regeneration of damaged tissue, and reduces inflammatory response that can further damage the heart.

Use of the PDNF or PDNF fragment described herein for ex vivo therapy is also envisioned. Because of the population of resident cardiac stem cells are very small, it might be important to expand the stem cells population to take advantage of their regenerative and anti-inflammatory activities. Stem cells or progenitor cells can be isolated from the subject or another donor, expanded in vitro in the presence of PDNF or PDNF fragment, and introduced to the subject. The stem cell population can be achieved by at least two means: promoting the proliferation of the stem cells (e.g., inducing the proliferation of quiescent stem cells), and enhancing the mobilization of stem cells (e.g., recruiting stem cells to the damaged heart tissue by chemotaxis).

It was also discovered that anti-inflammatory effect induced by PDNF is both local (reduction of inflammation in heart) and systemic (reduction of inflammation in other tissues, such as liver). Therefore, the therapeutic use of PDNF is not limited to cardiac inflammatory disease; instead, it can be used to treat inflammation in general.

Accordingly, as a stem cell renewal factor, PDNF can be used to treat inflammatory diseases, such as cardiac inflammatory diseases and hepatic inflammatory diseases. PDNF can also be used to treat an inflammatory disease of the GI-tract.

Polynucleotide Therapy

Polynucleotide therapy is another therapeutic approach in which a nucleic acid encoding a PDNF or sPDNF polypeptide is introduced into cells. The transgene is delivered to cells in a form in which it can be taken up and expressed in a therapeutically effective amount.

Transducing retroviral, adenoviral, or human immunodeficiency viral (HIV) vectors are used for somatic cell gene therapy because of their high efficiency of infection and stable integration and expression (see, for example, Cayouette et al., Hum. Gene Ther., 8:423-430, 1997; Kido et al., Curr. Eye Res. 15:833-844, 1996; Bloomer et al., J. Virol. 71:6641-6649, 1997; Naldini et al., Science 272:263-267, 1996; Miyoshi et al., Proc. Natl. Acad. Sci. USA, 94:10319-

10323, 1997). For example, PDNF or sPDNF nucleic acid molecules, or portions thereof, can be cloned into a retroviral vector and driven from its endogenous promoter, from the retroviral long terminal repeat, or from a promoter specific for the target cell type of interest (such as epithelial carcinoma cells). Other viral vectors that can be used include, but are not limited to, adenovirus, adeno-associated virus, vaccinia virus, bovine papilloma virus, vesicular stomatitus virus, or a herpes virus such as Epstein-Barr Virus.

Gene transfer can be achieved using non-viral means requiring infection in vitro. This would include calcium phosphate, DEAE-dextran, electroporation, and protoplast fusion. Liposomes may also be potentially beneficial for delivery of DNA into a cell. Although these methods are available, many of these are of lower efficiency.

Formulations

The administration of a compound or a combination of compounds for the treatment of an inflammatory disorder may be by any suitable means that results in a concentration of the therapeutic that, combined with other components, is effective in ameliorating, reducing, or stabilizing the inflammatory disorder. In one embodiment, a composition of the invention comprises a PDNF or sPDNF polypeptide. In another embodiment, a composition of the invention comprises a cell contacted with PDNF or sPDNF polypeptide. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit tissue repair, reduce cell death, or induce another desirable biological response. Such determinations do not require undue experimentation, but are routine and can be ascertained without undue experimentation.

The biologically active agents can be conveniently provided to a subject as sterile liquid preparations, e.g., isotonic aqueous solutions, suspensions, emulsions, dispersions, or viscous compositions, which may be buffered to a selected pH. Cells and agents of the invention may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions are prepared by suspending PDNF or sPDNF polypeptide in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

Methods of Delivery

Compositions comprising PDNF or sPDNF may be delivered to a subject in need thereof. Modes of administration include intramuscular, intra-cardiac, intra-hepatic, oral, rectal, topical, intraocular, buccal, intravaginal, intracisternal, intra-arterial, intracerebroventricular, intratracheal, nasal, transdermal, within/on implants, e.g., fibers such as collagen, osmotic pumps, or parenteral routes. The term "parenteral" includes subcutaneous, intravenous, intramuscular, intraperitoneal, intragonadal or infusion.

The compositions can be administered via localized injection, including catheter administration, systemic injection, localized injection, intravenous injection, or parenteral administration. When administering a therapeutic composition of the present invention, it will generally be formulated in a unit dosage injectable form (solution, suspension, emulsion). Dosages can be readily adjusted by those skilled in the art (e.g., a decrease in purity may require an increase in dosage). Compositions of the invention can be introduced by injection, catheter, or the like. Compositions of the invention include pharmaceutical compositions comprising cellular factors of the invention and a pharmaceutically acceptable carrier. Administration can be autologous or heterologous.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the *thymus*; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., islet or beta cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactia poly-(isobutyl cyanoacrylate), poly(2-hydroxyethyl-L-glutam-nine) and, poly(lactic acid).

Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, *acacia*, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in Encyclopedia of Pharmaceutical Technology, supra.

At least two anti-neoplasia therapeutics may be mixed together in the tablet, or may be partitioned. In one example, the first active anti-neoplasia therapeutic is contained on the inside of the tablet, and the second active anti-neoplasia therapeutic is on the outside, such that a substantial portion of the second anti-neoplasia therapeutic is released prior to the release of the first anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydro gels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapy

The PDNF or PDNF fragments described herein may be used together with one or more additional therapeutic agents. When administered in combination, each component may be administered at the same time, or sequentially in any order at different points in time.

Exemplary therapeutic agents include anti-coagulant or coagulation inhibitory agents, anti-platelet or platelet inhibitory agents, thrombin inhibitors, Vitamin K antagonists, glycoprotein IIb/IIIa receptor antagonists, thrombolytic or fibrinolytic agents, anti-arrythmic agents, anti-hypertensive agents, angiotensin converting enzyme inhibitors (ACE-Is), angiotensin receptor blockers (ARBs), beta-blockers, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Commonly used anti-inflammatory agents include, for example, non-steroidal anti-inflammatory drugs (NSAIDS) such as ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are more commonly used. Anti-inflammatory agents include, without limitation, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

TNF is a molecule involved in the inflammatory response of patients with inflammatory diseases. Accordingly, any molecule that blocks TNF function e.g., by blocking TNF binding to the TNF receptor (TNFR), may help modify the progression of an inflammatory disease and alleviate some of its symptoms. Several TNF blockers such as infliximab and etanercept, have been shown to be efficacious in treating cardiovascular diseases.

Molecule that blocks the function of a pro-inflammatory cytokine, e.g., by blocking IL-1 interaction with its receptor, may help modify the progression of inflammatory diseases and alleviate one or more symptoms. Anakinra, a recombinant protein that blocks IL-1 interaction with its receptor (IL-1R) has been shown to be efficacious in treating cardiovascularoid arthritis.

Methods for Evaluating Therapeutic Efficacy

In one approach, the efficacy of the treatment is evaluated by measuring, for example, the biological function of the treated organ (e.g., cardiac cell function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is cardiac tissue and, preferably, the organ is heart.

In another approach, the therapeutic efficacy of the methods of the invention is assayed by measuring an increase in cell number in the treated or transplanted tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [$^3$H]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302(5650):1581-4, 2003; Gu et al., Science 302 (5644):445-9, 2003).

In another approach, efficacy is measured by detecting an increase in the number of viable cells present in a tissue or organ relative to the number present in an untreated control tissue or organ, or the number present prior to treatment. Assays for measuring cell viability are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 0.1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Alternatively, or in addition, therapeutic efficacy is assessed by measuring a reduction in apoptosis. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling)

assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Methods for Evaluating Cardiac Function

Compositions of the invention may be used to enhance cardiac function in a subject having reduced cardiac function. Methods for measuring the biological function of the heart (e.g., contractile function) are standard in the art and are described, for example, in the Textbook of Medical Physiology, Tenth edition, (Guyton et al., W.B. Saunders Co., 2000). In the invention, cardiac function is increased by at least 5%, 10%, 15%, 20%, 30%, 40%, 50%, 60%, 70%, 80%, 90%, or even 100% relative to the cardiac function present in a naturally-occurring, corresponding tissue or organ. Most advantageously, cardiac function is enhanced or damage is reversed, such that the function is substantially normal (e.g., 85%, 90%, 95%, or 100% of the cardiac function of a healthy control subject). Reduced cardiac function may result from conditions such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X ray contrast ventriculography, nuclear imaging ventriculography, computed tomography imaging, rapid spiral computerized tomographic imaging, 3-D echocardiography, invasive cardiac pressures, invasive cardiac flows, invasive cardiac cardiac pressure-volume loops (conductance catheter), non-invasive cardiac pressure-volume loops.

Kits

The present compositions may be assembled into kits or pharmaceutical systems for use in ameliorating an inflammatory disease or disorder. Compositions of the invention comprising biologically active agents (e.g., PDNF or sPDNF) are supplied along with additional reagents in a kit. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Parasite-Derived Neurotrophic Factor (PDNF) Promotes Stem Cell Activity and Proliferation This example shows that PDNF is a renewal factor for cardiac stem cells and hepatic stem cell. In addition, PDNF stimulated the expression of anti-inflammatory factors IL1-Ra, TSG-6 and COX-2.

As shown in FIG. 2, intravenous administration of soluble PDNF (sPDNF) into naïve mice increased expression of cardiac and hepatic stem cell markers independently of TLR signaling, expanded cardiac Sca-1$^+$ cells, and increased expression of IL1-Ra, TSG-6 and COX-2.

Figure 3A:
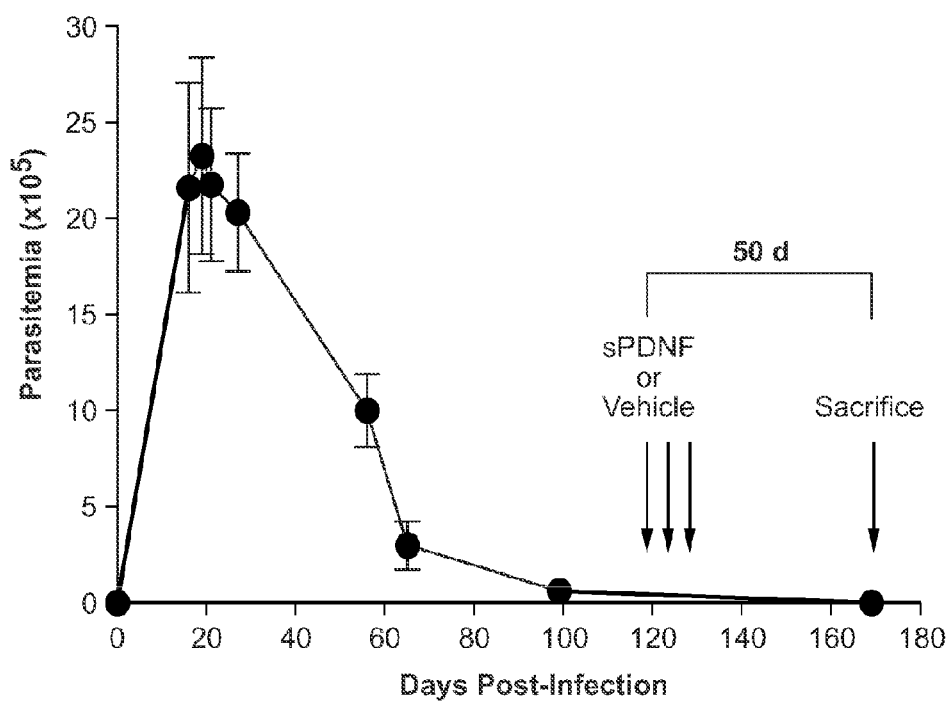
FIGS. 3A and 3B show that intravenous sPDNF triggered a dramatic reduction in inflammatory infiltrates in the heart of mice with chronic Chagas cardiomyopathy (CCC).
Figure 3B:
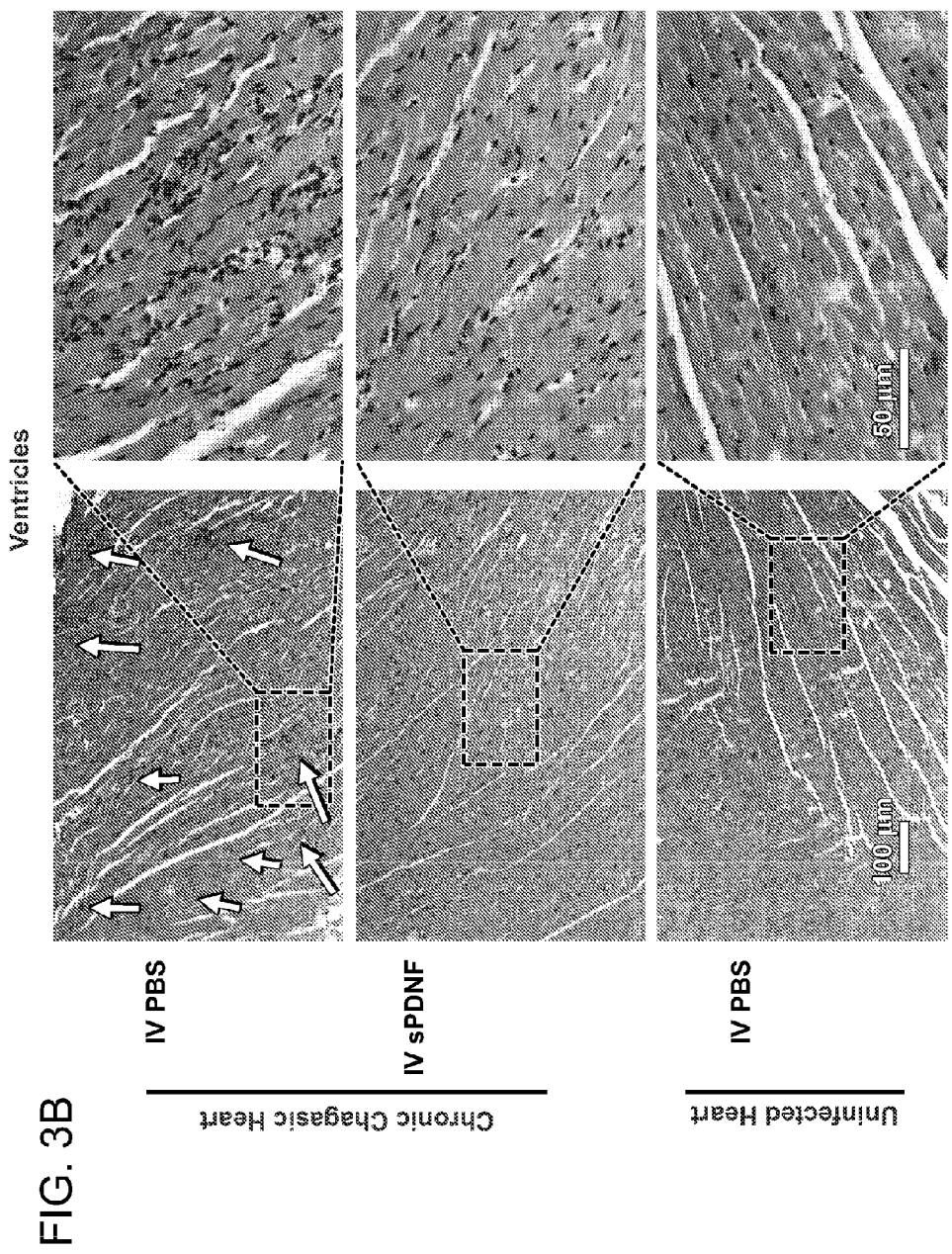

FIG. 3 shows that intravenous administration of soluble PDNF (sPDNF) triggered a dramatic reduction in inflammatory infiltrates in the heart of mice with chronic Chagas cardiomyopathy (CCC).

Figure 4:
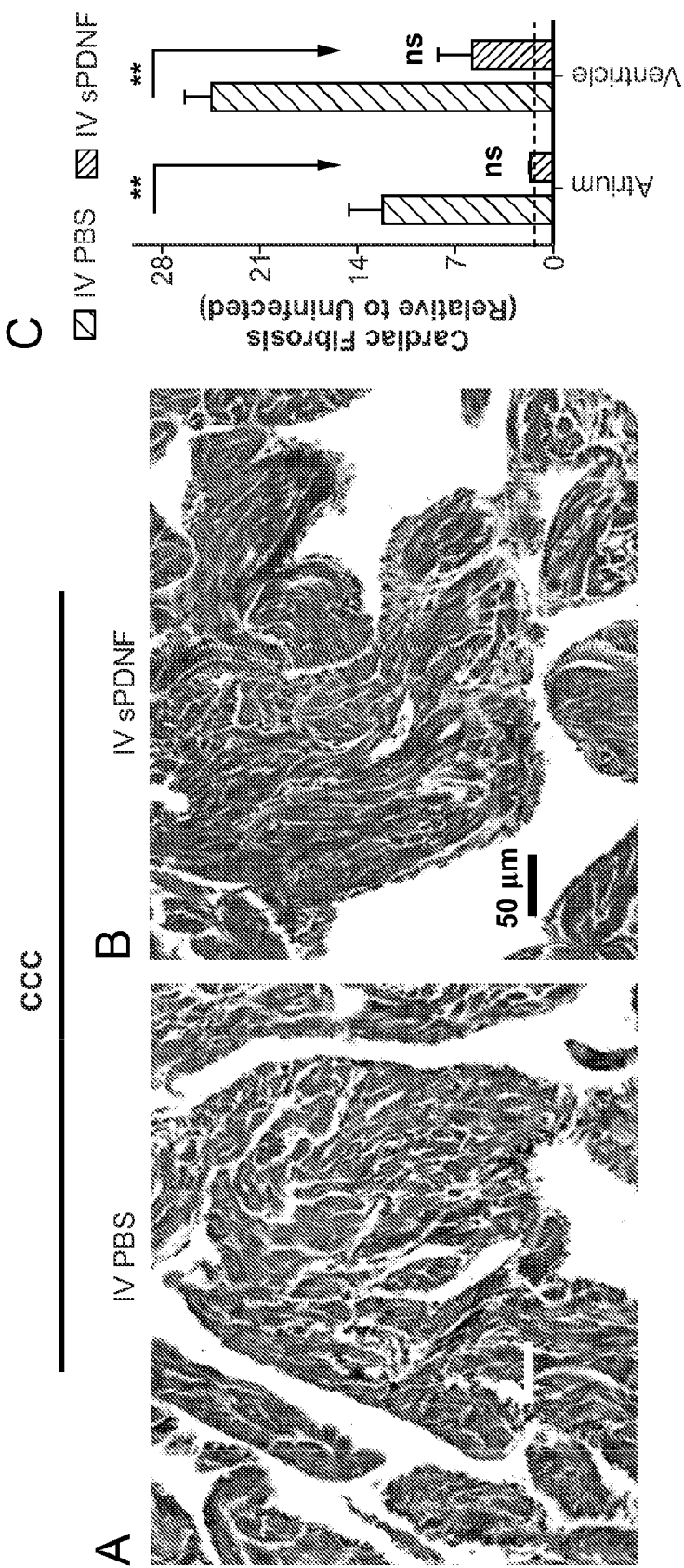
FIGS. 4A-4C show that intravenous sPDNF reduced cardiac fibrosis in mice with chronic Chagas cardiomyopathy (CCC). Same mice and experimental protocol as described in FIG. 3A were used except that paraffin-embedded heart sections were stained with Masson-Trichrome to visualize collagen in fibrotic areas (blue) and viable muscle fibers (red).
FIG. 4F is a graph showing TSG-6 serum levels assessed by ELISA (MyBiosource) in mice uninfected (Un-Inf) or bearing CCC and injected IV with vehicle PBS or sPDNF following the protocol described in FIG. 3. Bars represent the average (±SD) of three mice per point; two separate experiments, , $P<0.01$.

FIG. 4 shows that intravenous administration of soluble PDNF (sPDNF) reduced cardiac fibrosis in mice with chronic Chagas cardiomyopathy (CCC).

Figure 5:
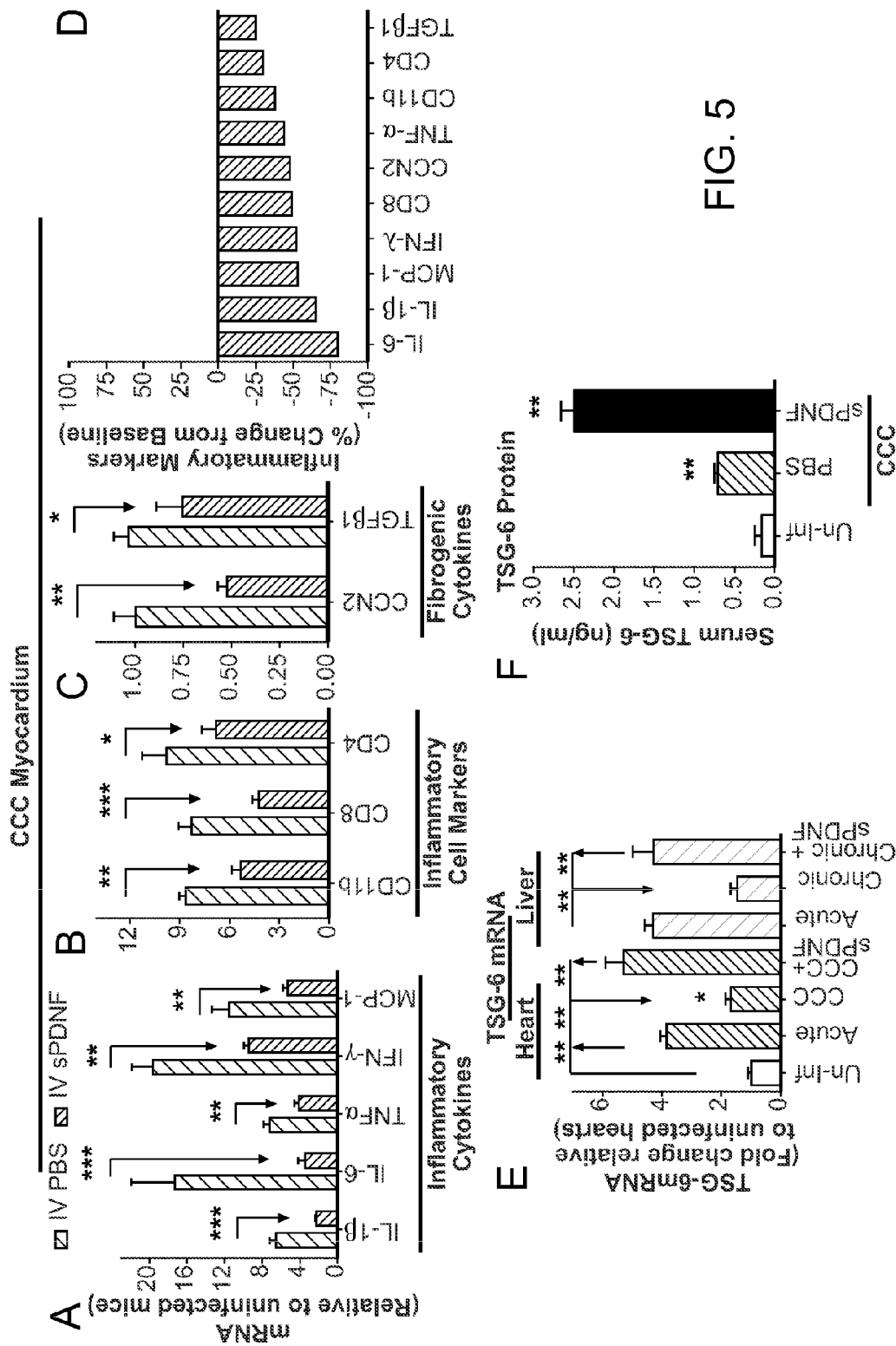
FIGS. 5A-5F show that intravenous sPDNF triggered a global decrease in the transcripts of cardiac inflammatory and fibrogenic markers, and increased expression of the anti-inflammatory TSG-6 in the heart and liver of mice with chronic Chagas cardiomyopathy (CCC).

FIG. 5 shows that intravenous administration of soluble PDNF (sPDNF) triggered a global decrease in the transcripts of cardiac inflammatory and fibrogenic markers, and increased expression of the anti-inflammatory TSG-6 in the heart and liver of mice with chronic Chagas cardiomyopathy (CCC).

Example 2. Use of sPDNF for Treatment of Inflammatory Bowel Disease (IBD)

In this example, a mouse model of IDB is used, and the regenerative chemotherapeutic profile is determined to assess the effect of sPDNF administration.

Figure 6:
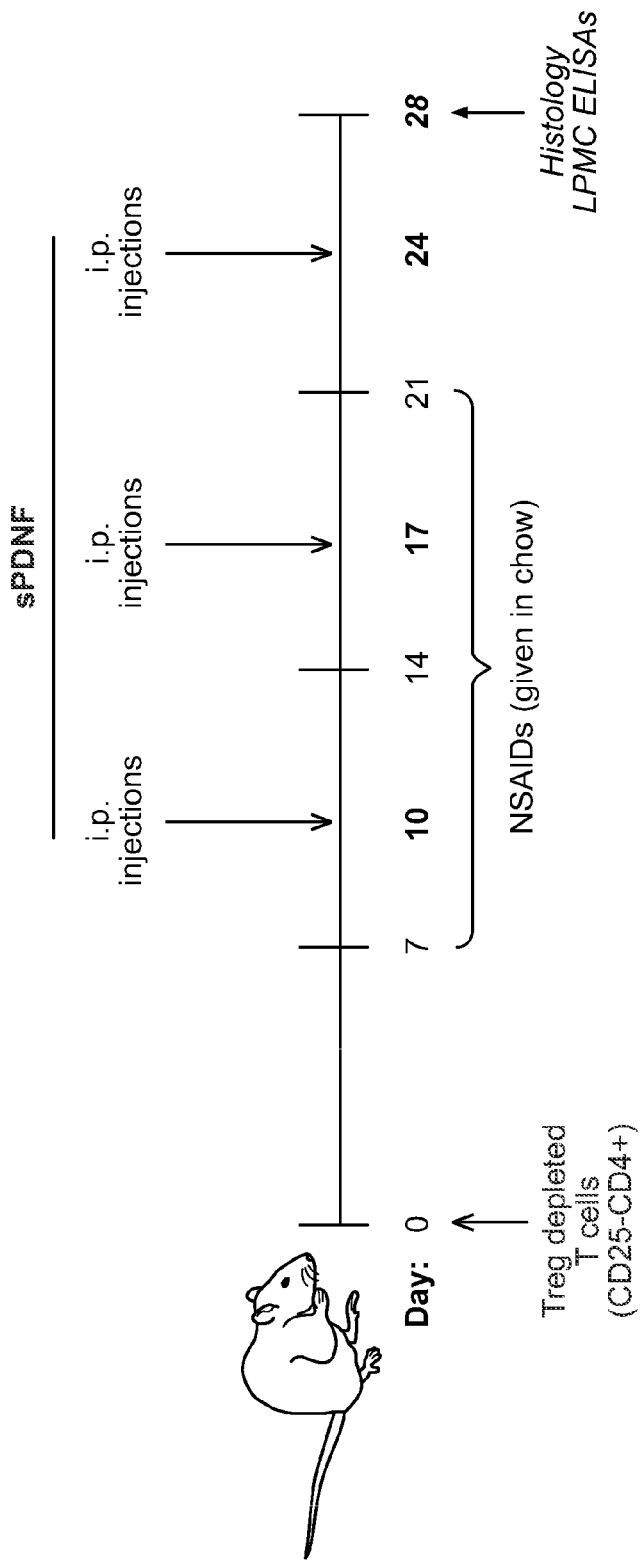
FIG. 6 illustrates a treatment scheme for treating IBD with sPDNF. sPDNF, at the dose of 1 mg/kg per injection, is administered intraperitoneally at 0 hr, 3 hr, and 24 hr, one day per week for 3 weeks, on day 10, day 17, and day 24, as indicated by the arrows.

Rag 2$^{-/-}$ mice (from Jackson Laboratories) are administered intraperitoneally 1×10$^5$ CD4$^+$CD25$^-$ splenic T cells from C57BL/6 mice (from Jackson Laboratories). CD4$^+$CD25$^-$ T cells are isolated by fluorescence cell sorting. One week after T cell transfer, Rag mice are administered piroxicam, a nonsteroidal anti-inflammatory drug (NSAID), mixed into their feed for 2 weeks (42 mg piroxicam/250 g chow, week 1; 62 mg piroxicam/250 g chow, week 2). The piroxicam (Sigma-Aldrich) is stopped, and colitis is studied 1 week later. Intraperitoneal (i.p.) injection of sPDNF is given in accord with the scheme as shown in FIG. 6. Animals are sacrificed 4 weeks from the day of cell transfer. Colons are isolated, and half of the colons divided longitudinally are fixed, sectioned, and stained with H&E for microscopic examination to score the severity of colitis. The other half is dissociated with collagenase to isolate lamina propria mononuclear cells (LPMC), which are analyzed by flow cytometry and cultured in vitro to determine levels of inflammatory cytokines.

Figure 7:
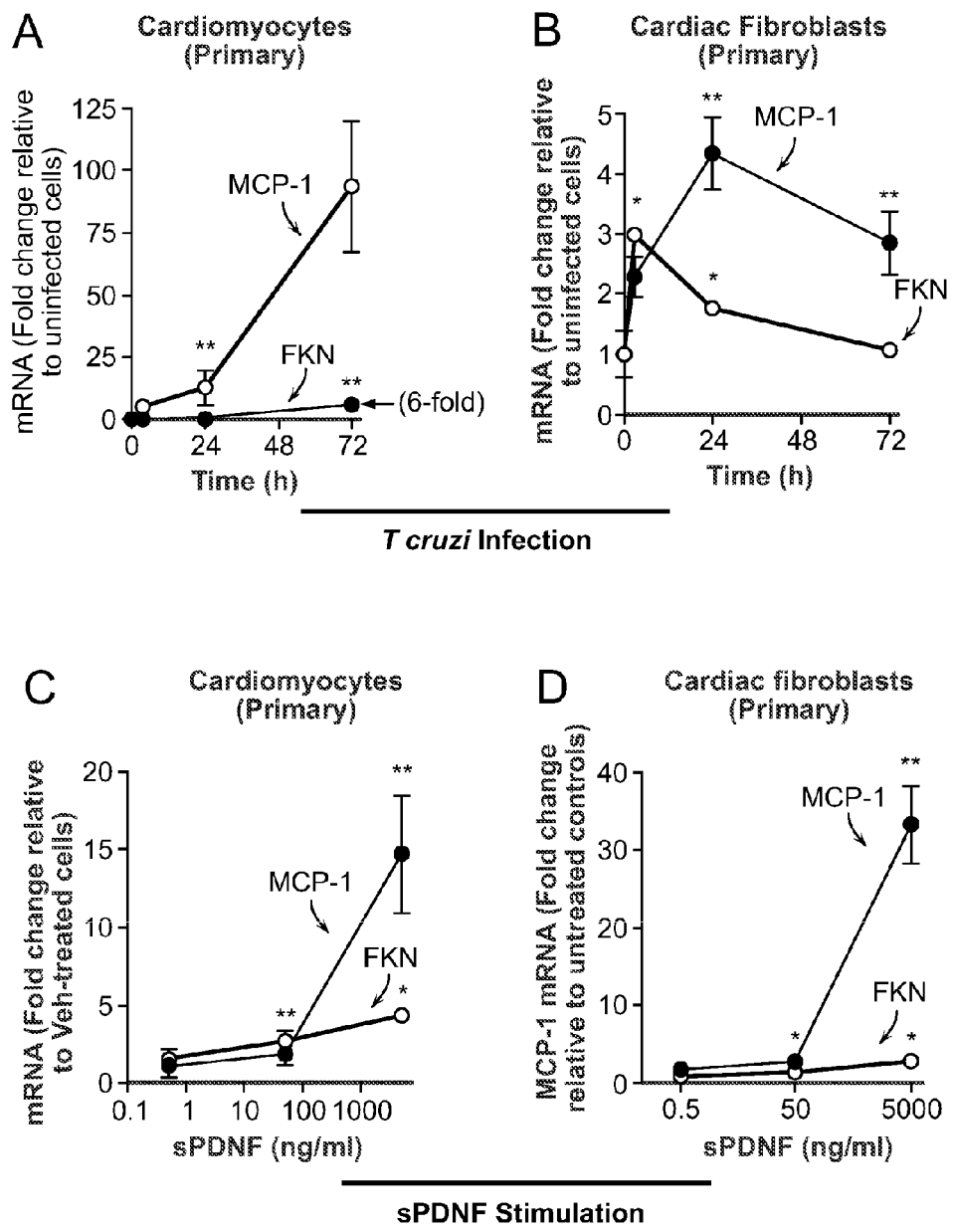
FIGS. 7A-7D show that both *T cruzi* and sPDNF increased expression of MCP-1 and FKN transcripts in primary cultures of cardiomyocytes and cardiac fibroblasts.

Example 3. T cruzi and sPDNF Augmented Expression of MCP-1 and FKN in Cardiomyocytes and Cardiac Fibroblasts Whether T cruzi and sPDNF augment the expression of chemokines in cardiomyocytes and cardiac fibroblasts was determined, focusing on MCP-1 and FKN. In line with, and extending an earlier study (26), T cruzi infection of primary cardiomyocytes and cardiac fibroblasts increased expression of MCP-1 and FKN transcripts in a time-dependent manner (FIGS. 7A and 7B). In addition, the stimulatory activity of T cruzi was mimicked by sPDNF, which stimulated an increase in MCP-1 and FKN transcripts in both primary cardiomyocytes and cardiac fibroblasts in a dose-dependent manner (FIGS. 7B and 7C).

Figure 8:
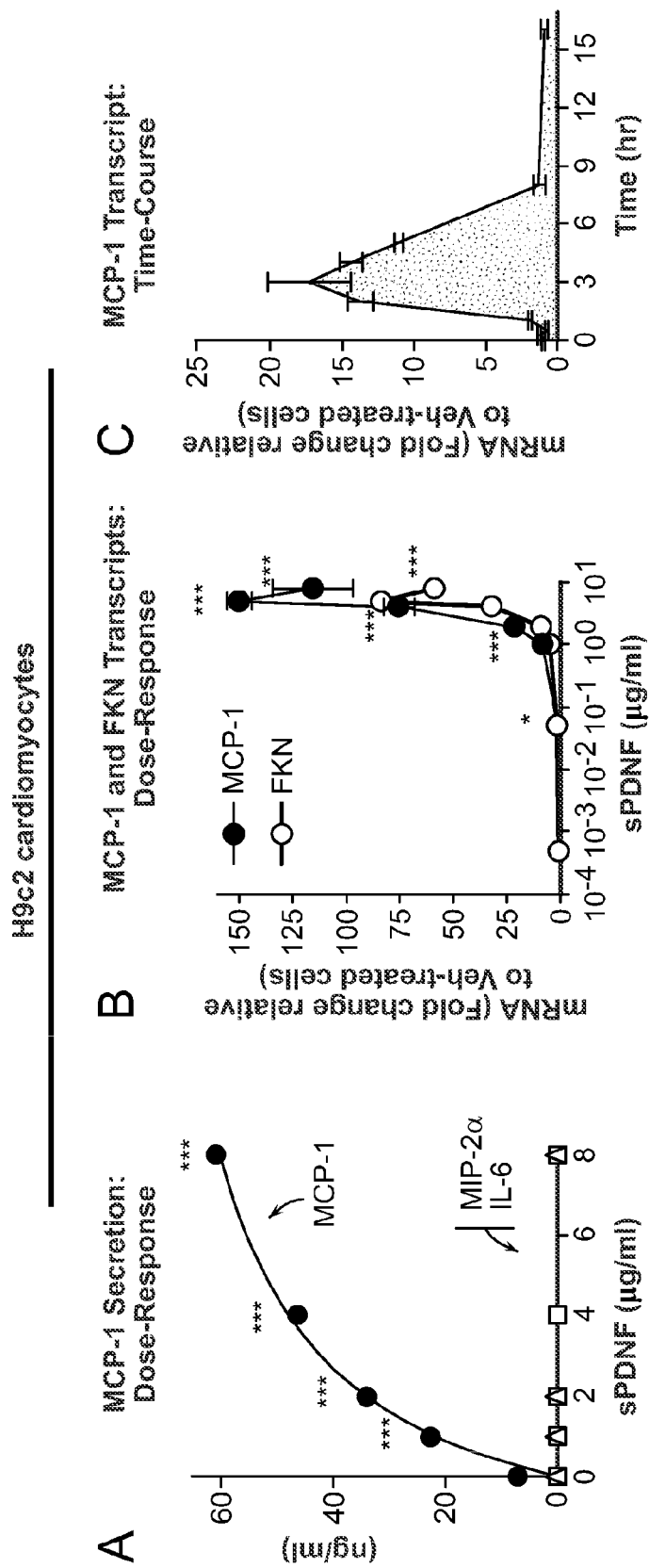
FIGS. 8A-8C show that sPDNF increased MCP-1 and FKN expression in H9c2 cardiomyocytes dose-dependently and in a pulse-like manner.

In the cardiomyocyte cell line H9c2, sPDNF dramatically increased secretion of MCP-1 dose-dependently (FIG. 8A) and specifically, as sPDNF did not alter secretion of another chemokine, macrophage inflammatory protein-2a/MIP-2a/CXCL2, and of the cytokine IL-6 (FIG. 8A). Similar to the results obtained with primary cardiomyocytes, the increase in MCP-1 and FKN mRNA in H9c2 cardiomyocytes was dose-dependent (FIG. 8B). Furthermore, time-course analysis revealed that MCP-1 transcript increased maximally 3 hr after sPDNF stimulation and dropped sharply to levels similar to unstimulated cells after 8 hr, with typical pulse-like kinetics (FIG. 8C).

Example 4. Targeting Cardiomyocyte Neurotrophin Receptors TrkA and TrkC Increased Expression of MCP-1 and FKN Three distinct characteristics were used to determine whether T cruzi PDNF exploits TrkA or TrkC, or both, to increase MCP-1 and FKN production in cardiac cells. First, H9c2 cardiomyocytes were pre-incubated (1 hr) with the Trk antagonist K252a, which blocks Trk signaling by inhibiting Trk autophosphorylation (53), followed by stimulation (3 hr) with sPDNF (1 µg/ml) or vehicle PBS, and quantification of MCP-1 and FKN transcripts by qPCR. K252a completely abrogated the stimulatory effect of sPDNF (FIGS. 9A and 9B), indicating that the agonistic effect of sPDNF required Trk signaling.

Second, cardiomyocytes were pre-incubated (0.5 hr) with neutralizing antibodies against neurotrophin receptors prior to stimulation with sPDNF (1 µg/ml, 3 hr). Without being bound to a particular theory, if sPDNF uses Trk receptors to augment chemokine expression, then neutralizing the receptors with antibodies against the extracellular domain of the receptors will prevent access of sPDNF to the receptors and block sPDNF stimulation of MCP-1 and FKN expression. Antibodies against TrkA (α-TrkA+sPDNF) significantly blocked sPDNF-induced upregulation (+sPDNF) of MCP-1 (29.2±3.5% inhibition) and FKN (29.5±5.3% inhibition), as did antibodies against TrkC (MCP-1 inhibition, 53±2.3%; FKN inhibition, 47.5±1.3%) (FIGS. 9C and 9D). In contrast, neutralizing antibodies against TrkB (a-TrkB+sPDNF) were ineffective in preventing sPDNF upregulation of both MCP-1 and FKN (FIGS. 9C and 9D), consistent with the previous finding that TrkB was not recognized by sPDNF, thus serving as a negative control for the α-TrkA and α-TrkC inhibition experiments (12, 59).

Third, experiments were designed to reduce Trk expression with short hairpin mRNA (shRNA) to further validate the conclusion that enhanced expression of MCP-1 and FKN resulted from the binding of sPDNF to TrkA and TrkC. For this purpose H9c2 cardiomyocytes were transfected with lentivirus encoding shRNA for control green fluorescence protein (shGFP), TrkA (four distinct vectors), or TrkC (five distinct vectors). Untransfected and transfected myocytes were stimulated with sPDNF (1 µg/ml, 3 hr), and the inhibitory effect of gene silencing was assessed by comparing secreted MCP-1 levels in sPDNF-stimulated cells with those of vehicle PBS-treated cells. Compared to GFP-transfected cardiomyocytes or untransfected cardiomyocytes, cardiomyocytes transfected with shTrkA or shTrkC constructs significantly blocked MCP-1 secretion in response to sPDNF stimulation (FIG. 9E).

Thus, on the basis of these three characteristics that operate by distinct mechanisms, it was concluded that sPDNF used both TrkA and TrkC to increase expression of MCP-1 and FKN, akin to the utilization of TrkA by the matricellular protein CTGF/CCN2 to increase expression MCP-1 in cardiomyocytes (58). Notably, dual usage of TrkA and TrkC to increase expression of MCP-1 and FKN is analogous to neuronal cell invasion, which depends on both TrkA (18) and TrkC (60). However, dual usage of TrkA and TrkC to increase expression of MCP-1 and FKN was contrary to the mechanism of T cruzi entry into cardiac fibroblasts or cardiomyocytes, which depends on TrkC (5), and contrary to sPDNF-induced NGF secretion by cardiomyocytes, which is selective for TrkA (4).

Figure 10:
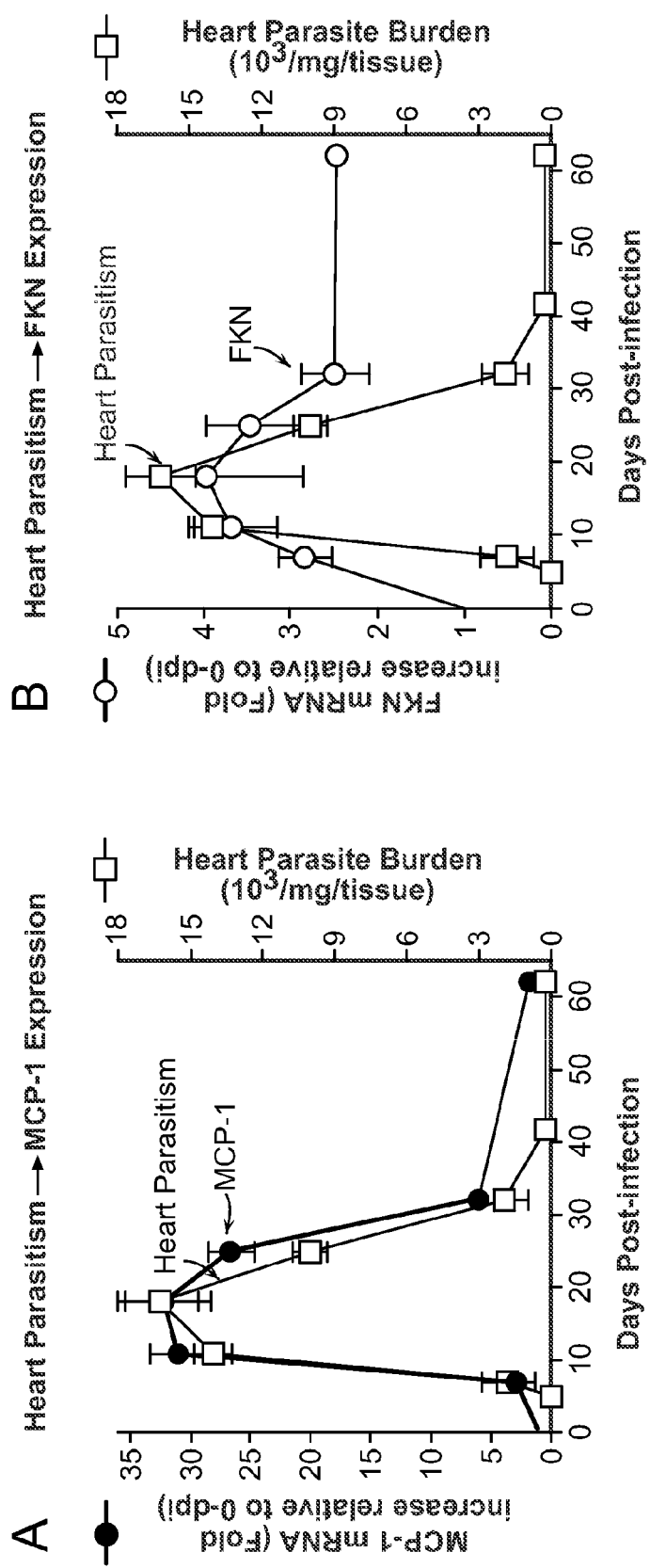
FIGS. 10A and 10B show that MCP-1 and FKN mRNAs increased in acute chagasic hearts in proportion to parasite burden.

Example 5. Cardiac MCP-1 and FKN have Increased Expression in a Mouse Model of Acute Chagas Myocarditis Groups of three mice were infected with T cruzi (Tulahuen strain), sacrificed at several days postinfection (PI). Cardiac MCP-1 and FKN mRNAs and cardiac parasite burden were quantified by qPCR (4, 5, 17, 18, 60). In line with a previous study (34), the levels of MCP-1 and FKN mRNA paralleled the degree of heart parasite burden (FIGS. 10A and 10B). However, unlike MCP-1, expression of FKN transcripts remained significantly elevated for at least 20 days after cardiac parasitism becomes barely detectable (FIG. 10B). Without being bound to a particular theory, this result is in agreement with the view that FKN plays an important role in recruiting blood monocytes that promote cardiac healing after myocardial injury (33).

Example 6. A Single Dose of Intravenous sPDNF Increased MCP-1 and FKN Expression in the Heart Dose-Dependently and with Pulse-Like Kinetics in Both Naive Wild Type and MyD88$^{-/-}$ Mice The robust MCP-1 increase in acutely infected hearts (FIG. 10A) was likely due to the stimulation of TLRs and other canonical pro-inflammatory pathways by T cruzi molecules, exemplified by glycosylphosphatidylinositol-anchored mucin-like glycoproteins. GPI-anchored mucin-like glycoproteins increase MCP-1 and mediate leukocyte recruitment in the pleural cavity of mice primed with an IFN-γ-inducing agent (16). Without being bound to a particular theory, if T cruzi-PDNF is also a mechanism responsible for triggering MCP-1 expression in T cruzi-infected hearts, then intravenous (IV) administration of sPDNF should increase expression of chemokines MCP-1 and FKN in the heart of uninfected, naive mice. A previous pharmacokinetics study showed that sPDNF administered IV into naive mice has a half-life of ~15 min in the blood and peaks in the myocardium ~15 min post-injection, triggering cardiac responses such as NGF upregulation hours after injection (4).

Figure 9:
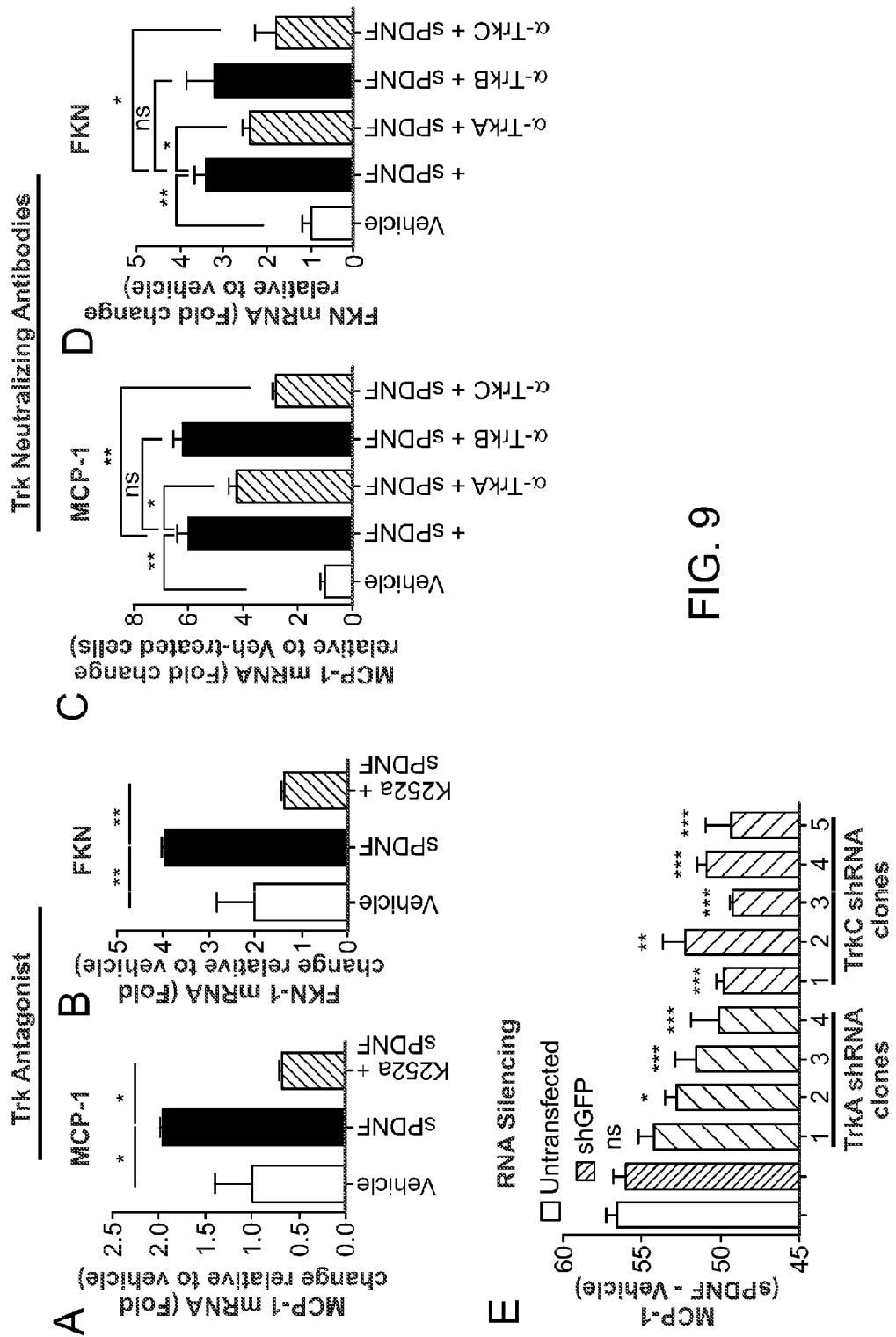
FIG. 9 shows that neurotrophic receptors TrkA and TrkC were targeted by sPDNF for increased expression of MCP-1 and FKN in cardiomyocytes.
Figures 11A, 11B, 11C:
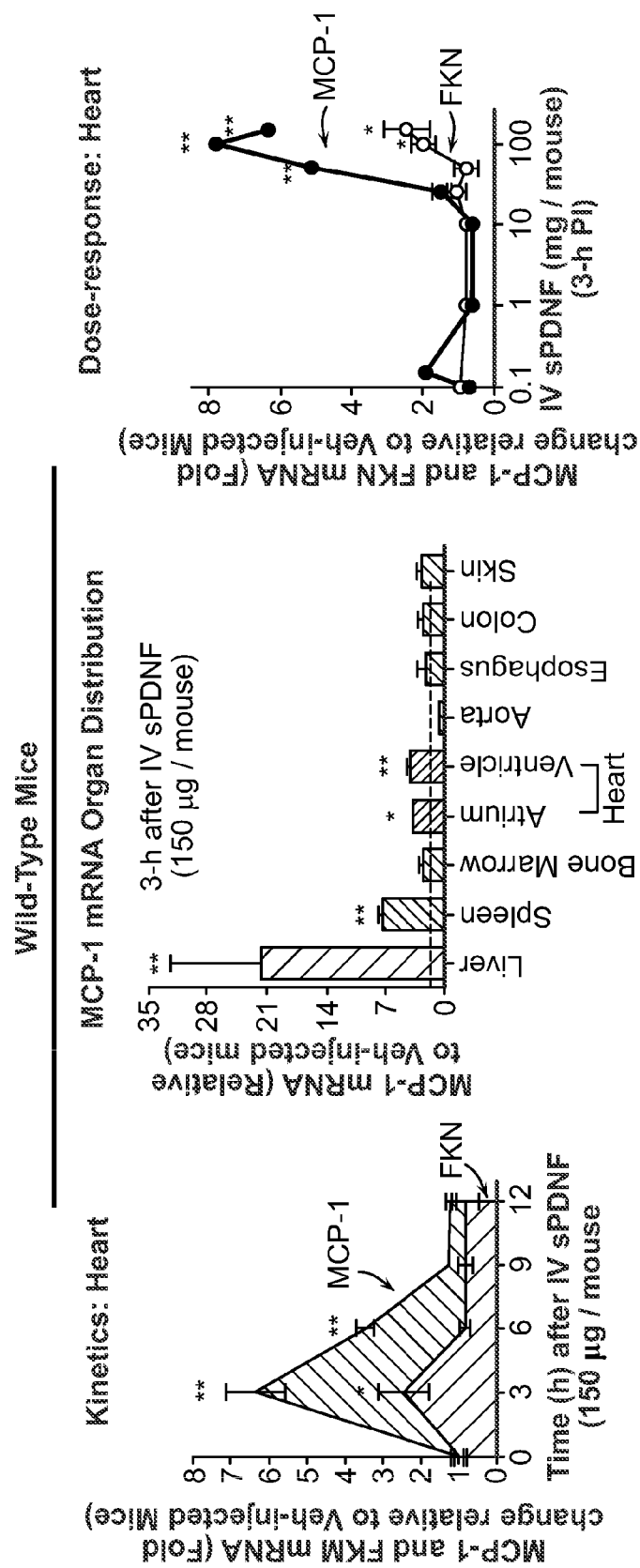
FIGS. 11A-11H show that intravenous sPDNF increased expression of MCP-1 and FKN in the heart and other organs of wild type and MyD88$^{-/-}$ mice. Wild type C57BL/6 mice were used in the results depicted in FIGS. 11A-11D.
Figures 11D, 11E, 11F, 11G, 11H:
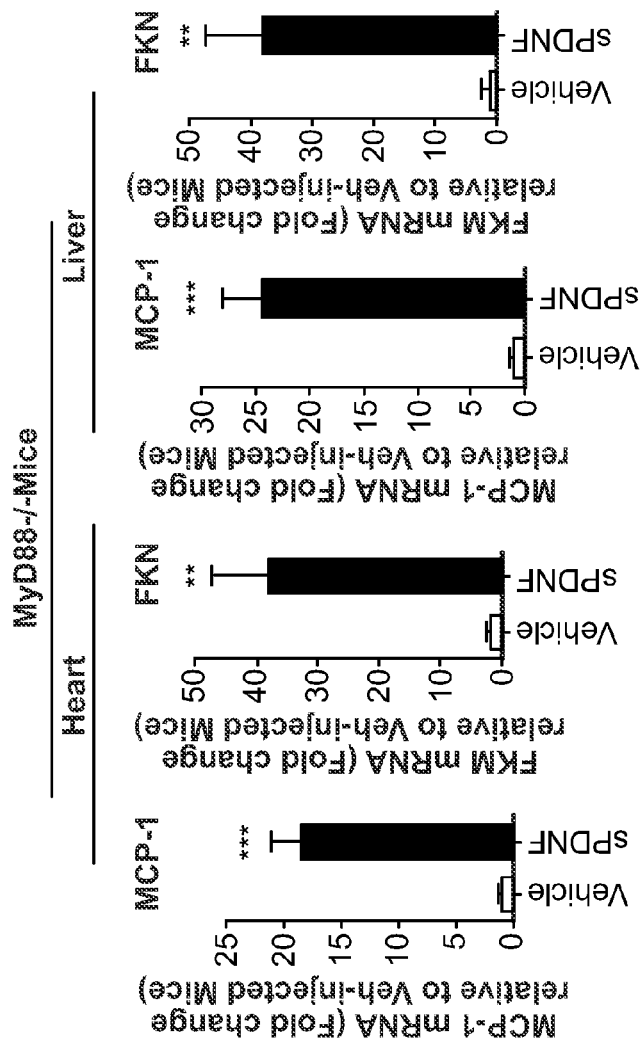

Groups of naive wild type C57BL/6 mice were injected with vehicle (PBS) or a single dose of IV sPDNF. Mice were sacrificed at various timepoints post-injection, and heart MCP-1 and FKN expression measured by real time PCR. Administration of IV sPDNF significantly increased expression of both cardiac MCP-1 and FKN transcripts with pulse-like kinetics. Both chemokines peaked shortly after administration (3 hr post-injection) and quickly decreased to levels observed in un-injected mice (FIG. 11A). The agonist effect of IV sPDNF was screened in various organs using optimum time response (3 hr post-injection) using the same dose as in FIG. 11A. Treatment with sPDNF increased expression of MCP-1 not only in the heart, liver (where the response was most robust) and spleen, but not in the bone marrow, aorta, esophagus, colon and skin (FIG. 11B). Organ distribution of MCP-1 expression in response to IV sPDNF was similar to that of FKN. Without being bound to a particular theory, the selective increase of MCP-1 and FKN in various organs may reflect the uneven expression of PDNF receptors TrkA and TrkC in neural and non-neural tissues (22, 50). Furthermore, increased expression of MCP-1 and FKN triggered by IV sPDNF was dose-dependent in the heart (FIG. 11C) and liver (FIG. 11D). Without being bound to a particular theory, this result is in agreement with the hypothesis that sPDNF stimulates MCP-1 and FKN through a receptor (TrkA and TrkC)-mediated process, akin to the results obtained for cardiac cells in culture (FIG. 9).

The sPDNF preparations did not have detectable levels of endotoxin (as assessed by the Limulus amebocyte assay), and were non-toxic in recombinase-activating gene-2 (RAG-2$^{-/-}$)-deficient mice, which are highly susceptible to endotoxin shock (42). To ensure that the response observed in wild type mice was not due to TLR activation, MCP-1 and FKN response to IV sPDNF was assessed in TLR-deficient MyD88$^{-/-}$ mice (23). Accordingly, the results showed that IV sPDNF gave rise to a sharp increase in the expression of both MCP-1 and FKN in the heart and liver of MyD88$^{-/-}$ mice (FIGS. 11E-11H). Without being bound to a particular theory, this indicates that sPDNF acts on the Trk receptors independently of TLR signaling.

Figure 12:
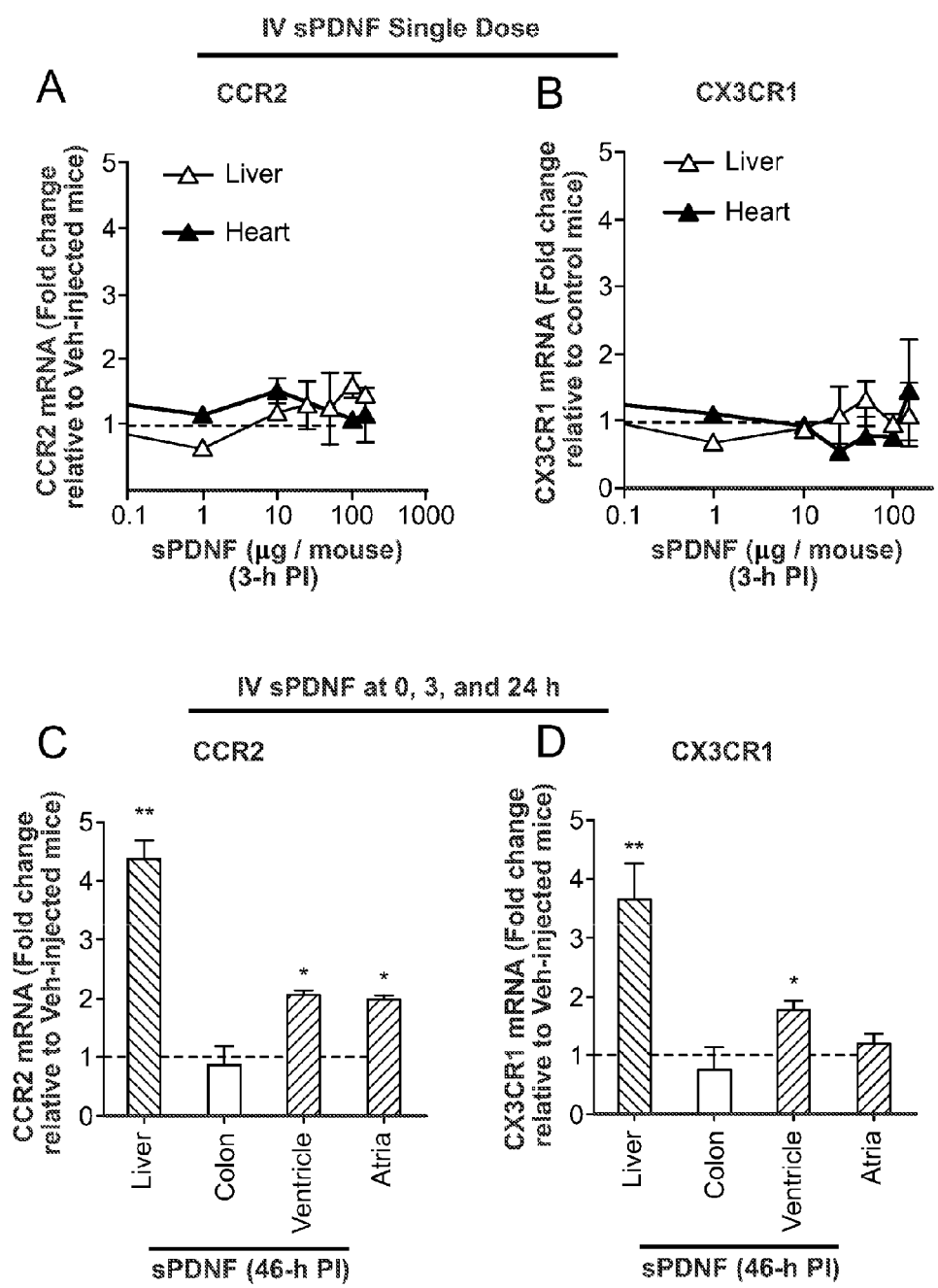
FIGS. 12A-12D show that multiple intravenous injections of sPDNF increased transcripts of MCP-1 and FKN receptors CCR2 and CX3CR1 in the heart and liver. For the results depicted in FIGS. 12A and 12B, mice (3/group) were injected with various single doses of IV sPDNF, and sacrificed 3 hr post-injection.

Example 7. Multiple Doses of IV sPDNF Increased Expression of MCP-1 and FKN Receptors CCR2 and CX3CR1 in the Mouse Heart and Liver One of the functions of MCP-1 and FKN is to attract cells expressing their receptors (CCR2 and CX3CR1, respectively) to tissue sites. Following a single IV sPDNF dose (150 μg), CCR2 and CX3CR1 transcripts did not increase in cardiac and hepatic tissues (FIGS. 12A and 12B), consistent with the finding that MCP-1 and FKN increase was transient and pulse-like (FIG. 11A). However, sustained tissue exposure to sPDNF obtained by multiple and closely spaced systemic sPDNF injections into naïve mice (IV sPDNF at times 0, 3 and 24 hr, measuring chemokines 24 hr after the last injection), resulted in a significant increase in CCR2 and CX3CR1 in the liver and heart (ventricle and atrium) (FIGS. 12C and 12D). Thus, sPDNF-induced MCP-1 and FKN promoted migration of cells bearing CCR2 and CX3CR1 receptors.

The results described herein were obtained using the following materials and methods.

Purification of Recombinant sPDNF

PDNF was cloned from the T cruzi Silvio X-10/4 strain (GenBank accession number AJ002174). PDNF and a N-terminal short-form of PDNF (sPDNF) that contains Trk-binding sites, were expressed in BL21 (DE3) bacteria, and purified by Ni-affinity chromatography, as described previously (4, 12, 18, 60). Buffers were prepared in sterile endotoxin-free water, and sPDNF preparations screened with the Limulus amebocyte assay have undetectable levels of endotoxin. sPDNF migrates as a 68 kDa protein on a SDS-PAGE gel. PDNF protein was buffer exchanged into PBS (0.01 M phosphate buffered saline, pH 7.2), filter-sterilized (0.22 μm), and kept at 4° C. PDNF was quantified by scanning densitometry (Bio-Rad, GS-800) of SDS-PAGE gels stained with Coomassie brilliant blue.

Parasites

Experiments were performed with *T. cruzi* Tulahuen strain, which were propagated in Vero cells. Free-swimming infective trypomastigotes were harvested from supernatants (3-5 days after infection) by initial low speed centrifugation (500×g, 5 min) to remove host cells and debris, followed by high-speed centrifugation (1,200×g, 10 min) to pellet parasites, and resuspended in DMEM/0.1% FCS. For in vivo experiments, parasites were resuspended in PBS prior to injection into mice.

Mice

Female C57BL/6 mice, 6-8 weeks of age and C57BL/6 breeding pairs were from the Jackson Laboratory (Bar Harbor, Me.). MyD88-knockout mice were a generous gift from Dr. Thereza Imanishi-Kari, Tufts Medical School (21). All mouse experiments were approved by the Institutional Animal Care and Use Committee (IACUC) and the Division of Laboratory Animal Medicine (DLAM) of Tufts University School of Medicine.

Cell Lines and Primary Cell Cultures (i) Cell Lines.

H9c2 (ATCC® CRL-1446) (rat cardiomyocyte) and HEK 293 cells (used generate lentiviral particles) were maintained in DMEM/10% FCS, and Vero cells (used to grow *T cruzi*) in DMEM/1% FCS. Cells were incubated at 37° C. in a humidified atmosphere containing 5% $CO_2$.

(ii) Primary Cardiomyocytes and Cardiac Fibroblasts.

Cells were isolated using a modified version of a previously described procedure (4, 5, 51). In short, neonatal C56BL/6 mice (1-3 days old) were sacrificed by decapitation, their hearts excised and washed twice in PBS, then kept in 20 mM HEPES, 130 mM NaCl, 1 mM $NaH_2PO_4$, 4 mM glucose, 3 mM KCl, pH 7.6 for 10 minutes on ice. Hearts were minced and digested in 0.25% Trypsin-EDTA (Gibco) 3-4 times at 37° C. with periodic mixing. Dissociated cells were pooled and digestion stopped with DMEM/10% FCS, filtered through a 100 ˆm cell strainer, centrifuged at 500×g, and plated for 3 h on 1% gelatin-coated plates in DMEM (Gibco)/F12 Ham's (Sigma) 50:50, 20% FCS (PAA), 5% horse serum (PAA), 2 mM L-glutamine (Gibco), 0.1 mM nonessential amino acids (Gibco), 3 mM sodium pyruvate (Gibco), and 1 ˆg/ml bovine insulin (Sigma) with 1× penicillin-streptomycin (Gibco). Non-adherent cells (cardiomyocytes) were remove and plated onto new gelatin-coated plates while adherent cells (cardiac fibroblasts) remained in the initial plate in DMEM/10% FCS until needed. Cardiomyocytes contained <5% cardiac fibroblasts and vice versa for cardiac fibroblasts, as determined by immunofluorescence using antibodies against the cardiomyocyte marker myosin heavy chain (MHC) and cardiac fibroblast marker vimentin, as described earlier (4).

Cell Stimulation (i) *T cruzi*.

Primary cardiomyocytes and cardiac fibroblasts were seeded at 6-8×10⁴ cells per well in DMEM/10% FCS and allowed to adhere overnight. Media was changed to DMEM/5% FCS and cells were infected with *T cruzi* at an MOI (multiplicity of infection) of 10 for 10-24 h, at which time parasites were washed off. At 3, 24, and 72 hr post-infection (PI), cell monolayers were collected in Trizol reagent (Invitrogen) to isolate RNA to generate cDNA for qPCR.

(ii) sPDNF.

Primary cardiomyocytes and cardiac fibroblasts, and H9c2 cardiomyocytes were seeded at $6-8\times10^4$ cells per well in DMEM/10% FCS and allowed to adhere overnight, serum starved (DMEM/0.1% FCS overnight), and treated with sPDNF (0.5 ng/ml-8 µg/ml, 0-16 h). Cell supernatants were collected and stored at −80° C. and cell monolayers rinsed with PBS and collected in Trizol for qPCR analysis.

Blocking Trk receptors (i) Pharmacological Inhibitor.

H9c2 cells were pre-treated with 0.1% DMSO vehicle control or 200 nM K252a for 1 h prior to addition of sPDNF (1 µg/ml). Supernatants and cell monolayers were collected for quantification of secreted chemokines and cells were harvested for mRNA quantification by qPCR.

(ii) Neutralizing Antibodies.

H9c2 cardiomyocytes were pre-treated with 1 µg/ml neutralizing antibodies against TrkA (a-TrkA, Santa Cruz SC-118), TrkB (a-TrkB, Santa Cruz SC-8316), and TrkC (a-TrkC, Santa Cruz SC-14025) for 30 min, and then stimulated with 1 µg/ml sPDNF; chemokine transcripts were quantified by qPCR.

(iii) Lentiviral Transfection and Trk Knockdown by shRNA.

Lentiviral vectors encoding shRNA constructs targeting TrkA (clones 1-4), TrkC (clones 1-5) or GFP mRNA (Open Biosystems) were generated from transfected HEK 293 cells following manufacturer's instructions, and aliquots were frozen at −80° C. until use. Lentiviral infection of H9c2 cells was performed after pretreatment with 8 µg/ml polybrene (Sigma-Aldrich) in DMEM/10% FCS, with a dose of 200 µl vector-containing supernatant/2 ml medium in 6-well plates. Lentiviral particles were removed 24 hr after infection and, 7-8 d later, cells were serum starved in serum-free DMEM for 2 hr and stimulated without or with sPDNF (4 µg/ml, 3 hr).

Quantitative Real-Time PCR (qPCR)

RNA was isolated from Trizol lysates of cell monolayers or liquid nitrogen snap frozen tissue samples dissociated by a Tissue-Tearor mechanical homogenizer (Biospec Products, Inc.). cDNA was synthesized using the Quantitect Reverse Transcription kit (Qiagen) according to manufacturer's instructions. Chemokine and chemokine receptor transcripts were amplified using specific primers and normalized to HPRT using SYBR Green (Qiagen), and, if needed, expressed relative to control-unstimulated cells. The following primers were used:

```
MCP-1 (F: 5'-TCTCTTCCTCCACCACTATGCA-3' (SEQ ID NO: 7);

R: 5'-GGCTGAGACAGCACGTGGAT-3' (SEQ ID NO: 8)),

FKN (F: 5'-GCCCGCCGAATTCCTGCACT-3' (SEQ ID NO: 9);

R: 5'-CAATGGCACGCTTGCCGCAG-3' (SEQ ID NO: 10)),

CCR2 (F: 5'-AATGAGAAGAAGAGGCACAGGGCT-3' (SEQ ID NO: 11);

R: 5'-ATGGCCTGGTCTAAGTGCTTGTCA-3' (SEQ ID NO: 12)),
```

-continued

```
CX3CR1 (F: 5'-CGACATTGTGGCCTTTGGAACCAT-3' (SEQ ID NO: 13);

R: 5'-AGATGTCAGTGATGCTCTTGGGCT-3' (SEQ ID NO: 14)), and

HPRT (F: 5'-CAGCGTCGTGATTAGCGATGATG-3' (SEQ ID NO: 15);

R: 5'-CGAGCAAGTCTTTCAGTCCTGTC-3' (SEQ ID NO: 16)).
```

Enzyme-Linked Immunosorbent Assay (ELISA)

MCP-1: 96-well Maxisorp plates (Nunc) were coated overnight with relevant supernatants or MCP-1 standards (R&D Systems, 479-JE/CF) in coating buffer (50 mM $NaHCO_3/Na_2CO_3$, pH 9.6, 0.02% $NaN_3$), blocked in 5% BSA/PBST, reacted with a MCP-1 detection antibody (Santa Cruz, SC-28879; 1:200; 2 hr), and then alkaline-phosphatase (AP) conjugated secondary antibody (Sigma A3687; 1:1000; 1 hr). Between each step, plates were washed 2-4 times with PBST. Wells were then incubated with colorigenic AP substrate (Sigma N9389, 1 mg/ml in 100 mM glycine, 1 mM $MgCl_2$, 1 mM $ZnCl_2$, pH 10.4) and absorbance read at 405 nm on an Emax precision microplate reader (Molecular Devices). MCP-1 concentrations were calculated relative to a 4-parametric standard curve using the SOFTmax Pro program. MIP-2a (R&D Systems, DY452) and IL-6 (R&D Systems, DY406) ELISAs were done according to manufacturer's protocols.

Mouse Model of Acute Chagas Disease and Intravenous (IV) sPDNF Administration into Naive Mice (i) Mouse Model.

Female C57BL/6 mice (6-8 weeks old) were infected subcutaneously in the left hind footpad with $5 \times 10^3$ trypomastigotes in 30 µl under isofluorine anesthesia, and sacrificed at various days post-infection (DPI) by $CO_2$ asphyxiation and cervical dislocation. Organs were perfused by intracardiac injection of 5 ml ice-cold PBS, and the heart (sometimes, atria and ventricle were collected separately) and other organs were collected and flash frozen in liquid nitrogen and stored at −80° C. or fixed in 4% paraformaldehyde for frozen sections. Tissue parasitism was quantified using a qPCR method previously described (17, 18, 60).

(ii) IV Administration.

sPDNF was diluted in sterile endotoxin-free PBS (200 µl) and injected via the tail vein into 6-8 week old female C57BL/6 mice. Mice receiving single IV injections of 150 µg sPDNF per mouse were sacrificed at 3, 6, 9, and 12 hr post-injection, or various doses of sPDNF (100 ng-150 µg) and sacrificed 3 hr post-injection. Mice receiving multiple injections of sPDNF or PBS vehicle control (0, 3, and 24 hr, 100 µg per injection) were sacrificed 24 hr after the last injection (i.e., 48 hr after the first injection). Mice were perfused with PBS and organs harvested as described above.

Statistical Analyses

Statistical analysis was performed using GraphPad Prism software (version 5.0) using Student's/-test (for comparing two samples) or one-way ANOVA with Tukey's post-test (for comparing three or more samples).

REFERENCES

1. Aliberti, J. C., M. A. Cardoso, G. A. Martins, R. T. Gazzinelli, L. Q. Vieira, and J. S. Silva. 1996. Interleukin-12 mediates resistance to *Trypanosoma cruzi* in mice and is produced by murine macrophages in response to live trypomastigotes. Infect Immun 64:1961-1967.
2. Almeida, I. C., M. M. Camargo, D. O. Procopio, L. S. Silva, A. Mehlert, L. R. Travassos, R. T. Gazzinelli, and M. A. Ferguson. 2000. Highly purified glycosylphosphatidylinositols from *Trypanosoma cruzi* are potent proinflammatory agents. EMBO J 19:1476-1485.
3. Antunez, M. I., and R. L. Cardoni. 2000. IL-12 and IFN-gamma production, and NK cell activity, in acute and chronic experimental *Trypanosoma cruzi* infections. Immunol Lett 71:103-109.
4. Aridgides, D., R. Salvador, and M. PereiraPerrin. 2013. *Trypanosoma cruzi* Coaxes Cardiac Fibroblasts into Preventing Cardiomyocyte Death by Activating Nerve Growth Factor Receptor TrkA. PLoS ONE 8:e57450.
5. Aridgides, D., R. Salvador, and M. Pereiraperrin. 2013. *Trypanosoma cruzi* highjacks TrkC to enter cardiomyocytes and cardiac fibroblasts while exploiting TrkA for cardioprotection against oxidative stress. Cell Microbiol 15:1357-1366.
6. Bastos, C. J., R. Aras, G. Mota, F. Reis, J. P. Dias, R. S. de Jesus, M. S. Freire, E. G. de Araujo, J. Prazeres, and M. F. Grassi. 2010. Clinical outcomes of thirteen patients with acute chagas disease acquired through oral transmission from two urban outbreaks in northeastern Brazil. PLoS Negl Trop Dis 4:e711.
7. Bastos, K. R., R. Barboza, L. Sardinha, M. Russo, J. M. Alvarez, and M. R. Lima. 2007. Role of endogenous IFN-gamma in macrophage programming induced by IL-12 and IL-18. Journal of interferon & cytokine research: the official journal of the International Society for Interferon and Cytokine Research 27:399-410.
8. Camargo, M. M., I. C. Almeida, M. E. Pereira, M. A. Ferguson, L. R. Travassos, and R. T. Gazzinelli. 1997. Glycosylphosphatidylinositol-anchored mucin-like glycoproteins isolated from *Trypanosoma cruzi* trypomastigotes initiate the synthesis of proinflammatory cytokines by macrophages. J Immunol 158:5890-5901.
9. Chessler, A. D., L. R. Ferreira, T. H. Chang, K. A. Fitzgerald, and B. A. Burleigh. 2008. A novel IFN regulatory factor 3-dependent pathway activated by trypanosomes triggers IFN-beta in macrophages and fibroblasts. J Immunol 181:7917-7924.
10. Chuenkova, M. V., and M. A. Pereira. 2003. PDNF, a human parasite-derived mimic of neurotrophic factors, prevents caspase activation, free radical formation, and death of dopaminergic cells exposed to the Parkinsonism-inducing neurotoxin MPP+. Brain Res Mol Brain Res 119:50-61.
11. Chuenkova, M. V., and M. A. Pereira. 2000. A trypanosomal protein synergizes with the cytokines ciliary neurotrophic factor and leukemia inhibitory factor to prevent apoptosis of neuronal cells. Mol Biol Cell 11:1487-1498.
12. Chuenkova, M. V., and M. PereiraPerrin. 2004. Chagas' disease parasite promotes neuron survival and differentiation through TrkA nerve growth factor receptor. J Neurochem 91:385-394.
13. Chuenkova, M. V., and M. PereiraPerrin. 2005. A synthetic peptide modeled on PDNF, Chagas' disease parasite neurotrophic factor, promotes survival and differentiation of neuronal cells through TrkA receptor. Biochemistry 44:15685-15694.

14. Chuenkova, M. V., and M. PereiraPerrin. 2009. *Trypanosoma cruzi* targets Akt in host cells as an intracellular antiapoptotic strategy. Sci Signal 2:ra74.
15. Chuenkova, M. V., and M. Pereiraperrin. 2010. *Trypanosoma cruzi*-Derived Neurotrophic Factor: Role in Neural Repair and Neuroprotection. Journal of neuroparasitology 1:55-60.
16. Coelho, P. S., A. Klein, A. Talvani, S. F. Coutinho, O. Takeuchi, S. Akira, J. S. Silva, H. Canizzaro, R. T. Gazzinelli, and M. M. Teixeira. 2002. Glycosylphosphatidylinositol-anchored mucin-like glycoproteins isolated from *Trypanosoma cruzi* trypomastigotes induce in vivo leukocyte recruitment dependent on MCP-1 production by IFN-gamma-primed-macrophages. J Leukoc Biol 71:837-844.
17. Cummings, K. L., and R. L. Tarleton. 2003. Rapid quantitation of *Trypanosoma cruzi* in host tissue by real-time PCR. Mol Biochem Parasitol 129:53-59.
18. de Melo-Jorge, M., and M. PereiraPerrin. 2007. The Chagas' disease parasite *Trypanosoma cruzi* exploits nerve growth factor receptor TrkA to infect mammalian hosts. Cell host & microbe 1:251-261.
19. Frangogiannis, N. G. 2012. Matricellular proteins in cardiac adaptation and disease. Physiological reviews 92:635-688.
20. Goncalves, V. M., K. C. Matteucci, C. L. Buzzo, B. H. Miollo, D. Ferrante, A. C. Torrecilhas, M. M. Rodrigues, J. M. Alvarez, and K. R. Bortoluci. 2013. NLRP3 controls *Trypanosoma cruzi* infection through a caspase-1-dependent IL-1R-independent NO production. PLoS Negl Trop Dis 7:e2469.
21. Han, J. H., S. Akira, K. Calame, B. Beutler, E. Selsing, and T. Imanishi-Kari. 2007. Class switch recombination and somatic hypermutation in early mouse B cells are mediated by B cell and Toll-like receptors. Immunity 27:64-75.
22. Huang, E. J., and L. F. Reichardt. 2003. Trk receptors: roles in neuronal signal transduction. Annu Rev Biochem 72:609-642.
23. Kawai, T., and S. Akira. 2007. TLR signaling. Seminars in immunology 19:24-32.
24. Koga, R., S. Hamano, H. Kuwata, K. Atarashi, M. Ogawa, H. Hisaeda, M. Yamamoto, S. Akira, K. Himeno, M. Matsumoto, and K. Takeda. 2006. TLR-dependent induction of IFN-beta mediates host defense against *Trypanosoma cruzi*. J Immunol 177:7059-7066.
25. Machado, F. S., W. O. Dutra, L. Esper, K. J. Gollob, M. M. Teixeira, S. M. Factor, L. M. Weiss, F. Nagajyothi, H. B. Tanowitz, and N. J. Garg. 2012. Current understanding of immunity to *Trypanosoma cruzi* infection and pathogenesis of Chagas disease. Seminars in immunopathology 34:753-770.
26. Machado, F. S., G. A. Martins, J. C. Aliberti, F. L. Mestriner, F. Q. Cunha, and J. S. Silva. 2000. *Trypanosoma cruzi*-infected cardiomyocytes produce chemokines and cytokines that trigger potent nitric oxide-dependent trypanocidal activity. Circulation 102:3003-3008.
27. Marin-Neto, J. A., E. Cunha-Neto, B. C. Maciel, and M. V. Simoes. 2007. Pathogenesis of chronic Chagas heart disease. Circulation 115:1109-1123.
28. Martins, R. F., P. M. Martinelli, P. M. Guedes, B. da Cruz Padua, F. M. Dos Santos, M. E. Silva, M. T. Bahia, and A. Talvani. 2013. Protein deficiency alters CX3CL1 and endothelin-1 in experimental *Trypanosoma cruzi*-induced cardiomyopathy. Tropical medicine & international health: TM & IH 18:466-476.
29. Michailowsky, V., N. M. Silva, C. D. Rocha, L. Q. Vieira, J. Lannes-Vieira, and R. T. Gazzinelli. 2001. Pivotal role of interleukin-12 and interferon-gamma axis in controlling tissue parasitism and inflammation in the heart and central nervous system during *Trypanosoma cruzi* infection. Am J Pathol 159:1723-1733.
30. Morganti, J. M., K. R. Nash, B. A. Grimmig, S. Ranjit, B. Small, P. C. Bickford, and C. Gemma. 2012. The soluble isoform of CX3CL1 is necessary for neuroprotection in a mouse model of Parkinson's disease. J Neurosci 32:14592-14601.
31. Morimoto, H., M. Hirose, M. Takahashi, M. Kawaguchi, H. Ise, P. E. Kolattukudy, M. Yamada, and U. Ikeda. 2008. MCP-1 induces cardioprotection against ischaemia/reperfusion injury: role of reactive oxygen species. Cardiovascular research 78:554-562.
32. Morimoto, H., M. Takahashi, A. Izawa, H. Ise, M. Hongo, P. E. Kolattukudy, and U. Ikeda. 2006. Cardiac overexpression of monocyte chemoattractant protein-1 in transgenic mice prevents cardiac dysfunction and remodeling after myocardial infarction. Circ Res 99:891-899.
33. Nahrendorf, M., F. K. Swirski, E. Aikawa, L. Stangenberg, T. Wurdinger, J. L. Figueiredo, P. Libby, R. Weissleder, and M. J. Pittet. 2007. The healing myocardium sequentially mobilizes two monocyte subsets with divergent and complementary functions. J Exp Med 204: 3037-3047.
34. Paiva, C. N., R. T. Figueiredo, K. Kroll-Palhares, A. A. Silva, J. C. Silverio, D. Gibaldi, S. Pyrrho Ados, C. F. Benjamim, J. Lannes-Vieira, and M. T. Bozza. 2009. CCL2/MCP-1 controls parasite burden, cell infiltration, and mononuclear activation during acute *Trypanosoma cruzi* infection. J Leukoc Biol 86:1239-1246.
35. Parada, H., H. A. Carrasco, N. Anez, C. Fuenmayor, and I. Inglessis. 1997. Cardiac involvement is a constant finding in acute Chagas' disease: a clinical, parasitological and histopathological study. Int J Cardiol 60:49-54.
36. Parodi, A. J., G. D. Pollevick, M. Mautner, A. Buschiazzo, D. O. Sanchez, and A. C. Frasch. 1992. Identification of the gene(s) coding for the trans-sialidase of *Trypanosoma cruzi*. EMBO J 11:1705-1710.
37. Pereira, M. E. 1983. A developmentally regulated neuraminidase activity in *Trypanosoma cruzi*. Science 219:1444-1446.
38. Pereira, M. E., M. A. Loures, F. Villalta, and A. F. Andrade. 1980. Lectin receptors as markers for *Trypanosoma cruzi*. Developmental stages and a study of the interaction of wheat germ agglutinin with sialic acid residues on epimastigote cells. J Exp Med 152:1375-1392.
39. Pinto, A. Y., A. G. Ferreira, Jr., C. Valente Vda, G. S. Harada, and S. A. Valente. 2009. Urban outbreak of acute Chagas disease in Amazon region of Brazil: four-year follow-up after treatment with benznidazole. Revista panamericana de salud publica=Pan American journal of public health 25:77-83.
40. Prioli, R. P., J. S. Mejia, T. Aji, M. Aikawa, and M. E. Pereira. 1991. *Trypanosoma cruzi*: localization of neuraminidase on the surface of trypomastigotes. Trop Med Parasitol 42:146-150.
41. Rassi, A., Jr., A. Rassi, and J. A. Marin-Neto. 2010. Chagas disease. Lancet 375:1388-1402.
42. Reid, R. R., A. P. Prodeus, W. Khan, T. Hsu, F. S. Rosen, and M. C. Carroll. 1997. Endotoxin shock in antibody-deficient mice: unraveling the role of natural antibody and complement in the clearance of lipopolysaccharide. J Immunol 159:970-975.

43. Rodrigues, A. A., J. S. Saosa, G. K. da Silva, F. A. Martins, A. A. da Silva, C. P. Souza Neto, C. V. Horta, D. S. Zamboni, J. S. da Silva, E. A. Ferro, and C. V. da Silva. 2012. IFN-gamma plays a unique role in protection against low virulent *Trypanosoma cruzi* strain. PLoS Negl Trop Dis 6:e1598.
44. Schauer, R., G. Reuter, H. Muhlpfordt, A. F. Andrade, and M. E. Pereira. 1983. The occurrence of N-acetyl- and N-glycoloylneuraminic acid in *Trypanosoma cruzi*. Hoppe Seylers Z Physiol Chem 364:1053-1057.
45. Schenkman, S., L. Pontes de Carvalho, and V. Nussenzweig. 1992. *Trypanosoma cruzi* trans-sialidase and neuraminidase activities can be mediated by the same enzymes. J Exp Med 175:567-575.
46. Scudder, P., J. P. Doom, M. Chuenkova, I. D. Manger, and M. E. Pereira. 1993 Enzymatic characterization of beta-D-galactoside alpha 2,3-trans-sialidase from *Trypanosoma cruzi*. J Biol Chem 268:9886-9891.
47. Sebastiani, S., P. Allavena, C. Albanesi, F. Nasorri, G. Bianchi, C. Traidl, S. Sozzani, G. Girolomoni, and A. Cavani. 2001. Chemokine receptor expression and function in CD4+T lymphocytes with regulatory activity. J Immunol 166:996-1002.
48. Serbina, N. V., T. Jia, T. M. Hohl, and E. G. Pamer. 2008. Monocyte-mediated defense against microbial pathogens. Annual review of immunology 26:421-452.
49. Sheridan, G. K., and K. J. Murphy. 2013. Neuron-glia crosstalk in health and disease: fractalkine and CX3CR1 take centre stage. Open biology 3:130181.
50. Shibayama, E., and H. Koizumi. 1996. Cellular localization of the Trk neurotrophin receptor family in human non-neuronal tissues. Am J Pathol 148:1807-1818.
51. Sreejit, P., S. Kumar, and R. S. Verma. 2008. An improved protocol for primary culture of cardiomyocyte from neonatal mice. In vitro cellular & developmental biology. Animal 44:45-50.
52. Tamura, Y., K. Matsumura, M. Sano, H. Tabata, K. Kimura, M. Ieda, T. Arai, Y. Ohno, H. Kanazawa, S. Yuasa, R. Kaneda, S. Makino, K. Nakajima, H. Okano, and K. Fukuda. 2011. Neural crest-derived stem cells migrate and differentiate into cardiomyocytes after myocardial infarction. Arterioscler Thromb Vasc Biol 31:582-589.
53. Tapley, P., F. Lamballe, and M. Barbacid. 1992. K252a is a selective inhibitor of the tyrosine protein kinase activity of the trk family of oncogenes and neurotrophin receptors. Oncogene 7:371-381.
54. Teixeira, M. M., R. T. Gazzinelli, and J. S. Silva. 2002. Chemokines, inflammation and *Trypanosoma cruzi* infection. Trends Parasitol 18:262-265.
55. Truyens, C., A. Angelo-Barrios, F. Torrico, J. Van Damme, H. Heremans, and Y. Carlier. 1994. Interleukin-6 (IL-6) production in mice infected with *Trypanosoma cruzi*: effect of its paradoxical increase by anti-IL-6 monoclonal antibody treatment on infection and acute-phase and humoral immune responses. Infect Immun 62:692-696.
56. Unnikrishnan, M., and B. A. Burleigh. 2004. Inhibition of host connective tissue growth factor expression: a novel *Trypanosoma cruzi*-mediated response. FASEB J 18:1625-1635.
57. Wahab, N. A., B. S. Weston, and R. M. Mason. 2005. Connective tissue growth factor CCN2 interacts with and activates the tyrosine kinase receptor TrkA. J Am Soc Nephrol 16:340-351.
58. Wang, X., S. V. McLennan, T. J. Allen, and S. M. Twigg. 2010. Regulation of pro-inflammatory and pro-fibrotic factors by CCN2/CTGF in H9c2 cardiomyocytes. Journal of cell communication and signaling 4:15-23.
59. Weinkauf, C., and M. PereiraPerrin. 2009. *Trypanosoma cruzi* promotes neuronal and glial cell survival through the neurotrophic receptor TrkC. Infect Immun 77:1368-1375.
60. Weinkauf, C., R. Salvador, and M. PereiraPerrin. 2011. Neurotrophin receptor TrkC is an entry receptor for *Trypanosoma cruzi* in neural, glial, and epithelial cells. Infect Immun 79:4081-4087.
61. Zangi, L., K. O. Lui, A. von Gise, Q. Ma, W. Ebina, L. M. Ptaszek, D. Spater, H. Xu, M. Tabebordbar, R. Gorbatov, B. Sena, M. Nahrendorf, D. M. Briscoe, R. A. Li, A. J. Wagers, D. J. Rossi, W. T. Pu, and K. R. Chien. 2013. Modified mRNA directs the fate of heart progenitor cells and induces vascular regeneration after myocardial infarction. Nat Biotechnol 31:898-907.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to one or more of: U.S. patent application Ser. No. 13/345,210, filed on Jan. 6, 2012, abandoned, which is a continuation of application Ser. No. 11/365,743, filed Feb. 28, 2006, U.S. Pat. No. 8,114,412, which is a divisional of application Ser. No. 09/745,008, filed Dec. 20, 2000, U.S. Pat. No. 7,060,676, which claims the benefit of U.S. Provisional Application Ser. No. 60/172,881, filed Dec. 20, 1999; U.S. patent application Ser. No. 13/505,316, filed on May 1, 2012, which is the U.S. national phase application, pursuant to 35 U.S.C. §371, of International Patent Application No.: PCT/US2010/055700, filed Nov. 5, 2010, which claims the benefit of U.S. Provisional Application Ser. No. 61/258,961, filed Nov. 6, 2009; U.S. patent application Ser. No. 11/982,371, filed on Nov. 1, 2007, abandoned, which claims the benefit of U.S. Provisional Application Ser. No. 60/856,170, filed Nov. 2, 2006. The disclosures of the aforementioned applications are hereby incorporated herein in their entireties by reference.

All patents and publications mentioned in this specification are herein incorporated by reference to the same extent as if each independent patent and publication was specifically and individually indicated to be incorporated by reference.

What is claimed is:

1. A method of decreasing inflammation in a non-neuronal tissue of a subject in need thereof, the method comprising: administering to the subject soluble parasite-derived neurotrophic factor (sPDNF) polypeptide of SEQ ID NO: 2, which binds to the TrkA receptor and/or the TrkC receptor on non-neuronal cells or tissue, or a TrkA receptor binding portion of the sPDNF polypeptide selected from residues 1-588 of SEQ ID NO: 2, residues 33-666 of SEQ ID NO: 2, or residues 425-455 of SEQ ID NO: 2, in an amount effective to decrease inflammation in the non-neuronal tissue, wherein the non-neuronal cells or tissue are cardiac or hepatic cells or tissue.

2. The method of claim 1, wherein the subject has or is at risk of having a cardiac inflammatory disease or a hepatic inflammatory disease.

3. The method of claim 2, wherein the cardiac inflammatory disease is myocarditis, cardiomyopathy, endocarditis, or pericarditis, and wherein the hepatic inflammatory disease is hepatitis and/or cirrhosis.

4. The method of claim 1, wherein the subject does not have Chagas disease.

5. A method of treating a cardiac or hepatic inflammatory disease in a subject in need thereof, the method comprising: administering to said subject a therapeutically effective amount of soluble parasite-derived neurotrophic factor (sPDNF) polypeptide as set forth in SEQ ID NO: 2 which binds to the TrkA receptor and/or the TrkC receptor on cardiac or hepatic non-neuronal cells or tissue, or a TrkA receptor binding portion of the sPDNF polypeptide selected from residues 1-588 of SEQ ID NO: 2, residues 33-666 of SEQ ID NO: 2, or residues 425-455 of SEQ ID NO: 2.

6. The method of claim 5, wherein the cardiac inflammatory disease is myocarditis, cardiomyopathy, endocarditis, or pericarditis, and wherein the hepatic inflammatory disease is hepatitis and/or cirrhosis.

7. The method of claim 5, wherein the subject does not have Chagas disease.

* * * * *

UNITED STATES PATENT AND TRADEMARK OFFICE
CERTIFICATE OF CORRECTION

PATENT NO. : 9,744,220 B2
APPLICATION NO. : 14/768157
DATED : August 29, 2017
INVENTOR(S) : Mercio A. Perrin Page 1 of 1

It is certified that error appears in the above-identified patent and that said Letters Patent is hereby corrected as shown below:

In the Specification
At Column 1, Line 20-23, delete "This invention was made with government support under Grant Nos. NS040574, NS42960, and AI09738 awarded by the National Institutes of Health (NIH). The U.S. government has certain rights in the invention." and replace with -- This invention was made with government support under grant numbers NS040574 and NS042960 awarded by the National Institutes of Health. The government has certain rights in the invention. --

Signed and Sealed this
Thirty-first Day of December, 2019

Andrei Iancu
*Director of the United States Patent and Trademark Office*